United States Patent
Chen et al.

(10) Patent No.: US 11,214,625 B2
(45) Date of Patent: Jan. 4, 2022

(54) APPLICATION OF PCSK9 INHIBITORS IN THE PREPARATION OF DRUGS FOR THE TREATMENT OF INFLAMMATORY IMMUNE DISEASES

(71) Applicant: Min Chen, Jiangsu (CN)

(72) Inventors: Min Chen, Jiangsu (CN); Rong Yuan, Jiangsu (CN); Chao Luan, Jiangsu (CN)

(*) Notice: Subject to any disclaimer, the term of this patent is extended or adjusted under 35 U.S.C. 154(b) by 173 days.

(21) Appl. No.: 15/965,907

(22) Filed: Apr. 28, 2018

(65) Prior Publication Data

US 2018/0312607 A1 Nov. 1, 2018

Related U.S. Application Data

(63) Continuation-in-part of application No. PCT/CN2016/111613, filed on Dec. 23, 2016.

(30) Foreign Application Priority Data

Oct. 29, 2015 (CN) .......................... 201510728438.6

(51) Int. Cl.
| | |
|---|---|
| C07K 16/40 | (2006.01) |
| C12N 15/113 | (2010.01) |
| C12N 9/64 | (2006.01) |
| A61K 31/4743 | (2006.01) |
| A61P 17/06 | (2006.01) |
| A61K 31/437 | (2006.01) |
| A61K 39/00 | (2006.01) |

(52) U.S. Cl.
CPC ............ *C07K 16/40* (2013.01); *A61K 31/437* (2013.01); *A61K 31/4743* (2013.01); *A61P 17/06* (2018.01); *C12N 9/6454* (2013.01); *C12N 15/1137* (2013.01); *C12Y 304/21061* (2013.01); *A01K 2217/075* (2013.01); *A01K 2227/105* (2013.01); *A01K 2267/0368* (2013.01); *A61K 2039/505* (2013.01); *C07K 2317/21* (2013.01); *C12N 2310/14* (2013.01)

(58) Field of Classification Search
CPC C07K 16/40; C07K 2317/21; C12K 15/1137; C12Y 304/2106; C12N 9/6454; C12N 2310/14; A61K 31/4743; A61K 31/437; A61K 2039/505; A61P 17/06; A01K 227/105; A01K 2267/0368; A01K 2217/075
See application file for complete search history.

(56) References Cited

U.S. PATENT DOCUMENTS

| | | |
|---|---|---|
| 9,227,956 B2 | 1/2016 | Darout et al. |
| 10,513,514 B2 * | 12/2019 | Wu .......................... A61P 3/06 |
| 2014/0315928 A1 | 10/2014 | Darout et al. |
| 2015/0374710 A1 | 12/2015 | Abdel-Meguid et al. |
| 2015/0376139 A1 | 12/2015 | Abdel-Meguid et al. |
| 2016/0058768 A1 | 3/2016 | Darout et al. |
| 2016/0256467 A1 | 9/2016 | Abdel-Meguid et al. |
| 2017/0290806 A1 | 10/2017 | Abou-Gharbia et al. |

FOREIGN PATENT DOCUMENTS

| | | |
|---|---|---|
| CN | 103717615 A | 4/2014 |
| CN | 105143203 A | 12/2015 |
| CN | 105214087 A | 1/2016 |
| EP | 0372776 A2 | 6/1990 |
| TW | 201400464 A | 1/2014 |
| WO | 2012/177741 A1 | 12/2012 |
| WO | WO 2013137371 * | 9/2013 |
| WO | 2014/150395 A1 | 9/2014 |
| WO | 2014/170786 A1 | 10/2014 |
| WO | WO 2014/170786 * | 10/2014 |
| WO | 2014/197752 A1 | 12/2014 |
| WO | 2016/107602 A1 | 7/2016 |
| WO | 2016/107603 A1 | 7/2016 |
| WO | 2017/034990 A1 | 3/2017 |
| WO | 2017/034994 A1 | 3/2017 |
| WO | 2017/034997 A1 | 3/2017 |

(Continued)

OTHER PUBLICATIONS

International Search Report for International Application No. PCT/CN2016/111613, dated Feb. 20, 2017 (translation).
Written Opinion of the International Searching Authority for International Application No. PCT/CN2016/111613, dated Feb. 20, 2017 (translation).
Mao, Chengyu et al., "Research progress on proprotein convertase subtilisin 9," Journal of Integrated Traditional Chinese and Western Medicine Cardiovascular Diseases, Issue 10, 2015, 191-194 (translated abstract).
Pan, Lihong et al., "PCSK9/Narc-1 and nervous system diseases," Journal of Nanhua University (Medical Edition), Issue 6, 2008, 808-809 (translated abstract).

*Primary Examiner* — Shirley V Gembeh
(74) *Attorney, Agent, or Firm* — Andrew D. Fortney; Central California IP Group, P.C.

(57) ABSTRACT

The invention belongs to the biopharmaceutical. It involves the role and mechanism of PCSK9 in inflammatory immune diseases, and the application of PCSK9 inhibitors to the preparation of drugs for the treatment of inflammatory immune diseases mediated by T cells. In particular, it involves the use of PCSK9 monoclonal antibody, PCSK9 interference RNA and PCSK9 small molecule inhibitors for treating psoriasis, atopic dermatitis, or urticaria. The invention uses psoriasis as an embodiment for the study of inflammatory and immune diseases. It is found that PCSK9 plays an important role in the treatment of inflammatory immune diseases. The PCSK9 monoclonal antibody, PCSK9 interference RNA, and PCSK9 small molecule inhibitor can be further developed for treating inflammatory immune-diseases, such as psoriasis with fewer adverse reactions, at low cost, and with good efficacy.

19 Claims, 17 Drawing Sheets
Specification includes a Sequence Listing.

(56) References Cited

FOREIGN PATENT DOCUMENTS

WO      2017/071673   A1    5/2017
WO      2017/222953   A1    12/2017

* cited by examiner

Before treatment — After 5 days by treatment

Lesion  Non-lesion  Healthy control

The compound structure of the PCSK9 small molecule inhibitor

APPLICATION OF PCSK9 INHIBITORS IN THE PREPARATION OF DRUGS FOR THE TREATMENT OF INFLAMMATORY IMMUNE DISEASES

SEQUENCE LISTING SUBMISSION VIA EFS-WEB

A computer readable text file, entitled "SequenceListing.txt" created on or about Jul. 17, 2020 with a file size of about 66 kb contains the sequence listing for this application and is hereby incorporated by reference in its entirety.

THE TECHNICAL FIELD

The invention belongs to the field of biopharmaceutical technology, including the role and mechanism of PCSK9 in inflammatory immune diseases and the application of PCSK9 inhibitors in the preparation of drugs for treating inflammatory immune diseases.

BACKGROUND

The incidence of inflammatory immune diseases is high, and there are at least hundreds of millions of people worldwide, including many autoimmune diseases, such as psoriasis, eczema (atopic dermatitis), lupus erythematosus, rheumatoid arthritis, dermatomyositis, scleroderma, Crohn's Disease, etc.). Because these diseases can involve multiple organs, leading to organ injury of heart, liver, kidney, blood vessel, lung, joint and brain. Its mortality rate is second only to malignant tumor. In view of the fact that the etiology and pathogenesis of these diseases is quite complex and cannot be cured at present. Glucocorticoids and immunosuppressants are the main therapeutic drugs commonly used in clinical practice. The effective rate of these drugs is only about 50%. And the severe adverse side effect, which include bone marrow suppression, liver and kidney dysfunction, osteoporosis, susceptibility to infection and tumors, greatly limit long-term use of such drugs. In recent years, the biologics have gradually become the popular direction of drug research and development due to the selectivity of the therapeutic targets and the little side effects. But so far, only a few of these biologic drugs have achieved great efficacy. At the same time, high prices limit wide application.

Proprotein convertase subtilisin kexin 9 (PCSK9) is a member of the proprotein convertase family, which is secreted as an inactive proenzyme in the liver. The cDNA of the PCSK9 gene is 3617 bp, which encodes a PCSK9 protein with 692 amino acids. The PCSK9 precursor separated N-terminal predomain by intramolecular catalyzing, then the separated N-terminal anterior region is connected to catalytic region to allow mature PCSK9 proteins to leave the endoplasmic reticulum and enter the secretory pathway. After PCSK9 is secreted into the extracellular space, it binds at the cell surface to the low density lipoprotein (LDL) receptor in the first epidermal growth factor like domain. Following binding, PCSK9-LDL binding receptor complex enters lysosome to degrade, which leads to the decrease of LDL receptors on the cell surface. Therefore, the level of PCSK9 is negatively correlated with the level of LDL receptor. Several studies have shown that the mutation of PCSK9 gene can significantly decrease the LDL cholesterol level and the incidence of coronary heart disease in different patient groups.

In view of the significant effect of inhibition of PCSK9 on reducing LDL cholesterol and coronary disease, a number of treatment schemes have been developed to deactivate PCSK9, for the purpose of reducing LDL cholesterol and coronary disease. Because of its high efficiency, target selectivity, and good stability, monoclonal antibodies have become a hot spot in new drug research. Two PCSK9 monoclonal antibodies have recently been approved by FDA and the European Medicines Agency (EMA) for treating hypercholesterolemia in patients who are still unable to reduce LDL by current treatments.

The PCSK9 monoclonal antibodies that have been launched to treat hypercholesterolemia include Alirocumab (SAR236553/REGN727, Sanofi & Regeneron Pharma) and Evolocumab (AMG 145, Amgen). Preclinical trials of other PCSK9 monoclonal antibodies, such as Pfizer's Bococizumab (as RN316/PF 04950615) and LY3015014 (Eli Lilly and Company), have been completed. Overall, the clinical research found that the patients with hypercholesterolemia treated with these drugs had good tolerance, and there was no significant difference in the incidence of adverse reactions between the placebo group and the active treatment group.

The main target for inhibition of PCSK9 secretion is mRNAs, which can be obtained by using antisense oligonucleotides (ASOS) to obtain their short sequences, which can be given intravenously in the form of small lipid nanoparticles. In rats, liver-specific siRNA targeting PCSK9 could make the maximum silencing efficiency at 50-60%. The plasma LDL cholesterol level decreased by 30%. In non-human primates, a dose of 5 mg drug reduced LDL cholesterol by 56-70% after 72 hours and lasted for 3 weeks. In phase I trial, the siRNA oligonucleotide ALN-PCS02 was investigated. Compared with placebo, the drug can quickly reduce the level of PCSK9 (average 68%) and LDL cholesterol (average 41%) in a dose-dependent manner. The drug is safe and has no obvious adverse effects.

For PCSK9 small molecule inhibitors, Pfizer is developing a PCSK9 small molecule inhibitor. In animal experiments, the drug can significantly reduce LDL cholesterol level. In addition, the company is designing a vaccine drug that patients need only once a year to achieve a long-term reduction in LDL.

However, so far, all new research and drug development projects related to PCSK9 inhibitors have been based on their role in reducing LDL cholesterol level and coronary disease. So far, there has been no reporting on the use of PCSK9 inhibitors in the treatment of inflammatory and immune diseases.

It is well known that the incidence of inflammatory immune diseases is high; their pathogenesis is complex and they include many diseases. However, there are often similar etiological or pathological bases among different inflammatory immune diseases. They are usually treated with the same drugs: glucocorticoids and immunosuppressants, which are used most frequently in clinical practice. For the development of new drugs, the high degree of similarity in the treatment and medication of various types of inflammatory immune diseases. so a disease model that is easy to observe and analyze the outcome of the treatment is usually chosen to carry out the preliminary study. At present, because the therapeutic effect of psoriatic lesions is easy to observe, it has become the experimental field to generally study the treatment of inflammatory immune diseases. Psoriasis is an immunological disease mediated by T cells with multiple genetic mutation background. It is susceptible to be associated with metabolic syndrome (hypertension, hyperlipidemia, hyperglycemia and obesity) and cardiovascular disease. The disease is prone to relapse and requires lifelong treatment. Psoriasis mainly includes four types: psoriasis vulgaris, psoriasis pustulose, psoriasis erythematosus, and psoriasis arthritis. According to the severity it is divided into mild, moderate, severe. At present, immunosuppressants and retinoic acid are commonly used in the treatment of severe psoriasis. Adverse reactions are common, including bone marrow suppression, liver and kidney injury and hyperlipidemia. Psoriatic Arthritis (PsA) is the second most common inflammatory joint disease, which can lead to disability. Compared with rheumatoid arthritis (RA), PsA lacks appropriate treatment drugs. Antirheumatic drugs for improving the condition of the disease such as Methotrexate, leflunomide and other antirheumatics, which lack randomized experimental evidence, have been the first line PsA treatment. With the research progress on the pathogenesis of the disease, biological agents, which are the key targets of the pathogenesis of the disease have been gradually used in clinical treatment. At present, biological agents used in the treatment of psoriasis and PsA mainly include monoclonal antibodies (mAbs) against TNF-α, a target of immune pathogenesis pathway. They include inflexim monoclonal antibody (trade name: Remicade), adamumab injection (trade name: Merlot), human recombinant II tumor necrosis factor receptor antibody fusion protein for injection (trade name: Etanercept), and Ulinumab, which targets IL-12 and IL-23 common subunit P40. However, about 30% of patients may show poor or ineffective response to these drugs, and long-term use also carries the risk of inducing infection (including tuberculosis) and tumors. Both the European Drug Agency (EMA) and the Food and Drug Administration (FDA) found that there seemed to be no better treatment for those who don't respond to the currently available drug. In conclusion, none of the currently available drugs can effectively improve metabolic disorders in psoriatic patients. So far, no therapeutic target has been found to treat psoriatic lesions and metabolic abnormalities.

DETAILED DESCRIPTION OF THE INVENTION

Technical Issues

Figure 1:
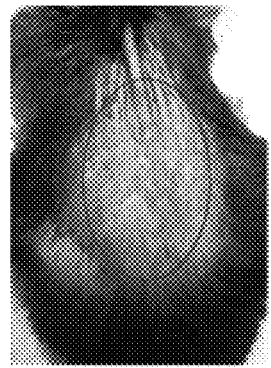
FIG. 1: Mild skin inflammation was observed in IMQ treatment region of PCSK9 knockout mice. After 5 days of continuous coating, marked erythema, thickening of scales and lesions were observed and measured in the coating area of at the back of C57BL/6 mice. In PCSK9 knockout mice, there were only slight erythema, thickening of scales and lesions.
Figure 1:
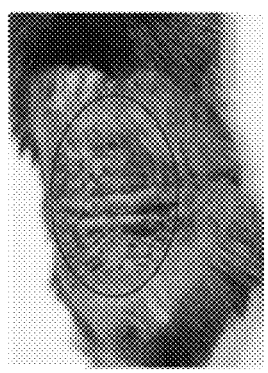
Figure 1:
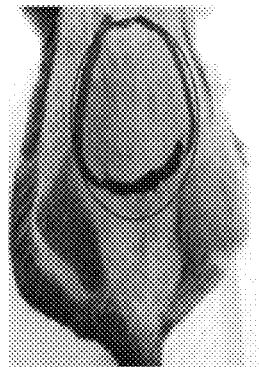
Figure 1:
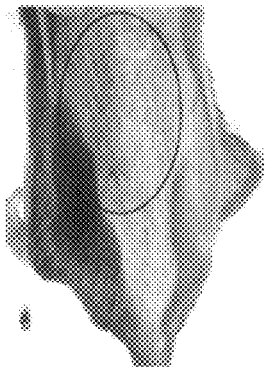
Figure 2:
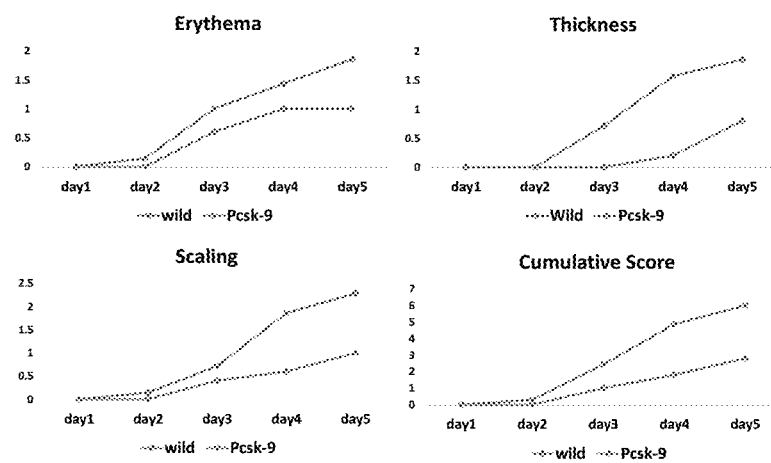
FIG. 2: The score of skin inflammation (erythema+scale+infiltration) in PCSK9 knockout mice were significantly lower than that in control group (P<0.05). A daily score was given on the skin lesions of the drug-coated area on the back of the mice, the erythema, scale, lesion thickening and total score of C57BL/6 mice were significantly higher than those of PCSK9 gene knockout mice (P<0.05).

The problems to be solved in the present invention: the role and mechanism of PCSK9 in the treatment of inflammatory immune diseases and the application of PCSK9 inhibitors in the preparation of drugs for the treatment of inflammatory immune diseases. The invention uses psoriasis as an example for the study of inflammatory immune diseases, and finds that PCSK9 plays an important role in the treatment of a variety of inflammatory immune diseases.

Technical Solution

We first found that PCSK9 plays an important role in the treatment of a variety of inflammatory immune diseases. We used PCSK9 knockout transgenic mice to establish psoriatic like inflammatory model induced by imiquimod, which proves that inhibition of PCSK9 has a very obvious therapeutic effect on psoriatic inflammatory lesions. A study on the mechanism of inhibiting PCSK9 in the treatment of inflammatory immune diseases by cultured human keratinocytes found that knock-down of PCSK9 expression by siRNA could significantly inhibit the abnormal proliferation of keratinocyte and promote its apoptosis through NFkb pathway.

To further confirm the role of PCSK9 in the pathogenesis of psoriasis, the invention collected lesions and non-lesions from 30 psoriasis patients, and skin samples from 30 normal human subjects. The immunohistochemistry results showed: the expression of PCSK9 in psoriatic lesions was significantly higher than that in non-lesions and normal controls (p<0.05). PCSK9 positive cells were mainly distributed in epidermis and dermis near the epidermis, but not in dermis vessels. Detected by real-time fluorescence quantitative nucleic acid amplification detection system (Q-PCR), it was found that the expression of PCSK9 was found in the skin of both patients and normal subjects, but it was significantly higher in the psoriasis patients than in the normal controls (P<0.01). No expression of PCSK9 was found in the peripheral blood mononuclear cells (PBMC) of patients with psoriasis, eczema, and urticaria and the control group by Q-PCR. However, the expression of PCSK9 in blood in patients with psoriasis, eczema and urticaria was significantly higher than that in the control group by ELISA (P<0.05).

Next, we isolated CD4 T cells from peripheral blood of patients with active psoriasis, eczema and urticaria and found PCSK9 protein could significantly promote the secretion of IL-17, IL-2 and IFN-Gamma by CD4 T cells, and increased the expression of NFkb, especially in psoriatic patients.

In all PCSK9 inhibitors, representative monoclonal antibodies, small interfering RNA and small molecular inhibitors were selected herein. Treated psoriasis-like mice model by subcutaneous injection (the dose is the same as the known LDL cholesterol experiment) in comparison with control group. The results showed that the therapeutic effect of PCSK9 monoclonal antibody group and PCSK9 small molecule inhibitor group was significantly better than that of control group. There were no obvious adverse reactions in PCSK9 monoclonal antibody group and PCSK9 small molecule inhibitor group. The results showed that the systemic use of PCSK9 small molecule inhibitors and PCSK9 monoclonal antibodies had obvious therapeutic effects on psoriasis-like inflammation and the therapeutic effect was significantly better than that of the control group.

In some embodiments, representative PCSK9 small molecule inhibitors and PCSK9 monoclonal antibodies were prepared for use as an external ointment (drug concentration 0.001-0.05%) and applied to IMQ induced inflammatory psoriasis like lesions in mice once a day in comparison with external ointment without drugs as controls. The results showed that the efficacy of PCSK9 monoclonal antibody group and PCSK9 small molecule inhibitor group was significantly better than that of control group. The effect of PCSK9 small molecule inhibitor group was better than that of PCSK9 monoclonal antibody group, and there was no obvious adverse reaction in each group. It was proved that topical use of PCSK9 small molecule inhibitor and PCSK9 monoclonal antibody had obvious therapeutic effect on psoriasis-like inflammation and their efficacy was better than that of control group.

In some embodiments, representative PCSK9 small molecule interference RNA (siPCSK9) was applied to IMQ induced psoriasis like inflammatory lesions in mice, once a day. Compared with the control group, the lesions of the siPCSK9 group were improved obviously, and no obvious adverse reaction was found.

For the first time, it was found that: 1. Both systemic and topical use of PCSK9 monoclonal antibody, PCSK9 small molecule inhibitor, and siPCSK9 have therapeutic effects on psoriatic lesions, which are significantly superior to those of the control group. In some embodiments, the invention relates to the treatment of psoriatic lesion by a PCSK9 inhibitor selected from the group consisting of representative PCSK9 monoclonal antibody, PCSK9 small molecule inhibitor and siPCSK9.

Because of its high inhibiting efficiency, selectivity and good efficacy, monoclonal antibody has been widely used in the research of new drugs. Our study also found that, small molecular inhibitors and small interfering RNA aimed at PCSK9 were more effective than monoclonal antibodies in the treatment of psoriasis-like inflammation. Generally, monoclonal antibodies have fewer side effects than small molecular inhibitors, and are more stable than small interfering RNA preparations. However, according to our data, small molecular PCSK9 inhibitors and siPCSK9 not only have a good efficacy in the treatment of psoriasis like inflammation, but also have mild side effects.

It is well known to one skilled in this field that, based on the above mechanism of PCSK9, PCSK9 inhibitors have therapeutic effect on other T cell mediated chronic immune diseases. These include, but are not limited to, psoriasis, psoriatic arthritis, eczema (atopic dermatitis), urticaria, glucocorticoid dependent dermatitis, rheumatoid arthritis, scleroderma, diabetes, chronic liver disease and lymphoma, etc. In some embodiments, the invention relates to the treatment of a T-cell medicated chronic immune disease, wherein the T-cell medicated chronic immune disease is selected from psoriasis, psoriatic arthritis, eczema (atopic dermatitis), urticaria, glucocorticoid dependent dermatitis, rheumatoid arthritis, scleroderma, diabetes, chronic liver disease, and lymphoma; wherein the PCSK9 inhibitor is a PCSK9 small molecule inhibitor, a PCSK9 monoclonal antibody or a siPCSK9; wherein the PCSK9 inhibitor can be used alone or in combination with other therapeutic agents, including traditional drugs and other new biological agents.

In some embodiments, PCSK9 inhibitor comprising the PCSK9 monoclonal antibody, PCSK9 small molecule interfered RNA and PCSK9 small molecule inhibitors are used for treating psoriasis, atopic dermatitis or urticaria. In some embodiment, the PCSK9 inhibitor was applied topically on the skin.

In an embodiment, the invention relates to a method of treating psoriasis by topical use of a PCSK9 inhibitor, wherein the PCSK9 inhibitor is selected from the group consisting of a PCSK9 monoclonal antibody, a siPCSK9 and a PCSK9 small molecule inhibitor. In an embodiment, the PCSK9 inhibitor is a PCSK9 vaccine.

In an embodiment, the inhibition of PCSK9 expression by siPCSK9 can significantly inhibit the abnormal proliferation of human keratinocytes and promote their apoptosis through NFkb pathway. In an embodiment, the invention relates to a method of treating keratinocytes by the use of siPCSK9.

In an embodiment, the PCSK9 small molecule inhibitor is selected from the group consisting of

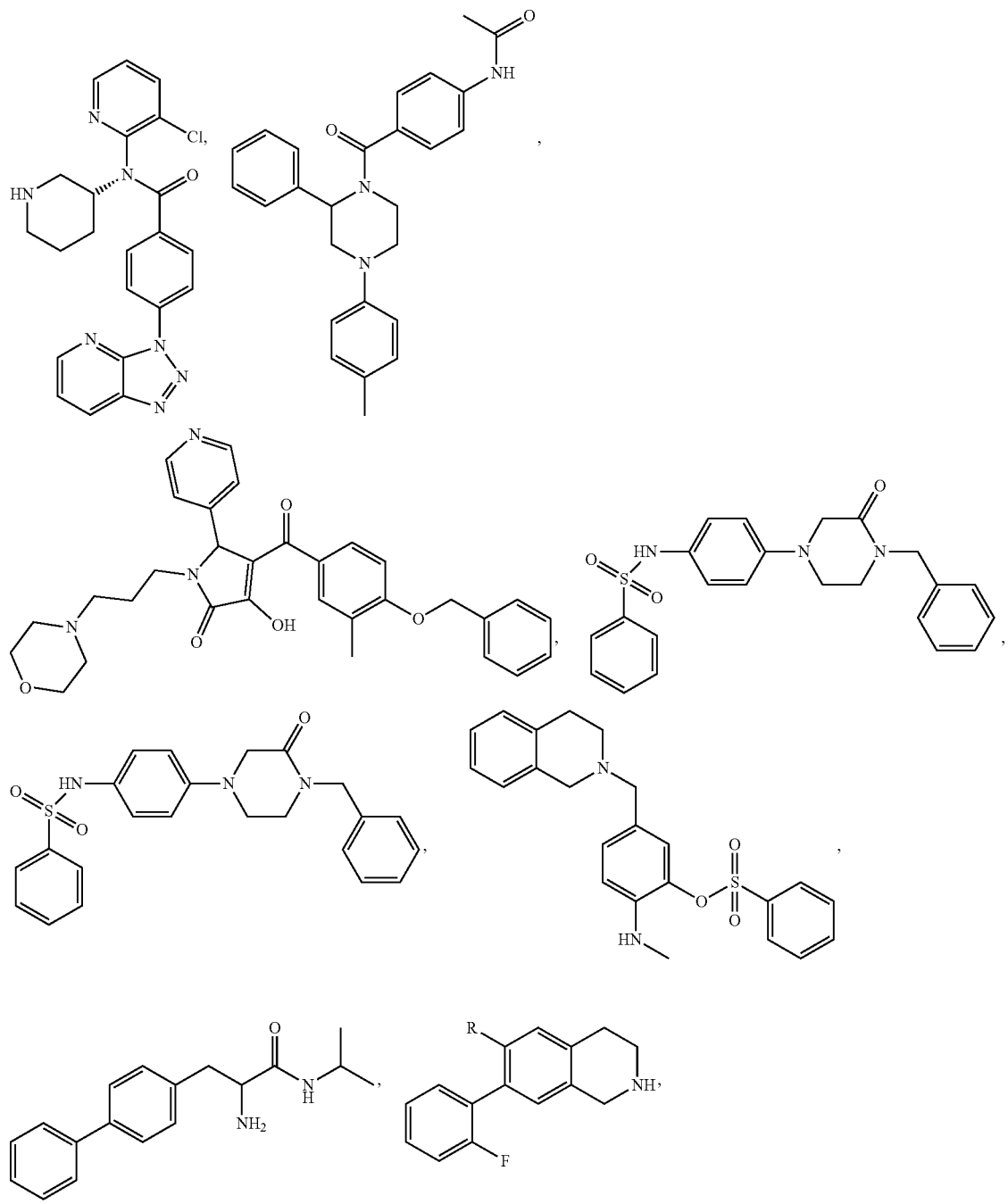

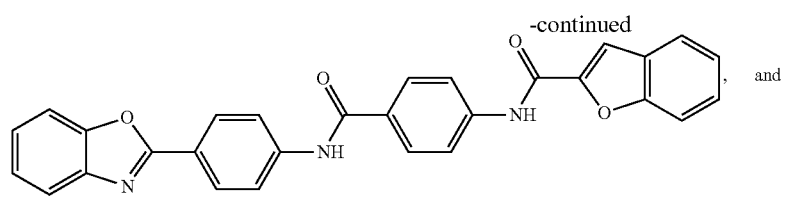, and 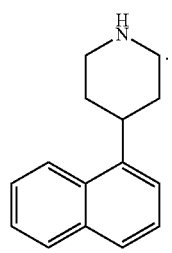.
In an embodiment, the PCSK9 small molecule inhibitor is selected from the compounds listed in Table 1. The patent application number cited in Table 1 are incorporated by reference in their entirety.
TABLE 1
| Compound No. | Structural formula | CAS | Patent Application No. |
|---|---|---|---|
| 1 | | 1632250-49-7 | WO2014170786<br>CN105143203 |
| 2 | | 1629166-02-4 | US20150376139<br>WO2016107603<br>WO2016107602<br>WO2014150395 |

TABLE 1-continued

| Compound No. | Structural formula | CAS | Patent Application No. |
|---|---|---|---|
| 3 | | SBC115076 | US2014022957 CN105228616 |
| 4 | | 1962177-03-2 | WO2016107603 |
| 5 | | 1000339-97-8 | WO2017034997 |
| 6 | | | |
| 7 | | 2087490-99-9 | WO2017034994 |
| 8 | | 2087440-16-0 | WO2017034990 WO2017034994 |

TABLE 1-continued

| Compound No. | Structural formula | CAS | Patent Application No. |
|---|---|---|---|
| 9 | | 423148-46-3 | WO2017222953 |
| 10 | | 130305-64-5 | EP372776 |

In an embodiment, the PCSK9 inhibitor is a PCSK9 antibody selected from the group consisting of Alirocumab, Evolocumab, Bococizumab, DS-001, CA-001, MS-001, LY3015014, NS-001, and antigen binding fragments, variants, conjugates or biosimilars thereof.

In an embodiment, the PCSK9 inhibitor is Alirocumab or antigen binding fragments, variants, conjugates or biosimilars thereof. In an embodiment, the PCSK9 inhibitor is a PCSK9 antibody comprising SEQ ID NO:1 and SEQ ID NO:2. In an embodiment, the PCSK9 inhibitor is a PCSK9 antibody comprising sequences at least 99% identical to SEQ ID NO:1 and SEQ ID NO:2. In an embodiment, the PCSK9 inhibitor is a PCSK9 antibody comprising sequences at least 95% identical to SEQ ID NO:1 and SEQ ID NO:2. In an embodiment, the PCSK9 inhibitor is a PCSK9 antibody comprising sequences at least 90% identical to SEQ ID NO:1 and SEQ ID NO:2.

In an embodiment, the PCSK9 inhibitor is Evolocumab or antigen binding fragments, variants, conjugates or biosimilars thereof. In an embodiment, the PCSK9 inhibitor is a PCSK9 antibody comprising SEQ ID NO:3, SEQ ID NO:4, SEQ ID NO:5 and SEQ ID NO:6. In an embodiment, the PCSK9 inhibitor is a PCSK9 antibody comprising sequences at least 99% identical to SEQ ID NO:3, SEQ ID NO:4, SEQ ID NO:5 and SEQ ID NO:6. In an embodiment, the PCSK9 inhibitor is a PCSK9 antibody comprising sequences at least 95% identical to SEQ ID NO:3, SEQ ID NO:4, SEQ ID NO:5 and SEQ ID NO:6. In an embodiment, the PCSK9 inhibitor is a PCSK9 antibody comprising sequences at least 90% identical to SEQ ID NO:3, SEQ ID NO:4, SEQ ID NO:5 and SEQ ID NO:6.

In an embodiment, the PCSK9 inhibitor is Bococizumab or antigen binding fragments, variants, conjugates or biosimilars thereof. In an embodiment, the PCSK9 inhibitor is a PCSK9 antibody comprising SEQ ID NO:7, SEQ ID NO:8, SEQ ID NO:9, SEQ ID NO:10, SEQ ID NO:11, SEQ ID NO:12, SEQ ID NO:13, SEQ ID NO:14, and SEQ ID NO:15. In an embodiment, the PCSK9 inhibitor is a PCSK9 antibody comprising sequences at least 99% identical to SEQ ID NO:7, SEQ ID NO:8, SEQ ID NO:9, SEQ ID NO:10, SEQ ID NO:11, SEQ ID NO:12, SEQ ID NO:13, SEQ ID NO:14, and SEQ ID NO:15. In an embodiment, the PCSK9 inhibitor is a PCSK9 antibody comprising sequences at least 95% identical to SEQ ID NO:7, SEQ ID NO:8, SEQ ID NO:9, SEQ ID NO:10, SEQ ID NO:11, SEQ ID NO:12, SEQ ID NO:13, SEQ ID NO:14, and SEQ ID NO:15. In an embodiment, the PCSK9 inhibitor is a PCSK9 antibody comprising sequences at least 90% identical to SEQ ID NO:7, SEQ ID NO:8, SEQ ID NO:9, SEQ ID NO:10, SEQ ID NO:11, SEQ ID NO:12, SEQ ID NO:13, SEQ ID NO:14, and SEQ ID NO:15.

In an embodiment, the PCSK9 inhibitor is DS-001 or antigen binding fragments, variants, conjugates or biosimilars thereof. In an embodiment, DS-001 is a PCSK9 antibody comprising SEQ ID NO:16, SEQ ID NO:17, SEQ ID NO:18, and SEQ ID NO:19. In an embodiment, the PCSK9 inhibitor is a PCSK9 antibody comprising sequences at least 99% identical to SEQ ID NO:16, SEQ ID NO:17, SEQ ID NO:18, and SEQ ID NO:19. In an embodiment, the PCSK9 inhibitor is a PCSK9 antibody comprising sequences at least 95% identical to SEQ ID NO:16, SEQ ID NO:17, SEQ ID NO:18, and SEQ ID NO:19. In an embodiment, the PCSK9 inhibitor is a PCSK9 antibody comprising sequences at least 90% identical to SEQ ID NO:16, SEQ ID NO:17, SEQ ID NO:18, and SEQ ID NO:19.

In an embodiment, the PCSK9 inhibitor is CA-001 or antigen binding fragments, variants, conjugates or biosimilars thereof. In an embodiment, CA-001 is a PCSK9 antibody comprising SEQ ID NO:20, and SEQ ID NO:21. In an embodiment, the PCSK9 inhibitor is a PCSK9 antibody comprising sequences at least 99% identical to SEQ ID NO:20, and SEQ ID NO:21. In an embodiment, the PCSK9 inhibitor is a PCSK9 antibody comprising sequences at least 95% identical to SEQ ID NO:20, and SEQ ID NO:21. In an embodiment, the PCSK9 inhibitor is a PCSK9 antibody comprising sequences at least 90% identical to SEQ ID NO:20, and SEQ ID NO:21.

In an embodiment, the PCSK9 inhibitor is MS-001 or antigen binding fragments, variants, conjugates or biosimilars thereof. In an embodiment, MS-001 is a PCSK9 antibody comprising SEQ ID NO:22, SEQ ID NO:23, SEQ ID NO:24, SEQ ID NO:25 SEQ ID NO:26, SEQ ID NO:27, SEQ ID NO:28, SEQ ID NO:29, SEQ ID NO:30, SEQ ID NO:31, SEQ ID NO:32, and SEQ ID NO:33. In an embodiment, the PCSK9 inhibitor is a PCSK9 antibody comprising sequences at least 99% identical to SEQ ID NO:22, SEQ ID NO:23, SEQ ID NO:24, SEQ ID NO:25 SEQ ID NO:26, SEQ ID NO:27, SEQ ID NO:28, SEQ ID NO:29, SEQ ID NO:30, SEQ ID NO:31, SEQ ID NO:32, and SEQ ID NO:33. In an embodiment, the PCSK9 inhibitor is a PCSK9 antibody comprising sequences at least 95% identical to SEQ ID NO:22, SEQ ID NO:23, SEQ ID NO:24, SEQ ID NO:25 SEQ ID NO:26, SEQ ID NO:27, SEQ ID NO:28, SEQ ID NO:29, SEQ ID NO:30, SEQ ID NO:31, SEQ ID NO:32, and SEQ ID NO:33. In an embodiment, the PCSK9 inhibitor is a PCSK9 antibody comprising sequences at least 90% identical to SEQ ID NO:22, SEQ ID NO:23, SEQ ID NO:24, SEQ ID NO:25 SEQ ID NO:26, SEQ ID NO:27, SEQ ID NO:28, SEQ ID NO:29, SEQ ID NO:30, SEQ ID NO:31, SEQ ID NO:32, and SEQ ID NO:33.

In an embodiment, the PCSK9 inhibitor is LY3015014 or antigen binding fragments, variants, conjugates or biosimilars thereof. In an embodiment, LY3015014 is a PCSK9 antibody comprising SEQ ID NO:34 and SEQ ID NO:35. In an embodiment, the PCSK9 inhibitor is a PCSK9 antibody comprising sequences at least 99% identical to SEQ ID NO:34 and SEQ ID NO:35. In an embodiment, the PCSK9 inhibitor is a PCSK9 antibody comprising sequences at least 95% identical to SEQ ID NO:34 and SEQ ID NO:35. In an embodiment, the PCSK9 inhibitor is a PCSK9 antibody comprising sequences at least 90% identical to SEQ ID NO:34 and SEQ ID NO:35.

In an embodiment, the PCSK9 inhibitor is NS-001 or antigen binding fragments, variants, conjugates or biosimilars thereof. In an embodiment, NS-001 is a PCSK9 antibody comprising SEQ ID NO:36, SEQ ID NO:37, SEQ ID NO:38, SEQ ID NO:39, SEQ ID NO:40, and SEQ ID NO:41. In an embodiment, the PCSK9 inhibitor is a PCSK9 antibody comprising sequences at least 99% identical to SEQ ID NO:36, SEQ ID NO:37, SEQ ID NO:38, SEQ ID NO:39, SEQ ID NO:40, and SEQ ID NO:41. In an embodiment, the PCSK9 inhibitor is a PCSK9 antibody comprising sequences at least 95% identical to SEQ ID NO:36, SEQ ID NO:37, SEQ ID NO:38, SEQ ID NO:39, SEQ ID NO:40, and SEQ ID NO:41. In an embodiment, the PCSK9 inhibitor is a PCSK9 antibody comprising sequences at least 90% identical to SEQ ID NO:36, SEQ ID NO:37, SEQ ID NO:38, SEQ ID NO:39, SEQ ID NO:40, and SEQ ID NO:41.

TABLE 2

| SEQ ID NO. | Description | Sequence |
|---|---|---|
| 1 | Alirocumab Variable zone in heavy chain | Glu Met Gln Leu Val Glu Ser Gly Gly Gly Leu Val Gln Pro Gly Gly Ser Leu Arg Leu Ser Cys Ala Ala Ser Gly Phe Thr Phe Ser Ser His Trp Met Lys Trp Val Arg Gln Ala Pro Gly Lys Gly Leu Glu Trp Val Ala Asn Ile Asn Gln Asp Gly Ser Glu Lys Tyr Tyr Val Asp Ser Val Lys Gly Arg Phe Thr Ile Ser Arg Asp Asn Ala Lys Asn Ser Leu Phe Leu Gln Met Asn Ser Leu Arg Ala Glu Asp Thr Ala Val Tyr Tyr Cys Ala Arg Asp Ile Val Leu Met Val Tyr Asp Met Asp Tyr Tyr Tyr Gly Met Asp Val Trp Gly Gln Gly Thr Thr Val Thr Val Ser Ser |
| 2 | Alirocumab Variable zone in light chain | Asp Ile Val Met Thr Gln Ser Pro Leu Ser Leu Pro Val Thr Pro Gly Glu Pro Ala Ser Ile Ser Cys Arg Ser Ser Gln Ser Leu Leu His Ser Asn Gly Asn Asn Tyr Leu Asp Trp Tyr Leu Gln Lys Pro Gly Gln Ser Pro Gln Leu Leu Ile Tyr Leu Gly Ser Asn Arg Ala Ser Gly Val Pro Asp Arg Phe Ser Gly Ser Gly Ser Gly Thr Asp Phe Thr Leu Lys Ile Ser Arg Val Glu Ala Glu Asp Val Gly Val Tyr Tyr Cys Met Gln Thr Leu Gln Thr Pro Leu Thr Phe Gly Gly Gly Thr Lys Val Glu Ile Lys |
| 3 | Evolocumab Variable zone in heavy chain | Glu Val Gln Leu Val Glu Ser Gly Gly Gly Leu Val Lys Pro Gly Gly Ser Leu Arg Leu Ser Cys Ala Ala Ser Gly Phe Thr Phe Ser Ser Tyr Ser Met Asn Trp Val Arg Gln Ala Pro Gly Lys Gly Leu Glu Trp Val Ser Ser Ile Ser Ser Ser Ser Ser Tyr Ile Ser Tyr Ala Asp Ser Val Lys Gly Arg Phe Thr Ile Ser Arg Asp Asn Ala Lys Asn Ser Leu Tyr Leu Gln Met Asn Ser Leu Arg Ala Glu Asp Thr Ala Val Tyr Phe Cys Ala Arg Asp Tyr Asp Phe Trp Ser Ala Tyr Tyr Asp Ala Phe Asp Val Trp Gly Gln Gly Thr Met Val Thr Val Ser Ser |
| 4 | Evolocumab Variable zone in light chain | Gln Ser Val Leu Thr Gln Pro Pro Ser Val Ser Gly Ala Pro Gly Gln Arg Val Thr Ile Ser Cys Thr Gly Ser Ser Ser Asn Ile Gly Ala Gly Tyr Asp Val His Trp Tyr Gln Gln Leu Pro Gly Thr Ala Pro Lys Leu Leu Ile Ser Gly Asn Ser Asn Arg Pro Ser Gly Val Pro Asp Arg Phe Ser Gly Ser Lys Ser Gly Thr Ser Ala Ser Leu Ala Ile Thr Gly Leu Gln Ala Glu Asp Glu Ala Asp Tyr Tyr Cys Gln Ser Tyr Asp Ser Ser Leu Ser Gly Ser Val Phe Gly Gly Gly Thr Lys Leu Thr Val Leu |
| 5 | Evolocumab Variable zone in heavy chain | Gln Val Gln Leu Val Gln Ser Gly Ala Glu Val Lys Lys Pro Gly Ala Ser Val Lys Val Ser Cys Lys Ala Ser Gly Tyr Thr Leu Thr Ser Tyr Gly Ile Ser Trp Val Arg Gln Ala Pro Gly Gln Gly Leu Glu Trp Met Gly Trp Val Ser Phe Tyr Asn Gly Asn Thr Asn Tyr Ala Gln Lys Leu Gln Gly Arg Gly Thr Met Thr Thr Asp Pro Ser Thr Ser Thr Ala Tyr Met Glu Leu Arg Ser Leu Arg Ser Asp Asp Thr Ala Val Tyr Tyr Cys Ala Arg Gly Tyr Gly Met Asp Val Trp Gly Gln Gly Thr Thr Val Thr Val Ser Ser |
| 6 | Evolocumab Variable zone in light chain | Gln Ser Ala Leu Thr Gln Pro Ala Ser Val Ser Gly Ser Pro Gly Gln Ser Ile Thr Ile Ser Cys Thr Gly Thr Ser Ser Asp Val Gly Gly Tyr Asn Ser Val Ser Trp Tyr Gln Gln His Pro Gly Lys Ala Pro Lys Leu Met Ile Tyr Glu Val Ser Asn Arg Pro Ser Gly Val Ser Asn Arg Phe Ser Gly Ser Lys Ser Gly Asn Thr Ala Ser Leu Thr Ile Ser Gly |

TABLE 2-continued

| SEQ ID NO. | Description | Sequence |
|---|---|---|
| | | Leu Gln Ala Glu Asp Glu Ala Asp Tyr Tyr Cys Asn Ser Tyr Thr Ser Thr Ser Met Val Phe Gly Gly Gly Thr Lys Leu Thr Val Leu |
| 7 | Bococizumab Heavy chain: CDR1 | Ser Tyr Tyr Met His |
| 8 | Bococizumab Heavy chain: CDR1 | Gly Tyr Thr Phe Thr Ser Tyr Tyr Met His |
| 9 | Bococizumab Heavy chain: CDR1 | Gly Tyr Thr Phe Thr Ser Tyr |
| 10 | Bococizumab Heavy chain: CDR2 | Ser Pro Phe Gly Gly Arg |
| 11 | Bococizumab Heavy chain: CDR2 | Glu Ile Ser Pro Phe Gly Gly Arg Thr Asn Tyr Asn Glu Lys Phe Lys Ser |
| 12 | Bococizumab Heavy chain: CDR3 | Glu Arg Pro Leu Tyr Ala Ser Asp Leu |
| 13 | Bococizumab Light chain: CDR1 | Arg Ala Ser Gln Gly Ile Ser Ser Ala Leu Ala |
| 14 | Bococizumab Light chain: CDR2 | Ser Ala Ser Tyr Arg Tyr Thr |
| 15 | Bococizumab Light chain: CDR3 | Gln Gln Arg Tyr Ser Leu Trp Arg Thr |
| 16 | DS-001 | Ala Ser Asp Glu Glu Ile Gln Asp Val Ser Gly Thr Trp Tyr Leu Lys Ala Met Thr Val Asp Arg Phe Lys Ile Ala Ser Trp Pro Arg Ser Val Thr Pro Met Thr Leu Thr Thr Leu Glu Gly Gly Asn Leu Glu Ala Lys Val Thr Met Asn Trp Trp Gly Arg Ser Gln Glu Val Lys Ala Val Leu Glu Arg Thr Asp Glu Pro Gly Lys Tyr Thr Ala Gln Gly Asp Arg His Val Ala Tyr Ile Ile Arg Ser Pro Val Lys Asp His Tyr Ile Phe Tyr Ser Glu Gly Asn Leu Gln Gly Glu Thr Val Pro Gly Val Trp Leu Val Gly Arg Asp Pro Lys Asn Asn Leu Glu Ala Leu Glu Asp Phe Glu Lys Ala Ala Gly Ala Arg Gly Leu Ser Thr Glu Ser Ile Leu Ile Pro Arg Gln Ser Glu Thr Ser Ser Pro Gly |
| 17 | DS-001 | Gly Ala Ser Asp Glu Glu Ile Gln Asp Val Ser Gly Thr Trp Tyr Leu Lys Ala Met Thr Val Asp Arg Phe Lys Ile Ala Ser Trp Pro Arg Ser Val Thr Pro Met Thr Leu Thr Thr Leu Glu Gly Gly Asn Leu Glu Ala Lys Val Thr Met Asn Trp Trp Gly Arg Ser Gln Glu Val Lys Ala Val Leu Glu Arg Thr Asp Glu Pro Gly Lys Tyr Thr Ala Gln Gly Asp Arg His Val Ala Tyr Ile Ile Arg Ser His Val Lys Asp His Tyr Ile Phe Tyr Ser Glu Gly Asn Leu Gln Gly Glu Thr Val Pro Gly Val Trp Leu Val Gly Arg Asp Pro Lys Asn Asn Leu Glu Ala Leu Glu Asp Phe Glu Lys Ala Ala Gly Ala Arg Gly Leu Ser Thr Glu Ser Ile Leu Ile Pro Arg Gln Ser Glu Thr Ser Ser Pro Gly |
| 18 | DS-001 | Ala Ser Asp Glu Glu Ile Gln Asp Val Ser Gly Thr Trp Tyr Leu Lys Ala Met Thr Val Asp Arg Phe Lys Ile Ala Ser Trp Pro Arg Ser Val Thr Pro Met Thr Leu Thr Thr Leu Glu Gly Gly Asn Leu Glu Ala Lys Val Thr Met Asn Trp Trp Gly Arg Ser Gln Gln Val Lys Ala Val Leu Glu Arg Thr Asp Glu Pro Gly Lys Tyr Thr Ala Gln Gly Asp Arg His Val Ala Tyr Ile Ile Arg Ser Pro Val Lys Asp His Tyr Ile Phe Tyr Ser Glu Gly Asn Leu Gln Gly Glu Thr Val Pro Gly Val Trp Leu Val Gly Arg Asp Pro Lys Asn Asn Leu Glu Ala Leu Glu Asp Phe Glu Lys Ala Ala Gly Ala Arg Gly Leu Ser Thr Glu Ser Ile Leu Ile Pro Arg Gln Ser Glu Thr Ser Ser Pro Gly Gly Gly Ser Leu Ala Glu Ala Lys Glu Ala Ala Asn Ala Glu Leu Asp Ser Tyr Gly Val Ser Asp Phe Tyr Lys Arg Leu Ile Asp Lys Ala Lys Thr Val Glu Gly Val Glu Ala Leu Lys Asp Ala Ile Leu Ala Ala Leu Pro Gly |

TABLE 2-continued

| SEQ ID NO. | Description | Sequence |
|---|---|---|
| 19 | DS-001 | Gly Ala Ser Asp Glu Glu Ile Gln Asp Val Ser Gly Thr Trp Tyr Leu Lys Ala Met Thr Val Asp Arg Phe Lys Ile Ala Ser Trp Pro Arg Ser Val Thr Pro Met Thr Leu Thr Thr Leu Glu Gly Gly Asn Leu Glu Ala Lys Val Thr Met Asn Trp Trp Gly Arg Ser Gln Glu Val Lys Ala Val Leu Glu Arg Thr Asp Gly Pro Gly Lys Tyr Thr Ala Gln Gly Asp Arg His Val Ala Tyr Ile Ile Arg Ser His Val Lys Asp His Tyr Ile Phe Tyr Ser Glu Gly Asn Leu Gln Gly Glu Thr Val Pro Gly Val Trp Leu Val Gly Arg Asp Pro Lys Asn Asn Leu Glu Ala Leu Glu Asp Phe Glu Lys Ala Ala Gly Ala Arg Gly Leu Ser Thr Glu Ser Ile Leu Ile Pro Arg Gln Ser Glu Thr Ser Ser Pro Gly Lys Leu Gly Gly Gly Ser Leu Ala Glu Ala Lys Glu Ala Ala Asn Ala Glu Leu Asp Ser Tyr Gly Val Ser Asp Phe Tyr Lys Arg Leu Ile Asp Lys Ala Lys Thr Val Glu Gly Val Glu Ala Leu Lys Asp Ala Ile Leu Ala Ala Leu Pro Gly Lys Leu Asn |
| 20 | CA-001 | Met Gly Arg Gln Leu Ala Gly Cys Gly Asp Ala Gly Lys Lys Ala Ser Phe Lys Met Ser Thr Val His Glu Ile Leu Cys Lys Leu Ser Leu Glu Gly Asp His Ser Thr Pro Pro Ser Ala Tyr Gly Ser Val Lys Ala Tyr Thr Asn Phe Asp Ala Glu Arg Asp Ala Leu Asn Ile Glu Thr Ala Ile Lys Thr Lys Gly Val Asp Glu Val Thr Ile Val Asn Ile Leu Thr Asn Arg Ser Asn Ala Gln Arg Gln Asp Ile Ala Phe Ala Tyr Gln Arg Arg Thr Lys Lys Glu Leu Ala Ser Ala Leu Lys Ser Ala Leu Ser Gly His Leu Glu Thr Val Ile Leu Gly Leu Leu Lys Thr Pro Ala Gln Tyr Asp Ala Ser Glu Leu Lys Ala Ser Met Lys Gly Leu Gly Thr Asp Glu Asp Ser Leu Ile Glu Ile Ile Cys Ser Arg Thr Asn Gln Glu Leu Gln Glu Ile Asn Arg Val Tyr Lys Glu Met Tyr Lys Thr Asp Leu Glu Lys Asp Ile Ile Ser Asp Thr Ser Gly Asp Phe Arg Lys Leu Met Val Ala Leu Ala Lys Gly Arg Arg Ala Glu Asp Gly Ser Val Ile Asp Tyr Glu Leu Ile Asp Gln Asp Ala Arg Asp Leu Tyr Asp Ala Gly Val Lys Arg Lys Gly Thr Asp Val Pro Lys Trp Ile Ser Ile Met Thr Glu Arg Ser Val Pro His Leu Gln Lys Val Phe Asp Arg Tyr Lys Ser Tyr Ser Pro Tyr Asp Met Leu Glu Ser Ile Arg Lys Glu Val Lys Gly Asp Leu Glu Asn Ala Phe Leu Asn Leu Val Gln Cys Ile Gln Asn Lys Pro Leu Tyr Phe Ala Asp Arg Leu Tyr Asp Ser Met Lys Gly Lys Gly Thr Arg Asp Lys Val Leu Ile Arg Ile Met Val Ser Arg Ser Glu Val Asp Met Leu Lys Ile Arg Ser Glu Phe Lys Arg Lys Tyr Gly Lys Ser Leu Tyr Tyr Tyr Ile Gln Gln Asp Thr Lys Gly Asp Tyr Gln Lys Ala Leu Leu Tyr Leu Cys Gly Gly Asp Asp |
| 21 | CA-001 | Met Ser Thr Val His Glu Ile Leu Cys Lys Leu Ser Leu Glu Gly Asp His Ser Thr Pro Pro Ser Ala Tyr Gly Ser Val Lys Ala Tyr Thr Asn Phe Asp Ala Glu Arg Asp Ala Leu Asn Ile Glu Thr Ala Ile Lys Thr Lys Gly Val Asp Glu Val Thr Ile Val Asn Ile Leu Thr Asn Arg Ser Asn Ala Gln Arg Gln Asp Ile Ala Phe Ala Tyr Gln Arg Arg Thr Lys Lys Glu Leu Ala Ser Ala Leu Lys Ser Ala Leu Ser Gly His Leu Glu Thr Val Ile Leu Gly Leu Leu Lys Thr Pro Ala Gln Tyr Asp Ala Ser Glu Leu Lys Ala Ser Met Lys Gly Leu Gly Thr Asp Glu Asp Ser Leu Ile Glu Ile Ile Cys Ser Arg Thr Asn Gln Glu Leu Gln Glu Ile Asn Arg Val Tyr Lys Glu Met Tyr Lys Thr Asp Leu Glu Lys Asp Ile Ile Ser Asp Thr Ser Gly Asp Phe Arg Lys Leu Met Val Ala Leu Ala Lys Gly Arg Arg Ala Glu Asp Gly Ser Val Ile Asp Tyr Glu Leu Ile Asp Gln Asp Ala Arg Asp Leu Tyr Asp Ala Gly Val Lys Arg Lys Gly Thr Asp Val Pro Lys Trp Ile Ser Ile Met Thr Glu Arg Ser Val Pro His Leu Gln Lys Val Phe Asp Arg Tyr Lys Ser Tyr Ser Pro Tyr Asp Met Leu Glu Ser Ile Arg Lys Glu Val Lys Gly Asp Leu Glu Asn Ala Phe Leu Asn Leu Val Gln Cys Ile Gln Asn Lys Pro Leu Tyr Phe Ala Asp Arg Leu Tyr Asp Ser Met Lys Gly Lys Gly Thr Arg Asp Lys Val Leu Ile Arg Ile Met Val Ser Arg Ser Glu Val Asp Met Leu Lys Ile Arg Ser Glu Phe Lys Arg Lys Tyr Gly Lys Ser Leu Tyr Tyr Tyr Ile Gln Gln Asp Thr Lys Gly Asp Tyr Gln Lys Ala Leu Leu Tyr Leu Cys Gly Gly Asp Asp |
| 22 | MS-001 | Met Glu Lys Met Leu Ala Gly Cys Phe Leu Leu Ile Leu Gly Gln Ile Val Leu Leu Pro Ala Glu Ala Arg Glu Arg Ser Arg Gly Arg Ser Ile Ser Arg Gly Arg His Ala Arg Thr His Pro Gln Thr Ala Leu Leu Glu Ser Ser Cys Glu Asn Lys Arg Ala Asp Leu Val Phe Ile Ile Asp Ser Ser Arg Ser Val Asn Thr His Asp Tyr Ala Lys Val Lys Glu Phe Ile Val Asp Ile Leu Gln Phe Leu Asp Ile Gly Pro Asp Val Thr Arg Val Gly Leu Leu Gln Tyr Gly Ser Thr Val Lys Asn Glu Phe Ser Leu Lys Thr Phe Lys Ser Glu Val Glu Arg Ala Val Lys Arg Met Arg His Leu Ser Thr Gly Thr Met Thr Gly Leu Ala Ile Gln Tyr Ala Leu Asn Ile Ala Phe Ser Glu Ala Glu Gly Ala Arg Pro Leu Arg Glu Asn Val Pro Arg Val Ile Met Ile Val Thr Asp Gly Arg Pro Gln Asp Ser Val Ala Glu Val Ala Ala Lys Ala Arg Asp Thr Gly Ile Leu Ile Phe Ala Ile Gly Val Gly Gln Val Asp Phe |

TABLE 2-continued

| SEQ ID NO. | Description | Sequence |
|---|---|---|
| | | Asn Thr Leu Lys Ser Ile Gly Ser Glu Pro His Glu Asp His Val
Phe Leu Val Ala Asn Phe Ser Gln Ile Glu Thr Leu Thr Ser Val
Phe Gln Lys Lys Leu Cys Ile Asn Ile Met Cys Ser Thr Leu Glu
His Asn Cys Ala His Phe Cys Ile Asn Ile Pro Gly Ser Tyr Val Cys
Arg Cys Lys Gln Gly Tyr Ile Leu Asn Ser Asp Gln Thr Thr Cys
Arg Ile Gln Asp Leu Cys Ala Met Glu Asp His Asn Cys Glu Gln
Leu Cys Val Asn Val Pro Gly Ser Phe Val Cys Gln Cys Tyr Ser
Gly Tyr Ala Leu Ala Glu Asp Gly Lys Arg Cys Val Ala Val Asp
Tyr Cys Ala Ser Glu Asn His Gly Cys Glu His Glu Cys Val Asn
Ala Asp Gly Ser Tyr Leu Cys Gln Cys His Glu Gly Phe Ala Leu
Asn Pro Asp Lys Lys Thr Cys Thr Lys Ile Asp Tyr Cys Ala Ser
Ser Asn His Gly Cys Gln His Glu Cys Val Asn Thr Asp Asp Ser
Tyr Ser Cys His Cys Leu Lys Gly Phe Thr Leu Asn Pro Asp Lys
Lys Thr Cys Arg Arg Ile Asn Tyr Cys Ala Leu Asn Lys Pro Gly
Cys Glu His Glu Cys Val Asn Met Glu Glu Ser Tyr Tyr Cys Arg
Cys His Arg Gly Tyr Thr Leu Asp Pro Asn Gly Lys Thr Cys Ser
Arg Val Asp His Cys Ala Gln Gln Asp His Gly Cys Glu Gln Leu
Cys Leu Asn Thr Glu Asp Ser Phe Val Cys Gln Cys Ser Glu Gly
Phe Leu Ile Asn Glu Asp Leu Lys Tyr Cys Ser Arg Val Asp Tyr
Cys Leu Leu Ser Asp His Gly Cys Glu Tyr Ser Cys Val Asn Met
Asp Arg Ser Phe Ala Cys Gln Cys Pro Glu Gly His Val Leu Arg
Ser Asp Gly Lys Thr Cys Ala Lys Leu Asp Ser Cys Ala Leu Gly
Asp His Gly Cys Glu His Ser Cys Val Ser Ser Glu Asp Ser Phe
Val Cys Gln Cys Phe Glu Gly Tyr Ile Leu Arg Glu Asp Gly Lys
Thr Cys Arg Arg Lys Asp Val Cys Gln Ala Ile Asp His Gly Cys
Glu His Ile Cys Val Asn Ser Asp Asp Ser Tyr Thr Cys Glu Cys
Leu Glu Gly Phe Arg Leu Ala Glu Asp Gly Lys Arg Cys Arg Arg
Lys Asp Val Cys Lys Ser Thr His His Gly Cys Glu His Ile Cys
Val Asn Asn Gly Asn Ser Tyr Ile Cys Lys Cys Ser Glu Gly Phe
Val Leu Ala Glu Asp Gly Arg Arg Cys Lys Lys Cys Thr Glu Gly
Pro Ile Asp Leu Val Phe Val Ile Asp Gly Ser Lys Ser Leu Gly Glu
Glu Asn Phe Glu Val Val Lys Gln Phe Val Thr Gly Ile Ile Asp Ser
Leu Thr Ile Ser Pro Lys Ala Ala Arg Val Gly Leu Leu Gln Tyr Ser
Thr Gln Val His Thr Glu Phe Thr Leu Arg Asn Phe Asn Ser Ala
Lys Asp Met Lys Lys Ala Val Ala His Met Lys Tyr Met Gly Lys
Gly Ser Met Thr Gly Leu Ala Leu Lys His Met Phe Glu Arg Ser
Phe Thr Gln Gly Glu Gly Ala Arg Pro Leu Ser Thr Arg Val Pro
Arg Ala Ala Ile Val Phe Thr Asp Gly Arg Ala Gln Asp Asp Val
Ser Glu Trp Ala Ser Lys Ala Lys Ala Asn Gly Ile Thr Met Tyr Ala
Val Gly Val Gly Lys Ala Ile Glu Glu Glu Leu Gln Glu Ile Ala Ser
Glu Pro Thr Asn Lys His Leu Phe Tyr Ala Glu Asp Phe Ser Thr
Met Asp Glu Ile Ser Glu Lys Leu Lys Lys Gly Ile Cys Glu Ala
Leu Glu Asp Ser Asp Gly Arg Gln Asp Ser Pro Ala Gly Glu Leu
Pro Lys Thr Val Gln Gln Pro Thr Glu Ser Glu Pro Val Thr Ile Asn
Ile Gln Asp Leu Leu Ser Cys Ser Asn Phe Ala Val Gln His Arg
Tyr Leu Phe Glu Glu Asp Asn Leu Leu Arg Ser Thr Gln Lys Leu
Ser His Ser Thr Lys Pro Ser Gly Ser Pro Leu Glu Glu Lys His
Asp Gln Cys Lys Cys Glu Asn Leu Ile Met Phe Gln Asn Leu Ala
Asn Glu Glu Val Arg Lys Leu Thr Gln Arg Leu Glu Glu Met Thr
Gln Arg Met Glu Ala Leu Glu Asn Arg Leu Arg Tyr Arg |
| 23 | MS-001 | Met Glu Lys Met Leu Ala Gly Cys Phe Leu Leu Ile Leu Gly Gln
Ile Val Leu Leu Pro Ala Glu Ala Arg Glu Arg Ser Arg Gly Arg
Ser Ile Ser Arg Gly Arg His Ala Arg Thr His Pro Gln Thr Ala Leu
Leu Glu Ser Ser Cys Glu Asn Lys Arg Ala Asp Leu Val Phe Ile Ile
Asp Ser Ser Arg Ser Val Asn Thr His Asp Tyr Ala Lys Val Lys
Glu Phe Ile Val Asp Ile Leu Gln Phe Leu Asp Ile Gly Pro Asp Val
Thr Arg Val Gly Leu Leu Gln Tyr Gly Ser Thr Val Lys Asn Glu
Phe Ser Leu Lys Thr Phe Lys Arg Lys Ser Glu Val Glu Arg Ala
Val Lys Arg Met Arg His Leu Ser Thr Gly Thr Met Thr Gly Leu
Ala Ile Gln Tyr Ala Leu Asn Ile Ala Phe Ser Glu Ala Glu Gly Ala
Arg Pro Leu Arg Glu Asn Val Pro Arg Val Ile Met Ile Val Thr Asp
Gly Arg Pro Gln Asp Ser Val Ala Glu Val Ala Ala Lys Ala Arg
Asp Thr Gly Ile Leu Ile Phe Ala Ile Gly Val Gly Gln Val Asp Phe
Asn Thr Leu Lys Ser Ile Gly Ser Glu Pro His Glu Asp His Val
Phe Leu Val Ala Asn Phe Ser Gln Ile Glu Thr Leu Thr Ser Val
Phe Gln Lys Lys Leu Cys Thr Ala His Met Cys Ser Thr Leu Glu
His Asn Cys Ala His Phe Cys Ile Asn Ile Pro Gly Ser Tyr Val Cys
Arg Cys Lys Gln Gly Tyr Ile Leu Asn Ser Asp Gln Thr Thr Cys
Arg Ile Gln Asp Leu Cys Ala Met Glu Asp His Asn Cys Glu Gln
Leu Cys Val Asn Val Pro Gly Ser Phe Val Cys Gln Cys Tyr Ser
Gly Tyr Ala Leu Ala Glu Asp Gly Lys Arg Cys Val Ala Val Asp
Tyr Cys Ala Ser Glu Asn His Gly Cys Glu His Glu Cys Val Asn
Ala Asp Gly Ser Tyr Leu Cys Gln Cys His Glu Gly Phe Ala Leu
Asn Pro Asp Lys Lys Thr Cys Thr Lys Ile Asp Tyr Cys Ala Ser
Ser Asn His Gly Cys Gln His Glu Cys Val Asn Thr Asp Asp Ser
Tyr Ser Cys His Cys Leu Lys Gly Phe Thr Leu Asn Pro Asp Lys |

TABLE 2-continued

| SEQ ID NO. | Description | Sequence |
|---|---|---|
| | | Lys Thr Cys Arg Arg Ile Asn Tyr Cys Ala Leu Asn Lys Pro Gly<br>Cys Glu His Glu Cys Val Asn Met Glu Glu Ser Tyr Tyr Cys Arg<br>Cys His Arg Gly Tyr Thr Leu Asp Pro Asn Gly Lys Thr Cys Ser<br>Arg Val Asp His Cys Ala Glu Glu Asp His Gly Cys Glu Gln Leu<br>Cys Leu Asn Thr Glu Asp Ser Phe Val Cys Gln Cys Ser Glu Gly<br>Phe Leu Ile Asn Glu Asp Leu Lys Thr Cys Ser Arg Val Asp Tyr<br>Cys Leu Leu Ser Asp His Gly Cys Glu Tyr Ser Cys Val Asn Met<br>Asp Arg Ser Phe Ala Cys Gln Cys Pro Glu Gly His Val Leu Arg<br>Ser Asp Gly Lys Thr Cys Ala Lys Leu Asp Ser Cys Ala Leu Gly<br>Asp His Gly Cys Glu His Ser Cys Val Ser Ser Glu Asp Ser Phe<br>Val Cys Gln Cys Phe Glu Gly Tyr Ile Leu Arg Glu Asp Gly Lys<br>Thr Cys Arg Arg Lys Asp Val Cys Gln Ala Ile Asp His Gly Cys<br>Glu His Ile Cys Val Asn Ser Asp Asp Ser Tyr Thr Cys Glu Cys<br>Leu Glu Gly Phe Arg Leu Ala Glu Asp Gly Lys Arg Cys Arg Arg<br>Lys Asp Val Cys Lys Ser Thr His His Gly Cys Glu His Ile Cys<br>Val Asn Asn Gly Asn Ser Tyr Ile Cys Lys Cys Ser Glu Gly Phe<br>Val Leu Ala Glu Asp Gly Arg Arg Cys Lys Lys Cys Thr Glu Gly<br>Pro Ile Asp Leu Val Phe Val Ile Asp Gly Ser Lys Ser Leu Gly Glu<br>Glu Asn Phe Glu Val Val Lys Gln Phe Val Thr Gly Ile Ile Asp Ser<br>Leu Thr Ile Ser Pro Lys Ala Ala Arg Val Gly Leu Leu Gln Tyr Ser<br>Thr Gln Val His Thr Glu Phe Thr Leu Arg Asn Phe Asn Ser Ala<br>Lys Asp Met Lys Lys Ala Val Ala His Met Lys Tyr Met Gly Lys<br>Gly Ser Met Thr Gly Leu Ala Leu Lys His Met Phe Glu Arg Ser<br>Phe Thr Gln Gly Glu Gly Ala Arg Pro Leu Ser Thr Arg Val Pro<br>Arg Ala Ala Ile Val Phe Thr Asp Gly Arg Ala Gln Asp Asp Val<br>Ser Glu Trp Ala Ser Lys Ala Lys Ala Asn Gly Ile Thr Met Tyr Ala<br>Val Gly Val Gly Lys Ala Ile Glu Glu Leu Gln Glu Ile Ala Ser<br>Glu Pro Thr Asn Lys His Leu Phe Tyr Ala Glu Asp Phe Ser Thr<br>Met Asp Glu Ile Ser Glu Lys Leu Lys Lys Gly Ile Cys Glu Ala<br>Leu Glu Asp Ser Asp Gly Arg Gln Asp Ser Pro Ala Gly Glu Leu<br>Pro Lys Thr Val Gln Gln Pro Thr Val Gln His Arg Tyr Leu Phe<br>Glu Glu Asp Asn Leu Leu Arg Ser Thr Gln Lys Leu Ser His Ser<br>Thr Lys Pro Ser Gly Ser Pro Leu Glu Glu Lys His Asp Gln Cys<br>Lys Cys Glu Asn Leu Ile Met Phe Gln Asn Leu Ala Asn Glu Glu<br>Val Arg Lys Leu Thr Gln Arg Leu Glu Glu Met Thr Gln Arg Met<br>Glu Ala Leu Glu Asn Arg Leu Arg Tyr Arg |
| 24 | MS-001 variable zone in heavy chain | Gln Val Gln Leu Val Gln Ser Gly Ala Glu Val Lys Lys Pro Gly<br>Glu Ser Leu Lys Ile Ser Cys Lys Gly Ser Gly Tyr Ser Phe Thr<br>Asn Tyr Trp Ile Ser Trp Val Arg Gln Met Pro Gly Lys Gly Leu<br>Glu Trp Met Gly Ile Ile Tyr Pro Gly Asp Ser Tyr Thr Asn Tyr Ser<br>Pro Ser Phe Gln Gly Gln Val Thr Ile Ser Ala Asp Lys Ser Ile Ser<br>Thr Ala Tyr Leu Gln Trp Ser Ser Leu Lys Ala Ser Asp Thr Ala<br>Met Tyr Tyr Cys Ala Arg Asp Tyr Trp Tyr Lys Pro Leu Phe Asp<br>Ile Trp Gly Gln Gly Thr Leu Val Thr Val Ser Ser |
| 25 | MS-001 variable zone in light chain | Asp Ile Val Met Thr Gln Ser Pro Asp Ser Leu Ala Val Ser Leu<br>Gly Glu Arg Ala Thr Ile Asn Cys Arg Ser Ser Gln Ser Val Leu Tyr<br>Ser Ser Asn Asn Lys Asn Tyr Leu Ala Trp Tyr Gln Gln Lys Pro<br>Gly Gln Pro Pro Lys Leu Leu Ile Tyr Trp Ala Ser Thr Arg Glu Ser<br>Gly Val Pro Asp Arg Phe Ser Gly Ser Gly Ser Gly Thr Asp Phe<br>Thr Leu Thr Ile Ser Ser Leu Gln Ala Glu Asp Val Ala Val Tyr Tyr<br>Cys Gln Gln Tyr Ser Ser Phe Pro Ile Thr Phe Gly Gln Gly Thr<br>Lys Val Glu Ile Lys Arg |
| 26 | MS-001 variable zone in heavy chain | Glu Val Gln Leu Leu Glu Ser Gly Gly Gly Leu Val Gln Pro Gly<br>Gly Ser Leu Arg Leu Ser Cys Lys Ala Ser Gly Tyr Thr Phe Ser<br>Ser Tyr Gly Met Tyr Trp Val Arg Gln Ala Pro Gly Lys Gly Leu<br>Glu Trp Ile Gly Trp Ile Asp Pro Gly Ser Gly Gly Thr Lys Tyr Asn<br>Glu Lys Phe Lys Gly Lys Ala Thr Ile Ser Arg Asp Asn Ser Lys<br>Asn Thr Leu Tyr Leu Gln Met Asn Ser Leu Arg Ala Glu Asp Thr<br>Ala Val Tyr Tyr Cys Ala Arg Glu Arg Tyr Gly Tyr Tyr Phe Asp<br>Tyr Trp Gly Gln Gly Thr Leu Val Thr Val Ser Ser Ala Ser |
| 27 | MS-001 variable zone in heavy chain | Glu Val Gln Leu Leu Glu Ser Gly Gly Gly Leu Val Gln Pro Gly<br>Gly Ser Leu Arg Leu Ser Cys Lys Ala Ser Gly Tyr Thr Phe Ser<br>Ser Tyr Gly Met Tyr Trp Val Arg Gln Ala Pro Gly Lys Gly Leu<br>Glu Trp Ile Gly Trp Ile Asp Pro Gly Ser Gly Gly Thr Lys Tyr Asn<br>Glu Lys Phe Lys Gly Lys Ala Thr Ile Ser Arg Asp Asn Ser Lys<br>Asn Thr Leu Tyr Leu Gln Met Asn Ser Leu Arg Ala Glu Asp Thr<br>Ala Val Tyr Tyr Cys Ala Arg Glu Arg Tyr Gly Tyr Tyr Phe Asp<br>Tyr Trp Gly Gln Gly Thr Leu Val Thr Val Ser Ser |
| 28 | MS-001 variable zone in light chain | Glu Ile Val Leu Thr Gln Ser Pro Ala Thr Leu Ser Leu Ser Pro Gly<br>Glu Arg Ala Thr Ile Thr Cys Arg Ala Ser Gln Tyr Val Gly Ser Tyr<br>Leu Asn Trp Tyr Gln Gln Lys Pro Gly Gln Ala Pro Arg Leu Leu<br>Ile Tyr Asp Ala Ser Asn Arg Ala Thr Gly Ile Pro Ala Arg Phe Ser |

TABLE 2-continued

| SEQ ID NO. | Description | Sequence |
|---|---|---|
| | | Gly Ser Gly Ser Gly Thr Asp Phe Thr Leu Thr Ile Ser Ser Leu<br>Glu Pro Glu Asp Phe Ala Val Tyr Tyr Cys Gln Val Trp Asp Ser<br>Ser Pro Pro Val Val Phe Gly Gly Gly Thr Lys Val Glu Ile Lys |
| 29 | MS-001 variable zone in heavy chain | Glu Val Gln Leu Leu Glu Ser Gly Gly Gly Leu Val Gln Pro Gly<br>Gly Ser Leu Arg Leu Ser Cys Lys Ala Ser Gly Phe Thr Phe Thr<br>Ser Tyr Tyr Met His Trp Val Arg Gln Ala Pro Gly Lys Gly Leu<br>Glu Trp Ile Gly Arg Ile Asn Pro Asp Ser Gly Ser Thr Lys Tyr Asn<br>Glu Lys Phe Lys Gly Arg Ala Thr Ile Ser Arg Asp Asn Ser Lys<br>Asn Thr Leu Tyr Leu Gln Met Asn Ser Leu Arg Ala Glu Asp Thr<br>Ala Val Tyr Tyr Cys Ala Arg Gly Gly Arg Leu Ser Trp Asp Phe<br>Asp Val Trp Gly Gln Gly Thr Leu Val Thr Val Ser Ser |
| 30 | MS-001 variable zone in light chain | Asp Ile Gln Met Thr Gln Ser Pro Ser Ser Leu Ser Ala Ser Val Gly<br>Asp Arg Val Thr Ile Thr Cys Arg Ala Ser Gln Asp Ile Ser Arg Tyr<br>Leu Ala Trp Tyr Gln Gln Lys Pro Gly Lys Ala Pro Lys Leu Leu<br>Ile Tyr Ala Ala Ser Ser Leu Gln Ser Gly Val Pro Ser Arg Phe Ser<br>Gly Ser Gly Ser Gly Thr Asp Phe Thr Leu Thr Ile Ser Ser Leu<br>Gln Pro Glu Asp Phe Ala Thr Tyr Tyr Cys Ala Ala Tyr Asp Tyr<br>Ser Leu Gly Gly Tyr Val Phe Gly Asp Gly Thr Lys Val Glu Ile<br>Lys |
| 31 | MS-001 variable zone in light chain | Asp Ile Gln Met Thr Gln Ser Pro Ser Ser Leu Ser Ala Ser Val Gly<br>Asp Arg Val Thr Ile Thr Cys Arg Ala Ser Gln Asp Ile Ser Arg Tyr<br>Leu Ala Trp Tyr Gln Gln Lys Pro Gly Lys Ala Pro Lys Leu Leu<br>Ile Tyr Ala Ala Ser Ser Leu Gln Ser Gly Val Pro Ser Arg Phe Ser<br>Gly Ser Gly Ser Gly Thr Asp Phe Thr Leu Thr Ile Ser Ser Leu<br>Gln Pro Glu Asp Phe Ala Thr Tyr Tyr Cys Ala Ala Tyr Asp Tyr<br>Ser Leu Gly Gly Tyr Val Phe Gly Gly Gly Thr Lys Val Glu Ile<br>Lys |
| 32 | MS-001 variable zone in heavy chain | Gln Val Gln Leu Val Gln Ser Gly Ala Glu Val Lys Lys Pro Gly<br>Ser Ser Val Lys Val Ser Cys Lys Ala Ser Gly Gly Thr Phe Asn Ser<br>His Ala Ile Ser Trp Val Arg Gln Ala Pro Gly Gln Gly Leu Glu Trp<br>Met Gly Gly Ile Asn Pro Ile Leu Gly Ile Ala Asn Tyr Ala Gln Lys<br>Phe Gln Gly Arg Val Thr Ile Thr Ala Asp Glu Ser Thr Ser Thr Ala<br>Tyr Met Glu Leu Ser Ser Leu Arg Ser Glu Asp Thr Ala Val Tyr<br>Tyr Cys Ala Arg His Tyr Glu Ile Gln Ile Gly Arg Tyr Gly Met Asn<br>Val Tyr Tyr Leu Met Tyr Arg Phe Ala Ser Trp Gly Gln Gly Thr<br>Leu Val Thr Val Ser Ser |
| 33 | MS-001 variable zone in light chain | Asp Ile Gln Met Thr Gln Ser Pro Ser Ser Leu Ser Ala Ser Val Gly<br>Asp Arg Val Thr Ile Thr Cys Arg Ala Ser Gln Ile Ile Arg Ser Ala<br>Leu Asn Trp Tyr Gln Gln Lys Pro Gly Lys Ala Pro Lys Leu Leu<br>Ile Tyr Asn Gly Ser Thr Leu Gln Ser Gly Val Pro Ser Arg Phe Ser<br>Gly Ser Gly Ser Gly Thr Asp Phe Thr Leu Thr Ile Ser Ser Leu<br>Gln Pro Glu Asp Phe Ala Val Tyr Tyr Cys Gln Gln Phe Asp Gly<br>Asp Pro Thr Phe Gly Gln Gly Thr Lys Val Glu Ile Lys Arg |
| 34 | LY3015014 Heavy chain | Glu Val Gln Leu Val Glu Ser Gly Gly Gly Leu Val Lys Pro Gly<br>Gly Ser Leu Arg Leu Ser Cys Ala Ala Ser Gly Phe Pro Phe Ser<br>Lys Leu Gly Met Val Trp Val Arg Gln Ala Pro Gly Lys Gly Leu<br>Glu Trp Val Ser Thr Ile Ser Gly Gly Gly Tyr Thr Tyr Tyr Pro<br>Asp Ser Val Lys Gly Arg Phe Thr Ile Ser Arg Asp Asn Ala Lys<br>Asn Ser Leu Tyr Leu Gln Met Asn Ser Leu Arg Ala Glu Asp Thr<br>Ala Val Tyr Tyr Cys Ala Arg Glu Gly Ile Ser Phe Gln Gly Gly Thr<br>Tyr Thr Tyr Val Met Asp Tyr Trp Gly Gln Gly Thr Leu Val Thr<br>Val Ser Ser Ala Ser Thr Lys Gly Pro Ser Val Phe Pro Leu Ala Pro<br>Cys Ser Arg Ser Thr Ser Glu Ser Thr Ala Ala Leu Gly Cys Leu<br>Val Lys Asp Tyr Phe Pro Glu Pro Val Thr Val Ser Trp Asn Ser Gly<br>Ala Leu Thr Ser Gly Val His Thr Phe Pro Ala Val Leu Gln Ser Ser<br>Gly Leu Tyr Ser Leu Ser Ser Val Val Thr Val Pro Ser Ser Ser Leu<br>Gly Thr Lys Thr Tyr Thr Cys Asn Val Asp His Lys Pro Ser Asn<br>Thr Lys Val Asp Lys Arg Val Glu Ser Lys Tyr Gly Pro Pro Cys<br>Pro Pro Cys Pro Ala Pro Glu Ala Ala Gly Gly Pro Ser Val Phe<br>Leu Phe Pro Pro Lys Pro Lys Asp Thr Leu Met Ile Ser Arg Thr<br>Pro Glu Val Thr Cys Val Val Val Asp Val Ser Gln Glu Asp Pro<br>Glu Val Gln Phe Asn Trp Tyr Val Asp Gly Val Glu Val His Asn<br>Ala Lys Thr Lys Pro Arg Glu Glu Gln Phe Asn Ser Thr Tyr Arg<br>Val Val Ser Val Leu Thr Val Leu His Gln Asp Trp Leu Asn Gly<br>Lys Glu Tyr Lys Cys Lys Val Ser Asn Lys Gly Leu Pro Ser Ser Ile<br>Glu Lys Thr Ile Ser Lys Ala Lys Gly Gln Pro Arg Glu Pro Gln Val<br>Tyr Thr Leu Pro Pro Ser Gln Glu Glu Met Thr Lys Asn Gln Val<br>Ser Leu Thr Cys Leu Val Lys Gly Phe Tyr Pro Ser Asp Ile Ala Val<br>Glu Trp Glu Ser Asn Gly Gln Pro Glu Asn Asn Tyr Lys Thr Thr<br>Pro Pro Val Leu Asp Ser Asp Gly Ser Phe Phe Leu Tyr Ser Arg<br>Leu Thr Val Asp Lys Ser Arg Trp Gln Glu Gly Asn Val Phe Ser |

TABLE 2-continued

| SEQ ID NO. | Description | Sequence |
|---|---|---|
| | | Cys Ser Val Met His Glu Ala Leu His Asn His Tyr Thr Gln Lys Ser Leu Ser Leu Ser Leu Gly |
| 35 | LY3015014 Light chain | Asp Ile Val Met Thr Gln Ser Pro Leu Ser Leu Pro Val Thr Pro Gly Glu Pro Ala Ser Ile Ser Cys Arg Ser Ser Lys Ser Leu Leu His Arg Asn Gly Ile Thr Tyr Ser Tyr Trp Tyr Leu Gln Lys Pro Gly Gln Ser Pro Gln Leu Leu Ile Tyr Gln Leu Ser Asn Leu Ala Ser Gly Val Pro Asp Arg Phe Ser Gly Ser Gly Ser Gly Thr Asp Phe Thr Leu Lys Ile Ser Arg Val Glu Ala Glu Asp Val Gly Val Tyr Tyr Cys Tyr Gln Asn Leu Glu Leu Pro Leu Thr Phe Gly Gln Gly Thr Lys Val Glu Ile Lys Arg Thr Val Ala Ala Pro Ser Val Phe Ile Phe Pro Pro Ser Asp Glu Gln Leu Lys Ser Gly Thr Ala Ser Val Val Cys Leu Leu Asn Asn Phe Tyr Pro Arg Glu Ala Lys Val Gln Trp Lys Val Asp Asn Ala Leu Gln Ser Gly Asn Ser Gln Glu Ser Val Thr Glu Gln Asp Ser Lys Asp Ser Thr Tyr Ser Leu Ser Ser Thr Leu Thr Leu Ser Lys Ala Asp Tyr Glu Lys His Lys Val Tyr Ala Cys Glu Val Thr His Gln Gly Leu Ser Ser Pro Val Thr Lys Ser Phe Asn Arg Gly Glu Cys |
| 36 | NS-001 variable zone in heavy chain | Gln Val Gln Leu Val Gln Ser Gly Ala Glu Val Lys Lys Pro Gly Ala Ser Val Lys Val Ser Cys Lys Ala Ser Gly Tyr Thr Phe Ser Thr Met Tyr Met Ser Trp Val Arg Gln Ala Pro Gly Gln Gly Leu Glu Trp Met Gly Arg Ile Asp Pro Ala Asn Glu His Thr Asn Tyr Ala Gln Lys Phe Gln Gly Arg Val Thr Met Thr Arg Asp Thr Ser Ile Ser Thr Ala Tyr Met Glu Leu Ser Arg Leu Thr Ser Asp Asp Thr Ala Val Tyr Tyr Cys Ala Arg Ser Tyr Tyr Tyr Asn Met Asp Tyr Trp Gly Gln Gly Thr Leu Val Thr Val Ser Ser |
| 37 | NS-001 variable zone in light chain | Gln Ile Val Leu Thr Gln Ser Pro Ala Thr Leu Ser Val Ser Pro Gly Glu Arg Ala Thr Leu Ser Cys Arg Ala Ser Gln Ser Val Ser Tyr Met His Trp Tyr Gln Gln Lys Pro Gly Gln Ala Pro Arg Leu Leu Ile Tyr Gly Val Phe Arg Arg Ala Thr Gly Ile Pro Asp Arg Phe Ser Gly Ser Gly Ser Gly Thr Asp Phe Thr Leu Thr Ile Gly Arg Leu Glu Pro Glu Asp Phe Ala Val Tyr Tyr Cys Leu Gln Trp Ser Ser Asp Pro Pro Thr Phe Gly Gln Gly Thr Lys Leu Glu Ile Lys |
| 38 | NS-001 variable zone in heavy chain | Gln Val Gln Leu Val Gln Ser Gly Ala Glu Val Lys Lys Pro Gly Ala Ser Val Lys Val Ser Cys Lys Ala Ser Gly Tyr Thr Phe Ser Thr Met Tyr Met Ser Trp Val Arg Gln Ala Pro Gly Gln Gly Leu Glu Trp Met Gly Arg Ile Asp Pro Ala Asn Glu His Thr Asn Tyr Ala Gln Lys Phe Gln Gly Arg Val Thr Met Thr Arg Asp Thr Ser Ile Ser Thr Ala Tyr Met Glu Leu Ser Arg Leu Thr Ser Asp Asp Thr Ala Val Tyr Tyr Cys Ala Arg Ser Tyr Tyr Tyr Asn Met Asp Tyr Trp Gly Gln Gly Thr Leu Val Thr Val Ser Ser |
| 39 | NS-001 variable zone in light chain | Glu Ile Val Met Thr Gln Ser Pro Ala Thr Leu Ser Val Ser Pro Gly Glu Arg Ala Thr Leu Ser Cys Arg Ala Ser Gln Ser Val Ser Tyr Met His Trp Tyr Gln Gln Lys Pro Gly Gln Ala Pro Arg Leu Leu Ile Tyr Gly Val Phe Arg Arg Ala Thr Gly Ile Pro Asp Arg Phe Ser Gly Ser Gly Ser Gly Thr Asp Phe Thr Leu Thr Ile Gly Arg Leu Glu Pro Glu Asp Phe Ala Val Tyr Tyr Cys Leu Gln Trp Ser Ser Asp Pro Pro Thr Phe Gly Gln Gly Thr Lys Leu Glu Ile Lys |
| 40 | NS-001 variable zone in heavy chain | Gln Val Gln Leu Val Gln Ser Gly Ala Glu Val Lys Lys Pro Gly Ala Ser Val Lys Val Ser Cys Lys Ala Ser Gly Tyr Thr Phe Ser Thr Met Tyr Met Ser Trp Val Arg Gln Ala Pro Gly Gln Gly Leu Glu Trp Met Gly Arg Ile Asp Pro Ala Asn Glu His Thr Asn Tyr Ala Gln Lys Phe Gln Gly Arg Val Thr Met Thr Arg Asp Thr Ser Ile Ser Thr Ala Tyr Met Glu Leu Ser Arg Leu Thr Ser Asp Asp Thr Ala Val Tyr Tyr Cys Ala Arg Ser Tyr Tyr Tyr Ala Met Asp Tyr Trp Gly Gln Gly Thr Leu Val Thr Val Ser Ser |
| 41 | NS-001 variable zone in light chain | Gln Ile Val Leu Thr Gln Ser Pro Ala Thr Leu Ser Val Ser Pro Gly Glu Arg Ala Thr Leu Ser Cys Arg Ala Ser Gln Ser Val Ser Tyr Met His Trp Tyr Gln Gln Lys Pro Gly Gln Ala Pro Arg Leu Leu Ile Tyr Gly Val Phe Arg Arg Ala Thr Gly Ile Pro Asp Arg Phe Ser Gly Ser Gly Ser Gly Thr Asp Phe Thr Leu Thr Ile Gly Arg Leu Glu Pro Glu Asp Phe Ala Val Tyr Tyr Cys Leu Gln Trp Ser Ser Asp Pro Pro |

Beneficial Effect

The invention provides a new and better treatment method for the treatment of inflammatory immune diseases. Through the disclosure of the invention, the system or topical PCSK9 inhibitor can be further prepared, and a new monomer drug or compound preparation containing various PCSK9 inhibitors can be developed. Furthermore, new monomers or compound formulations containing all kinds of PCSK9 inhibitors have been developed for the treatment of various types of inflammatory immune diseases, especially psoriasis, eczema and urticaria. Clinical trials have shown that these drugs, which contain PCSK9 inhibitors, are effective, have little adverse reactions, and are well tolerated in patients. In particular, topical use alone can significantly improve lesions in immune diseases such as psoriasis. It is very suitable for the current clinical demand and is expected to have great application prospect, which will bring more advantages to the patients with inflammatory and immunological diseases.

EXAMPLES

The following specific examples illustrate the embodiments of this invention. Technical personnel in this field can easily understand the other advantages and effects of the invention from the contents disclosed in this invention. The invention is not limited to the embodiments described herein. Before further describing the embodiments of this invention, it should be understood that the scope of protection of the invention is not limited to the following specific embodiment. It should be also understood that the term used in the specific examples of the invention is used to describe a specific embodiment rather than to limit the protection scope of the invention. In the description and claims of the invention, unless expressly stated in the text, the singular form "one" and "this" include plural forms.

It should be understood that when a numerical range is given in an example, unless stated by the invention, the two endpoints and any between the two endpoints of each numerical range can be selected. Unless defined herein, all technical and scientific terms used in the invention have the same meaning as those commonly understood by those in the technical field. Except for specific methods, equipment, materials used in the embodiment, according to the description of the invention, one skilled in the art would understand the use of the equivalents of the methods, equipment, and materials described herein.

Example 1

PCSK9 Knockout Significantly Alleviates Psoriasis-Like Inflammation Reaction Induced by IMQ in Mice Reagents: 5% imiquimod cream (IMQ), PCSK9 antibody (abcam), NF-kB antibody(abcam)

Experimental animal: C57BL/6 (B6) mice, 7 male; C57BL/6-PCSK9-r-mice, 5 males and 5 females. The mice were purchased at the Jackson Institute in Maine, USA (The Jackson Laboratory).

Experimental Methods:
1. After two groups of mice with different genotypes were treated with back hair removal, 5% Imiquimod cream of 62.5 mg was applied daily for 5 days.
2. Scores (the score of erythema, scales, skin lesions thickening and total score) were taken and archived (the score was obtained by two researchers respectively then average score was calculated) before and after the application.
3. On the last day of the experiment, all the mice were eulogized and the skin tissue of the back (treated and untreated) was taken.
4. The morphology of skin lesions in each group was observed by HE staining and the expression and distribution of PCSK9 and NF-kB in skin lesions of 4 groups were measured by immunofluorescence method.

Figure 3:
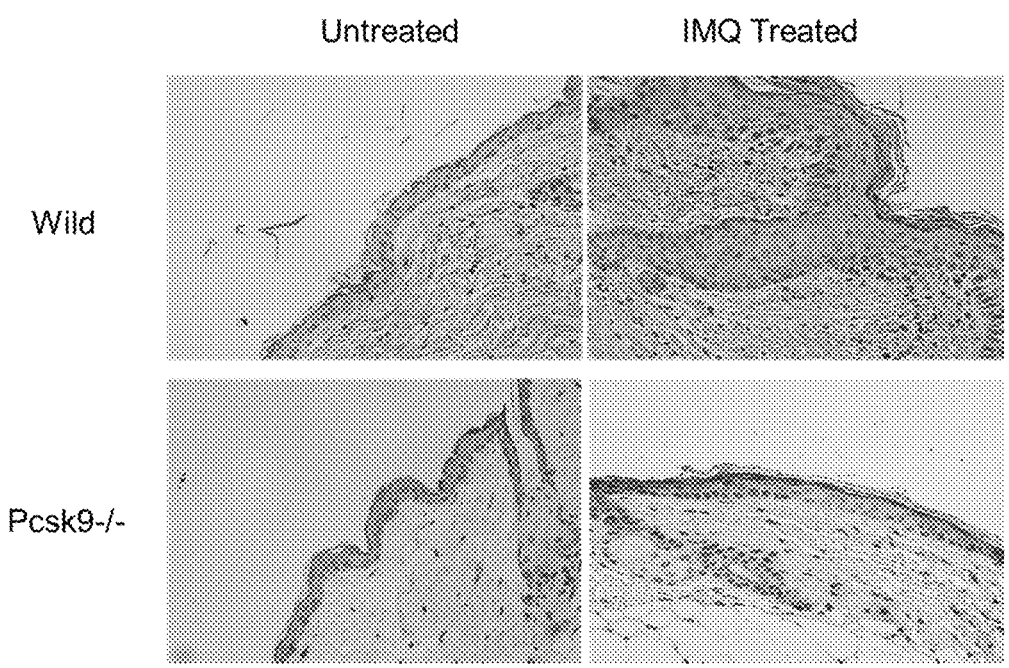
FIG. 3: The histopathological changes of skin in the IMQ treatment region of PCSK9 knockout mice were closer to normal. After 5 days' coating, the skin tissue (treated and non-treated) of mice back were stained with HE. The skin of IMQ treatment area of C57BL/6 mice showed typical psoriasis pathological changes, such as skin thickening, dermatoid lengthening, thickening of spinous layer, hyperkeratosis with incomplete keratosis, Kogoj abscess and Munro abscess. However, the skin of PCSK9 gene knockout mice showed mild epidermis thickening and hyperkeratosis, no extension of dermatoid, thickening of spinous layer, hyperkeratosis with incomplete keratosis, and typical psoriatic pathological changes, such as Kogoj abscess and Munro abscess. The untreated skin of both groups showed normal skin structure.
Figure 4:
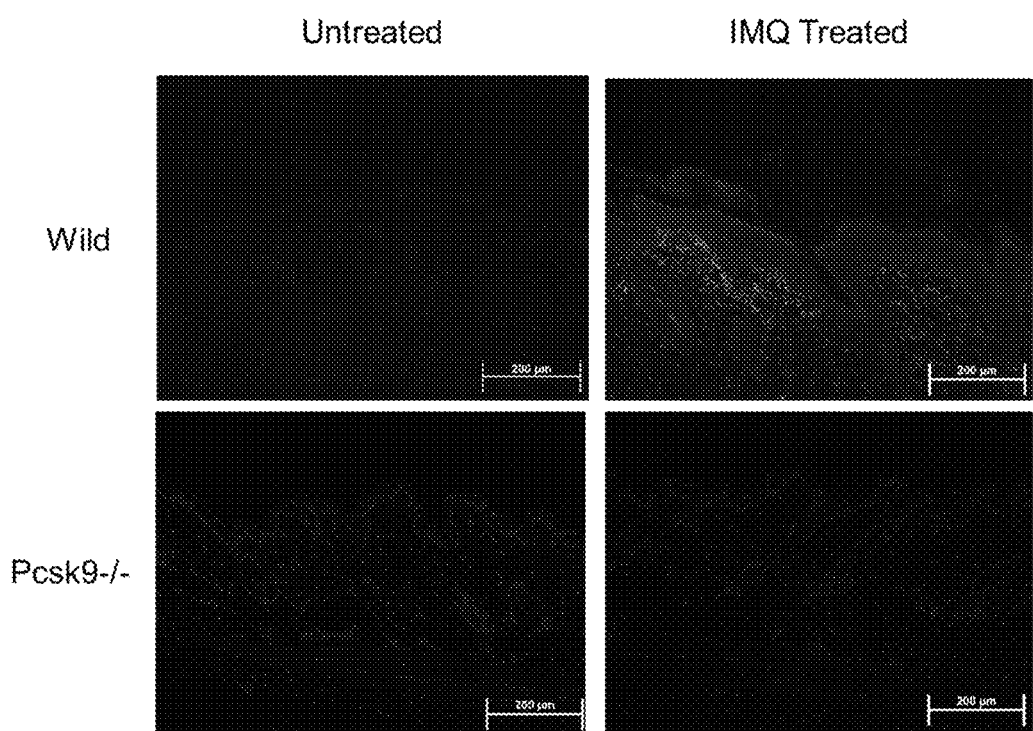
FIG. 4: Immunofluorescence assay showed: Compared with PCSK9 knockout mice, the expression of PCSK9 in the control group was upregulated in the skin of the inflammatory area. The expression of PCSK9 in IMQ treated area of C57BL/6 mice was significantly higher than that in untreated area. However, there was no PCSK9 expression in the skin of IMQ treated and untreated regions of PCSK9 knockout mice.
Figure 5:
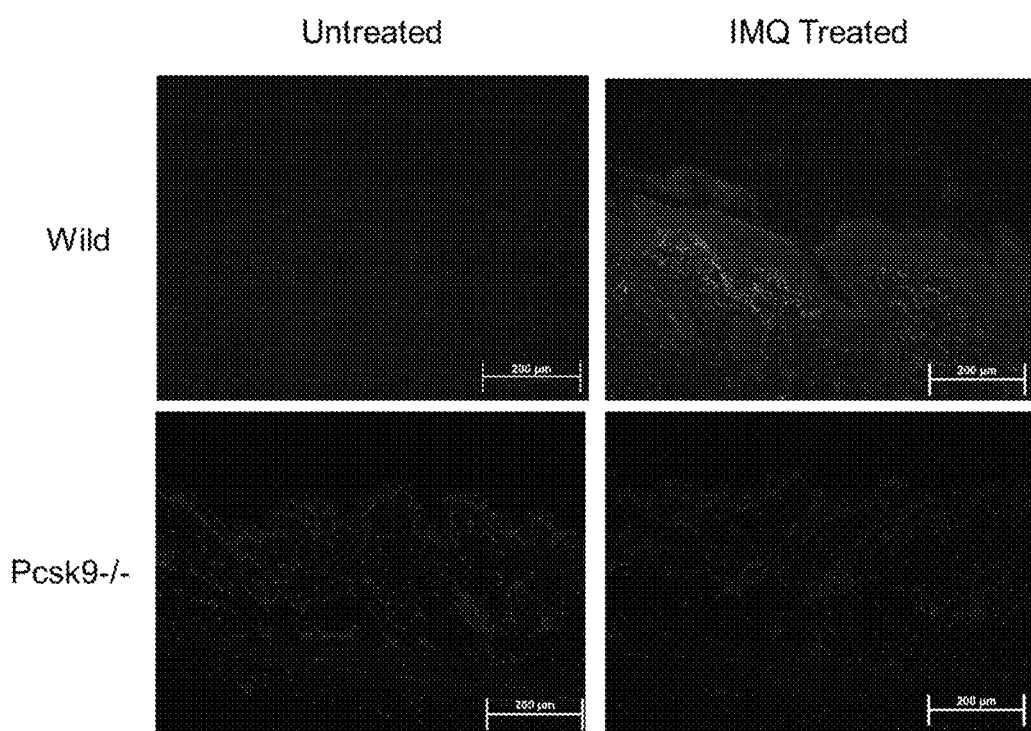
FIG. 5: The expression of NF-kB in the skin of PCSK9 knockout mice was significantly lower than that of the control group. The expression of NF-kB in the skin of C57BL/6 mice and PCSK9 knockout mice was significantly higher than that of the untreated regions in the skin of C57BL/6 mice and PCSK9 knockout mice respectively. However, the expression of NF-kB in the skin of PCSK9 knockout mice was significantly lower than that of C57BL/6 mice.

Experimental Results:
1. After 5 days of continuous application, there were obvious erythema, scales and infiltration in the back of 7 C57BL/6 mice, which were in accordance with the appearance of psoriasis-like skin lesions. In 10 PCSK9 knockout mice, there were only slight erythema, scales and infiltration in the back coating area (See FIG. 1).
2. A daily score was given on the skin lesions of the drug-coated area on the back of the mice, the score of erythema, scale, infiltration and total score of C57BL/6 mice were significantly higher than those of PCSK9 knockout mice ($P<0.05$).
3. After 5 days of application, the skin tissues of the mice's back (treated and untreated) were taken for HE staining and pathological changes were observed. The skin of IMQ treatment area of C57BL/6 mice showed typical psoriasis pathological changes, such as skin thickening, dermatoid lengthening, thickening of spinous layer, hyperkeratosis with incomplete keratosis, Kogoj abscess and Munro abscess, etc. However, the skin of PCSK9 gene knockout mice showed mild epidermis thickening and hyperkeratosis, no typical pathological changes of psoriasis, such as extension of dermatoid, thickening of spinous layer, hyperkeratosis with incomplete keratosis, Kogoj abscess and Munro abscess. The untreated skin of both groups showed normal skin structure (see FIG. 3).

Example 2

Transfection of Si-PCSK9 Enhances Apoptosis and Inhibits Proliferation of Human Keratinocytes.

Experimental Materials and Reagents:
(1) Human primary keratinocytes (Lifeline Cell Technology, FC-0064)
(2) DermaLife Culture medium of keratinocyte (Lifeline Cell Technology, LL-0007), si-PCSK9 (Santa Cruz, sc-45482), Lipofectamine 3000 transfection reagent (ThermalFisher, L-3000001), AnnexinV (BD), PI(BD).

Experimental Methods:
1. Cultured human keratinocytes were replanted in 6 wells plates. When the cell density was 60-70%, si-RNA (si-Con and siPCSK9) transfection was carried out. After 24 h/48 h/72 h of transfection, measured the cell activity of each pore by MTT method. 3 wells were selected at each time point for each group, the average value was taken and the cell activity curve was plotted.
2. Cultured human keratinocytes were replanted in 6 wells plates. When the cell density was 60-70%, si-RNA (si-Con & si-PCSK9) transfection was carried out. After 24 h/48 h/72 h of transfection, cells were harvested respectively for AnnexinV and PI staining to detect cell apoptosis and cell cycle. 3 wells were selected at each time point for each group, the average value was taken.

Figure 6:
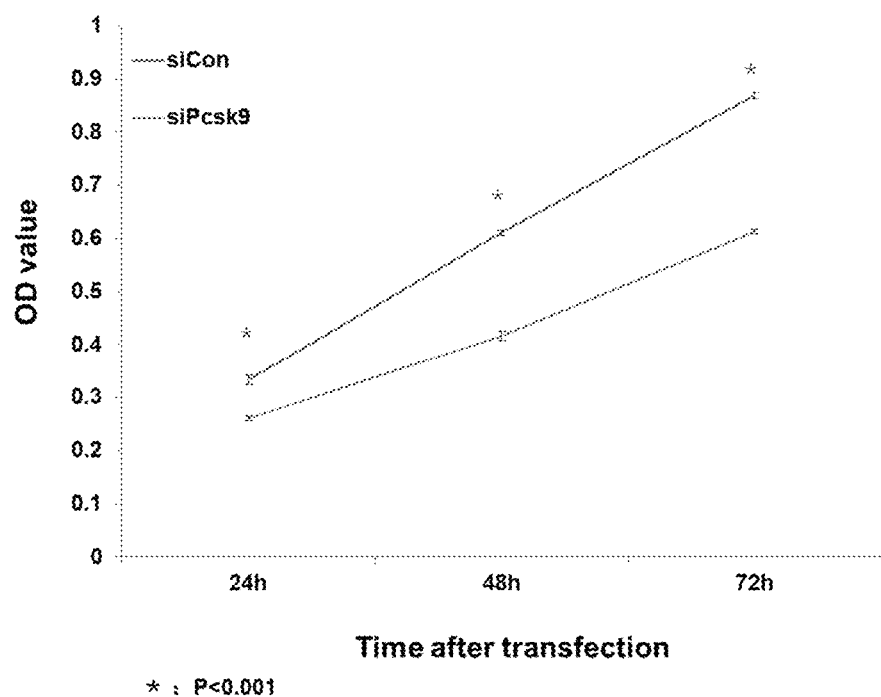
FIG. 6: si-PCSK9 transfection significantly inhibited cell viability of human keratinocytes. The survival number of primary keratinocytes transfected with si-PCSK9 was significantly lower than that of si-Con transfection (P<0.001).
Figure 7:
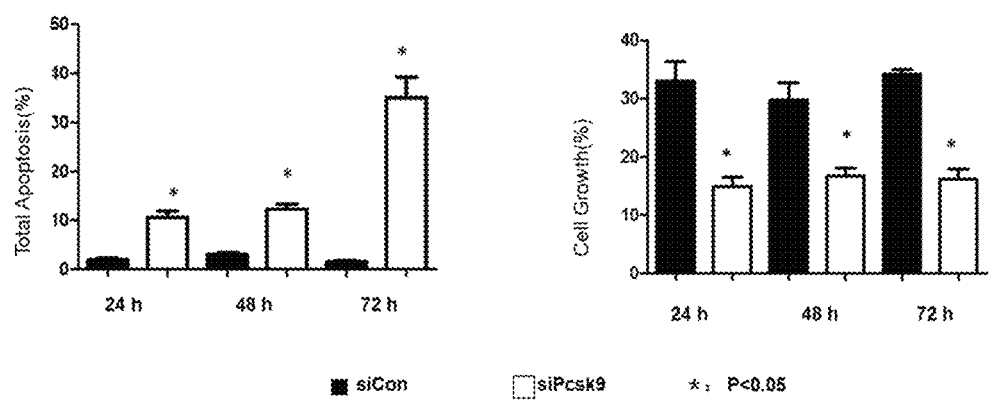
FIG. 7: si-PCSK9 transfection significantly promoted apoptosis and inhibited the proliferation of human keratinocytes. The apoptosis of primary keratinocytes transfected with si-PCSK9 increased significantly (P<0.05), while proliferating (the proportion of S+G2/M phase cells) decreased significantly (P<0.05).

Experimental Results:
1. The number of survival cells of human primary keratinocytes transfected with si-PCSK9 was significantly lower than that of si-Con transfection ($P<0.05$, See FIG. 6).
2. The apoptosis of primary keratinocytes transfected with si-PCSK9 was significantly higher than that of si-Con transfection ($P<0.05$), while proliferating (the proportion of S+G2/M phase cells) decreased significantly (see FIG. 7).

Example 3

The Expression of PCSK9 in Psoriatic Lesions was Significantly Higher than that in Non-Lesions and Normal Controls.

Experiment materials: lesions and non-lesion from 30 psoriasis patients, skin samples from 30 normal people were treated with PCSK9 antibody (abcam).

Methods: immunohistochemistry, real time quantitative-PCR.

Figure 8:
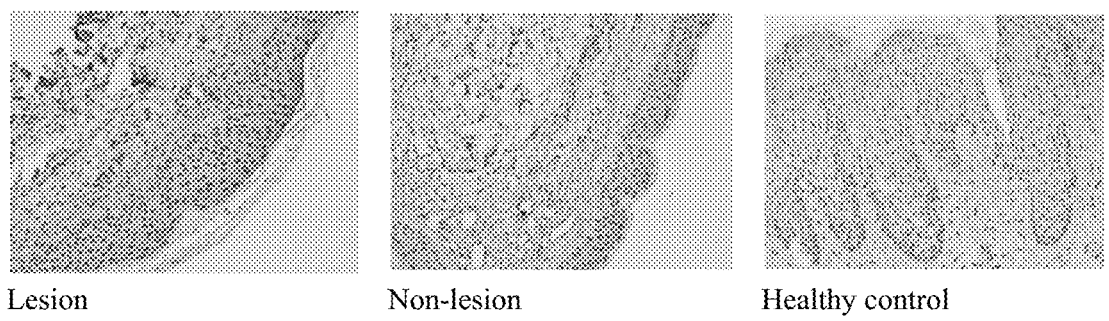
FIG. 8: Immunohistochemically staining showed that the expression of PCSK9 in psoriatic lesions was significantly higher than that in psoriatic non-lesions and normal controls. PCSK9 positive expression cells were mainly distributed in epidermis, and dermis near the epidermis, but not in dermis vessels.
Figure 9:
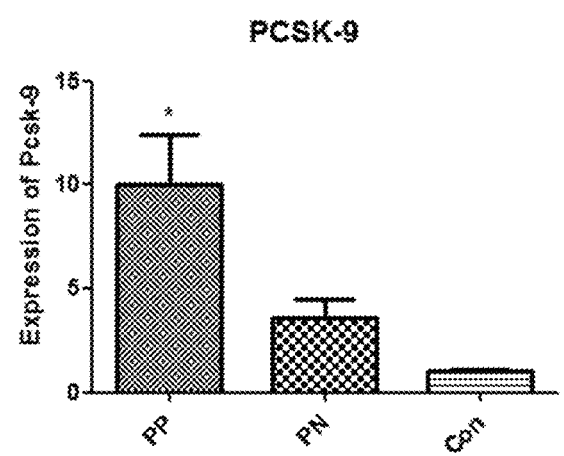
FIG. 9: The results of Q-PCR (quantative PCR) showed that the expression of PCSK9 in psoriatic lesions (PP) group was significantly higher than that in psoriatic non-lesion (PN) group and normal control (NN) group (P<0.001).
Figure 10:
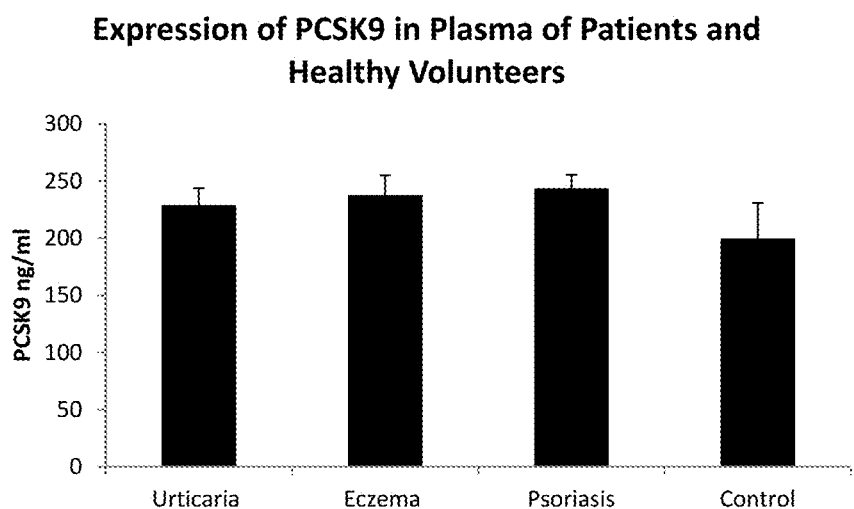
FIG. 10: The expression of PCSK9 in peripheral blood of patients with psoriasis, eczema and urticaria was significantly higher than that of normal controls (P<0.05).

Results: the skin of patients with skin lesions and non-lesions was extracted by drilling method. The skin of normal people originated from the redundant skin of cosmetic surgery. The results of immunohistochemistry showed that the expression of PCSK9 in psoriatic lesions was significantly higher than that in non-lesions and normal controls. PCSK9 positive cells were mainly distributed in epidermis and dermis near epidermis, but not in dermis vessels (see FIG. 8). RNA was extracted from skin homogenate. Q-PCR detection showed that the expression of PCSK9 in psoriatic lesions group was higher than that in psoriatic non-lesion group and normal control group (P<0.05) (see FIG. 9). The results of immunohistochemistry and Q-PCR were consistent.

Example 4

Expression of PCSK9 in Peripheral Blood Mononuclear Cells and Plasma in Patients with Psoriasis, Eczema and Urticaria.

Materials: 5 ml peripheral blood from 30 cases of psoriasis, 30 cases of eczema, 30 cases of urticaria, and 30 cases of normal persons was collected respectively.

Empirical Method:
(1) Separation of plasma and separation of peripheral PBMC by density gradient method.
(2) Detection of PCSK9 expression in PBMC by real-time quantitative Q-PCR.
(3) The expression of PCSK9 in plasma was detected by enzyme linked immunosorbent assay (Elisa) (PCSK9 Quantikine ELISA Kit, America R&D)
(4) Results: (1) No PCSK expression was detected in PBMC of the samples of psoriasis, eczema, urticarial and normal people.
(5) PCSK expression in the samples of psoriasis, eczema, and urticaria are much higher than that in the sample of the normal people. PCSK expression is the highest in the samples of psoriasis.

Example 5

Effect of PCSK9 Protein on the Secretion of IL-17 and IL-2 from Peripheral CD4+T Cells in Patients with Psoriasis, Eczema or Urticaria.

Materials: peripheral blood of 10 cases of psoriasis, 10 cases of eczema, 10 cases of urticaria, and 10 cases of normal people. ELISA kit was purchased from Raybiotech Company of USA.

Experimental Methods:
(1) Isolation of CD4$^+$T cells from peripheral blood:
After PBMC was isolated by Ficoll-Hypaque from human peripheral blood by density gradient centrifugation, washed with 10 times volume 1×BD beads buffer. Then 50 ul BD IMag TM CD4 beads were added to each 107 cells. The beads were mixed well and incubated at room temperature for 30 minutes. 1 ml 1×BD magnetic bead buffer solution was added, and the cells were transferred to the round bottom tube and placed in the magnetic frame for 8 to 10 minutes. And then the supernatant was discarded and removed the test tube from the magnetic field. After resuspension of cells attached to tube wall with 1 ml 1×BD magnetic bead buffer, the tubes were placed in magnetic field for 2-4 min again. The supernatant was discarded removed it out of the magnetic field, resuspended the cells and placed the tube in the magnetic field for 2-4 min. The cells obtained from the supernatant can be used in subsequent experiments. BD IMag TM CD4 separation system was purchased from BD Biosciences Company.

(2) Determination of cytokines secreted by CD4$^+$T cells in Peripheral Blood

The supernatant was collected after cell culture under different conditions. IFN-Gamma represented TH1 type cytokines, IL-4 represented TH2 type cytokines, and IL-17 represented TH17 cytokines. The detection of IFN-Gamma, IL-4, IL-17 was conducted by ELISA.

Figure 11:
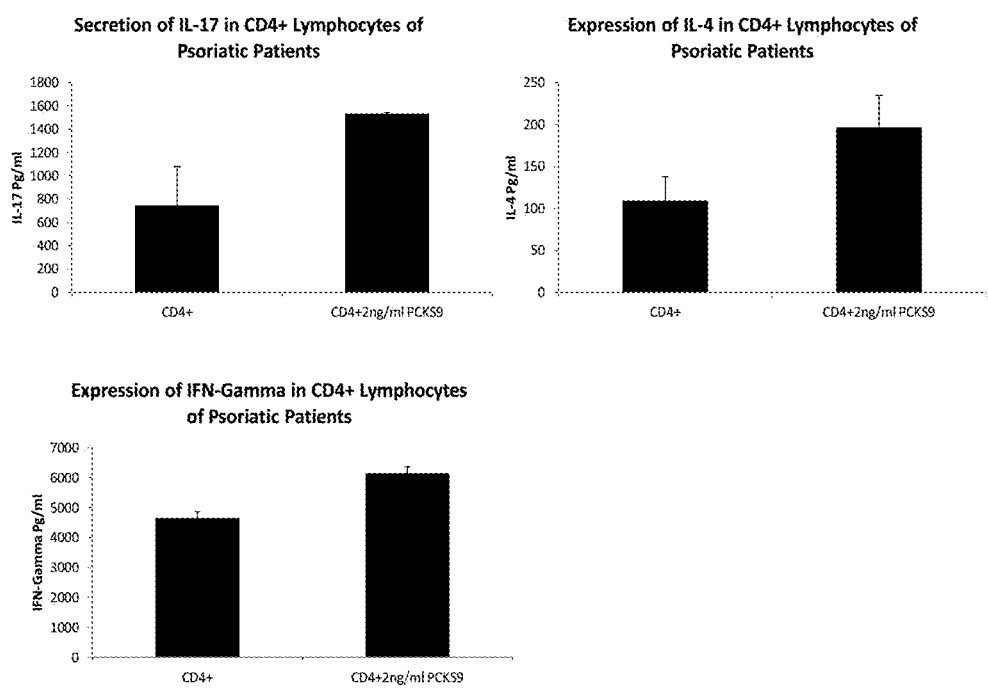
FIG. 11: PCSK9 protein can significantly promote the secretion of IL-17, IL-2 and IFN-Gamma (P<0.01) by CD4 T cells isolated from peripheral blood of patients with psoriasis, eczema and urticaria.

Results: Compared to the normal patients, PCSK9 protein can significantly promote the secretion of IL-17, IL-2 and IFN-Gamma (P<0.01) by CD4 T cells isolated from peripheral blood of patients with psoriasis, eczema and urticaria (FIG. 11).

Example 6

Subcutaneous Injection of PCSK9 Small Molecule Inhibitor and PCSK9 Monoclonal Antibody Significantly Alleviated Systemic Immune Abnormalities and Skin Lesions Induced by IMQ in Mice. The Efficacy of PCSK9 Small Molecule Inhibitor is Better than that of Subcutaneous Injection of PCSK9 Monoclonal Antibody.

Reagents:
The PCSK9 small molecule inhibitor used for this example has the formula of:

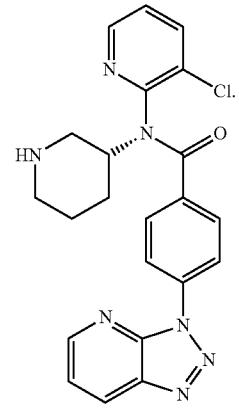

The PCSK9 monoclonal antibody used for this example is Evolocumab. 40 SPF female BALB/c mice aged 6-8 weeks were randomly divided into normal control group, model group, PCSK9 small molecule inhibitor group and PCSK9 monoclonal antibody group. There were 10 mice for each group. After intraperitoneal injection of pentobarbital sodium 80 mg/kg, the back was shaved with an area of about 2 cm×3 cm. The mice were feed separately for 1 day.

(1) In normal control group, Vaseline was applied locally. In model group, inhibitor group and monoclonal antibody group, 62.5 mg of 5% imiquimod cream was applied on the back every day for 6 consecutive days, photos were taken and the PASI score was evaluated.

(2) On the first day, normal saline was subcutaneously administrated to normal control group and model group, PCSK9 small molecule inhibitor was subcutaneously administrated (8 mg/kg, Purchased from Selleck Inc.) to inhibitor group, and PCSK9 monoclonal antibody was subcutaneously administered to monoclonal antibody group (10 mg/kg, Purchased from abcam Inc.)

Figure 12:
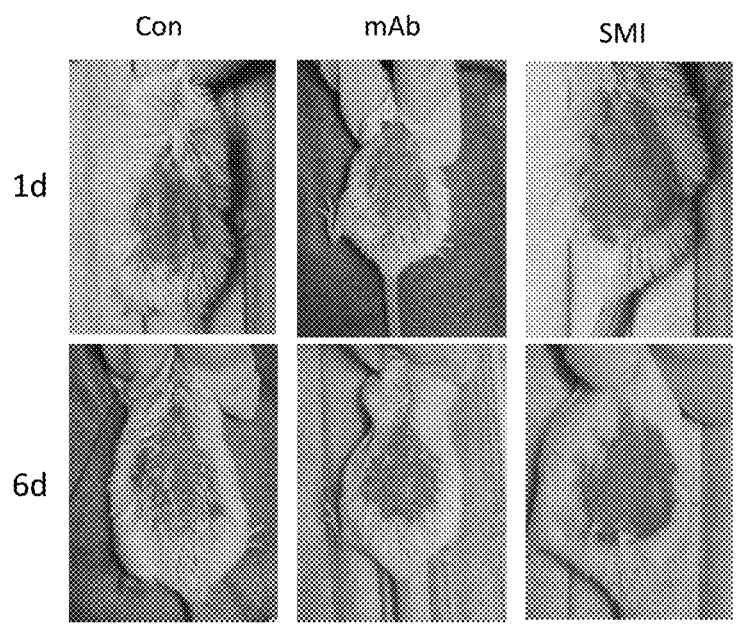
FIG. 12: Subcutaneous injection of PCSK9 small molecule inhibitor and PCSK9 monoclonal antibody can reduce the score of erythema, scale and infiltration induced by IMQ in mice skin (P<0.01).
Figure 12:
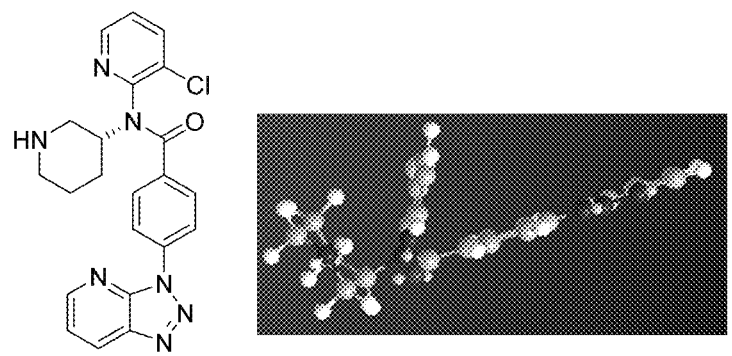

Experimental Results:

(1) After 6 days of continuous application, there were marked erythema, scales and infiltration in the back of the mice in the model group. However, in PCSK9 small molecule inhibitor group and PCSK9 monoclonal antibody group, there was only mild erythema, scales and infiltration in the back coating area of mice. The effect of PCSK9 small molecule inhibitor group was better than that of PCSK9 monoclonal antibody group. No lesions were observed in the vaseline group (FIG. 12).

(2) A daily scoring was given on the skin lesions of the drug-coated area on the back of the mice. The score of erythema, scales, infiltration and total score of PCSK9 small molecule inhibitor group (erythema+scales+infiltration) were significantly lower than that of PCSK9 monoclonal antibody group (P<0.01).

Example 7

Both PCSK9 Small Molecule Inhibitor and PCSK9 Monoclonal Antibody Improved the IMQ Induced Psoriatic Lesions of Mice, and the Efficacy of Small Molecule Inhibitor was Better than that of Monoclonal Antibody Reagents:

The PCSK9 small molecule inhibitor used for this example has the formula of:

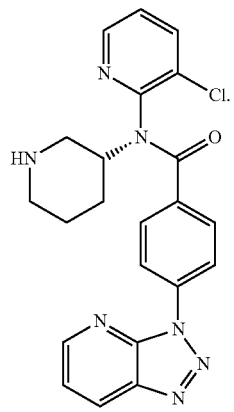

The PCSK9 monoclonal antibody used for this example is Evolocumab.

(1) 40 SPF female BALB/c mice aged 6-8 weeks were randomly divided into normal control group, model group, PCSK9 inhibitor group and PCSK9 monoclonal antibody group. There were 10 mice for each group. After intraperitoneal injection of pentobarbital sodium 80 mg/kg, the back was shaved with an area of about 2 cm×3 cm. The mice were feed separately for 1 day.

(2) In normal control group, vaseline was applied locally. In model group, small molecule inhibitor group and monoclonal antibody group, 62.5 mg of 5% imiquimod cream was applied on the back every day for 6 consecutive days, and photos were taken and the PASI score was evaluated.

(3) Pretreatment: vaseline was applied on the back skin with mics in normal control group and model group, PCSK9 small molecule inhibitor cream (0.01% concentration) was applied to inhibitor group once daily. And, PCSK9 monoclonal antibody cream (0.01% concentration) was applied to monoclonal antibody group once daily.

(4) After 7 days pretreatment, vaseline was applied on the back skin with mice in normal control group. At the same time, 62.5 mg 5% imiquimod cream was regularly applied daily on the back with mice in model group, small molecule inhibitor group and monoclonal antibody group. PCSK9 small molecule inhibitor cream or PCSK9 monoclonal antibody cream was applied after one hour. For 6 consecutive days, photos were taken and the PASI score was evaluated.

Figure 13:
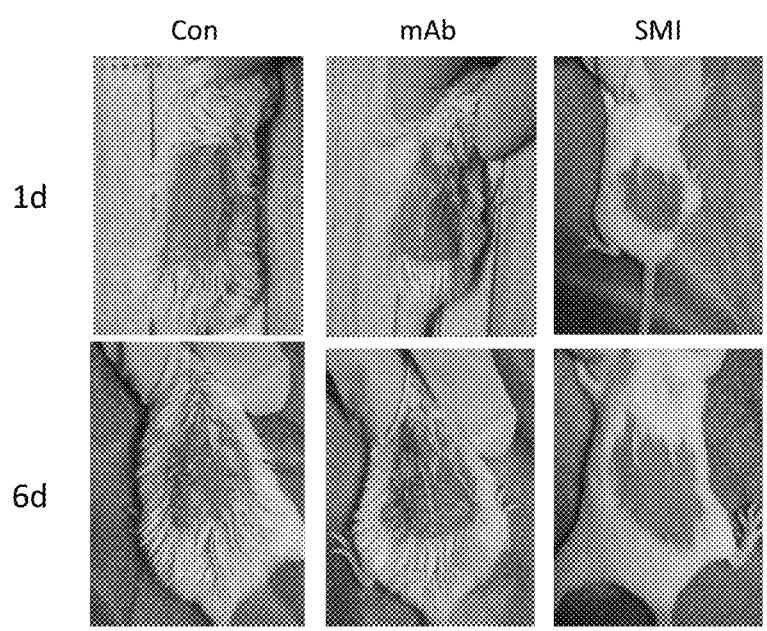
FIG. 13: External use of PCSK9 small molecule inhibitors and PCSK9 monoclonal antibodies can significantly reduce the score of skin erythema, scale, and infiltration of IMQ induced mice. The efficacy of PCSK9 small molecule inhibitor is better than that of PCSK9 monoclonal antibody (P<0.01).

Experimental Results:

1. After 6 days of continuous administration, erythema, scales and infiltration were observed in the coating areas at the back of the mics in the model group. However, there were only slight erythema, scales and infiltration in the back of the mice in the PCSK9 small molecule inhibitor group and the PCSK9 monoclonal antibody group. The effect of PCSK9 small molecule inhibitor group was better than that of PCSK9 monoclonal antibody group. No lesion was observed in the vaseline group (See FIG. 13).

2. A daily score was given on the skin lesions of the drug-coated area on the back of the mice. The score of erythema, scales, infiltration and total score (erythema+scales+infiltration) in PCSK9 small molecule inhibitor group was significantly lower than that in PCSK9 monoclonal antibody group (P<0.01).

Example 8

External Use of siRNA for PCSK9 could Significantly Reduce Psoriatic Lesions Induced by IMQ in Mice.

Materials and Methods:

1. Animal models: two types of mice models, C57BL/6J (B6) and Balb/cByJ (BALB) were used in this study. The mice was purchased at the Jackson Institute in Maine, USA. (The Jackson Laboratory). The strain number was 000664, 001026 and 005993 respectively (www.jax.org). All the mice in this experiment were female, aged 3-8 months, 5 mice for each group.

2. Psoriatic lesions induced by IMQ: the back hair of B 6 mice was removed one day before the experiment. During the experiment, 62.5 mg imiquimod (IMQ, 3 M pharmaceuticals) were smeared on the skin of each mouse with an area of 2 cm$^2$ on the back. In some mice, right auricle was also smeared with 5 mg IMQ to detect skin thickening easily. After 24 hours, score of the skin color, thickness and scales degree was evaluated.

3. Inhibition of PCSK9 by siRNA and its effect on psoriatic lesions induced by IMQ: Two siRNAs for PCSK9 (siPCSK9-1, 2) and a random sequence siRNA (siCon), used as a control trial, was synthesized by Sigma-Aldrich company (Sigma-Aldrich, USA). The sequence was shown in Table 3. Mixed siPCSK9-1 and 2 equally and diluted it to 20 µM with normal saline. 12.5 µl diluted siPCSK9 was evenly mixed with 7.5 µl moisturizer (CVS Pharmacy, Baby Lotion), so it was done with siCon. Applied 20 µl siRNA-moisturizer mixture to the skin 1 hour before IMQ was applied. PCSK9 monoclonal antibody was purchased from abcam Company and was evenly mixed with PCSK9 moisturizer (CVS pharmacy, Baby Lotion) to generate an equal concentration emulsion with siPCSK9 emulsion.

4. From the first day, siCON was applied on the back skin of B6 mice in model group after 1 hour-vaseline treatment. B6 mice in siPCSK9 group were smeared with 5% imiquimod cream on their back, then 1 hour thereafter, siPCSK9 was applied once daily. In PCSK9 monoclonal antibody group, 5% imiquimod cream was applied on the back skin of B6 mice, then 1 hour thereafter, PCSK9 monoclonal antibody was applied once daily.

5. Gene expression detection by semi quantitative (real-time PCR): Primer sequence was shown in Table 3

TABLE 3 siRNA sequence and modification

| Gene | 5'-3' Sense | 5'-3' Antisense |
|---|---|---|
| siPCSK9-1 | GccuGGAGuuuA uucGGAAdT*dT | UUCCgAAuAAAC UCcAGGCdT*dT |
| siPCSK9-2 | AGGuGuAucucc uAGAcAcdT*dT | GUGUCuAGGAGA uAcACCUdT*dT |
| siCON | cuuAcGcuGAGu AcuucGAdT*dT | UCGAAGuACUcA GCGuAAGdT*dT |

Note:
lowercase letters denote 2'-OMe modification. All sequences were connected with phosphorothioate at the end of the sequence.

TABLE 4

Primer sequence

| Gene | Forward Sequence | Reverse Sequence |
|---|---|---|
| PCSK9 | TTGCAGCAGCTG GGAACTT | CCGACTGTGATG ACCTCTGGA |
| NFkB | CTGGTGGACACA TACAGGAAGAC | ATAGGCACTGTC TTCTTTCACCTC |
| IL-17A | TTTTCAGCAAGG AATGTGGA | TTCATTGTGGAG GGCAGAC |
| IL-22 | TTTCCTGACCAA ACTCAGCA | CTGGATGTTCTG GTCGTCAC |
| IL-23 | CACCTCCCTACT AGGACTCAGC | TGGGCATCTGTT GGGTCT |

Figure 14:
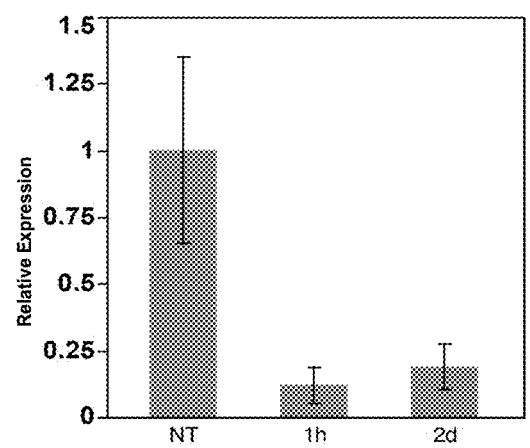
FIG. 14: Compared with control siRNA(siCon), siPCSK9 could significantly reduce the expression of PCSK9 in mouse skin one day after the application, and the inhibition rate was more than 80%.
Figure 15:
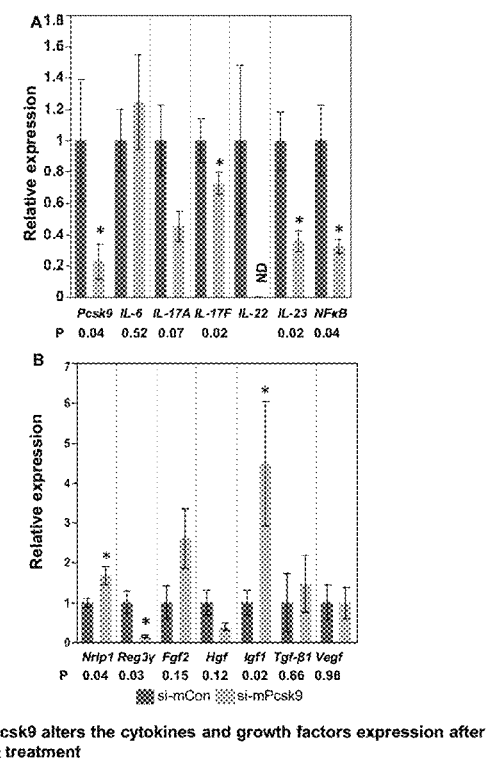
FIG. 15: siPCSK9 can inhibit the expression of NF kappa B, IL-17, IL-22, IL-23 and other inflammatory factors after a day of skin treatment.

Experimental Results:
1. siPCSK9 can significantly reduce the expression of PCSK9 in the skin of B6 mice one day after being applied to the skin (p<0.05); inhibition rate is over 80% (FIG. 14). A day after siPCSK9 treatment of skin, it can inhibit the expression of NF κB, IL-17, IL-22, IL-23 and other immune factors (Figure. 15). The expression of these inflammatory factors is closely related to the pathogenesis and severity of psoriasis, suggesting that siPCSK9 can inhibit the occurrence of psoriasis and alleviate the pathological reaction.

2. After 6 days of continuous application, there were significant erythema, scales and infiltration in the coating area of the model group, but only slight erythema, scale and infiltration in the siPCSK9 group (see FIG. 16). The therapeutic effect of siPCSK9 group on psoriasis lesions in mice was significantly better than that in control group (P<0.01), but no lesions were found in Vaseline group.

Figure 16:
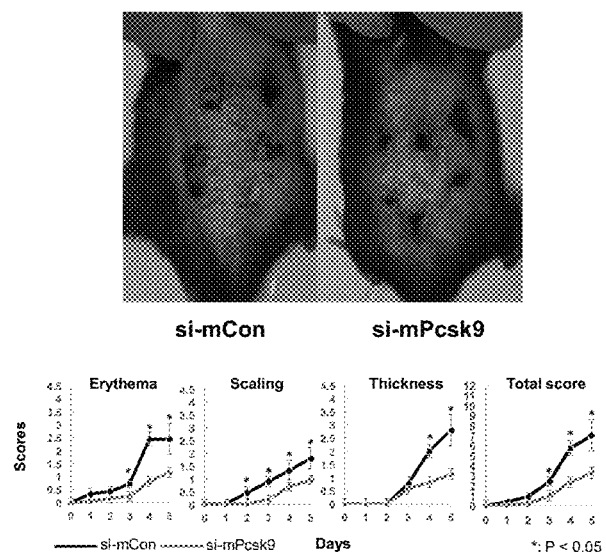
FIG. 16: After induction of IMQ, the skin psoriasis lesion, erythema, scale and infiltration score of mice treated with siPCSK9 were significantly lower than those of the control group (P<0.01).

3. Daily scoring of skin lesions in B6 mice showed that the scores of erythema, scale, infiltration and the total scores (erythema+scale+infiltration) in siPCSK9 group were significantly lower than those in control group (P<0.01) (FIG. 16).

Figure 17:
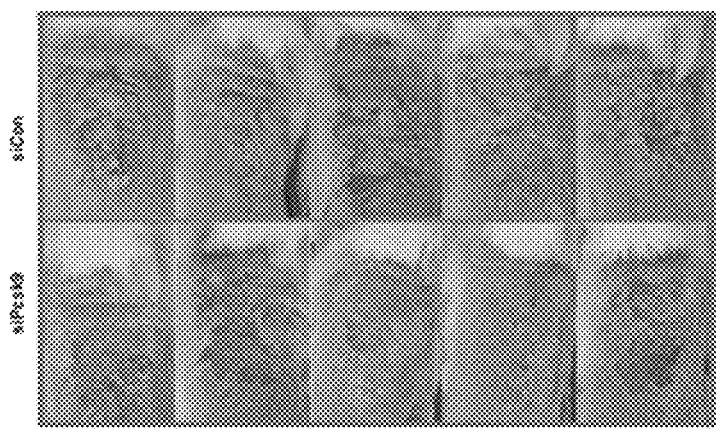
FIG. 17: On days 2-6 after induction of IMQ, compared with the control group, the skin erythema, scales and infiltration of BALB mice induced by IMQ were significantly inhibited by siPCSK9.

4. To further verify the inhibitory effect of siPCSK9 on psoriatic lesions induced by IMQ, we repeated the experiment in FIG. 16 in another wild mice BALB using the same treatment, and the results was very similar (FIG. 17).

The specific embodiments are described above in detail. Within the knowledge of the technical personnel in this field, various changes can also be made without departing from the concept of the invention.

The invention claimed is:

1. A method of treating an inflammatory immune disease by administration of a therapeutically effective amount of a proprotein convertase subtilisin kexin 9 (PCSK9) inhibitor selected from the group consisting of:

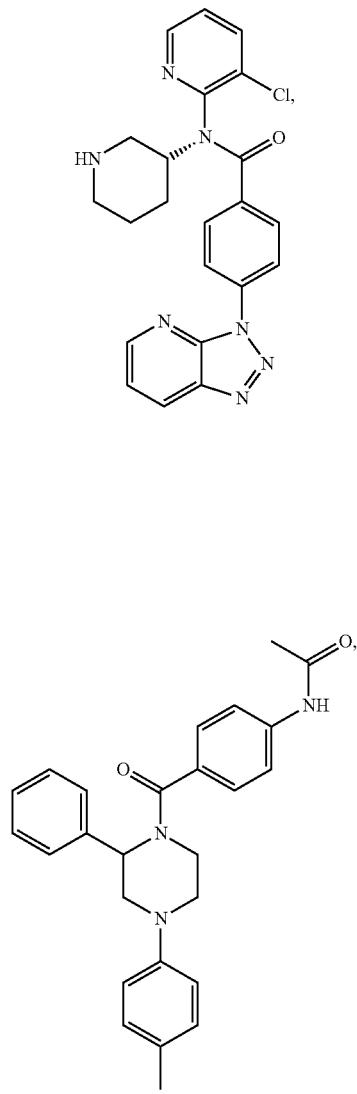

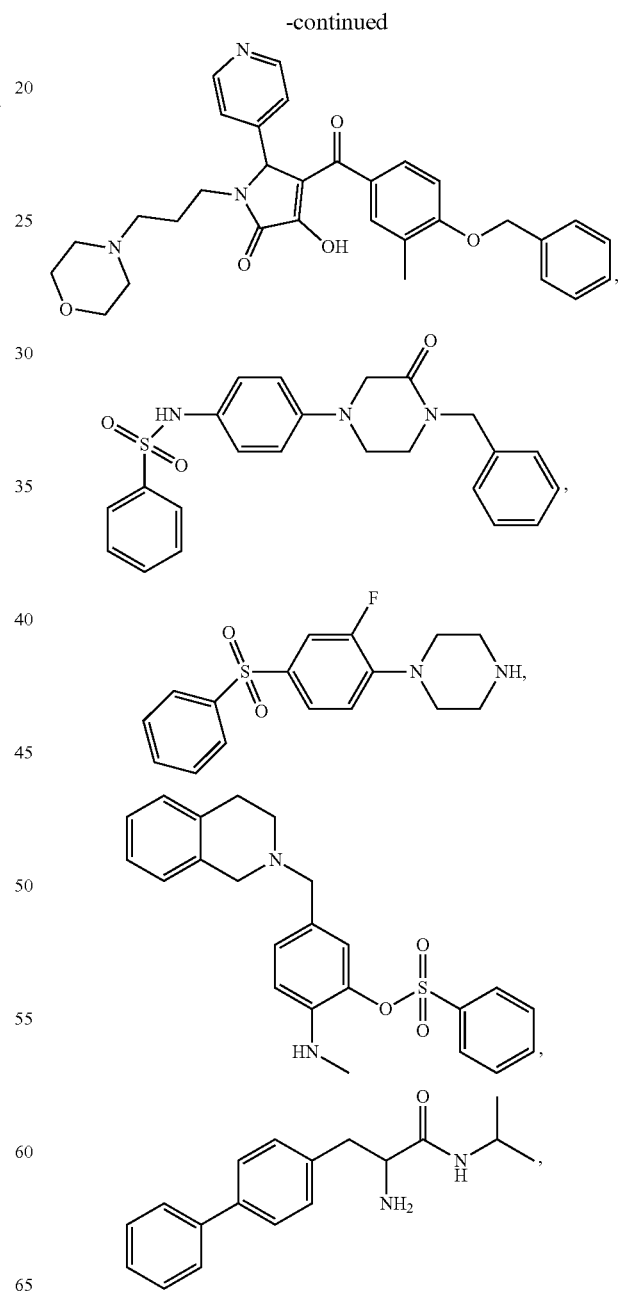

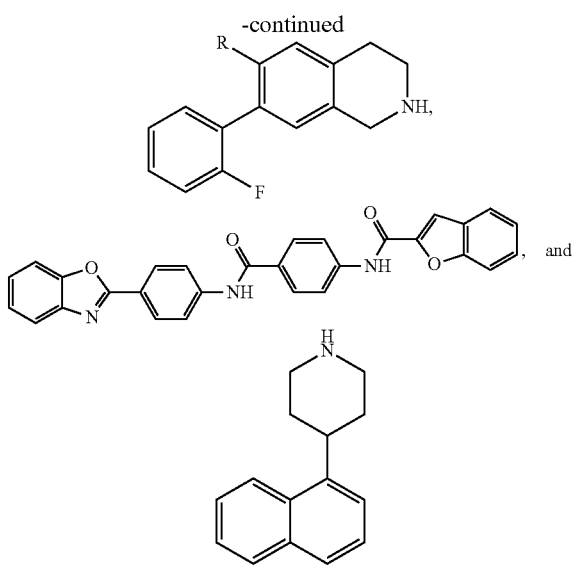

to a human in need thereof, wherein the inflammatory immune disease is selected from the group consisting of psoriasis, psoriatic arthritis, eczema, atopic dermatitis, urticaria, glucocorticoid dependent dermatitis, rheumatoid arthritis, scleroderma, diabetes, chronic liver disease, and lymphoma.

2. The method of claim 1, wherein the inflammatory immune disease is psoriasis, atopic dermatitis or urticaria, wherein the PCSK9 inhibitor is topically or systemically administered.

3. The method of claim 2, wherein the inflammatory immune disease is psoriasis.

4. The method of claim 1, wherein the PCSK9 inhibitor has the formula:

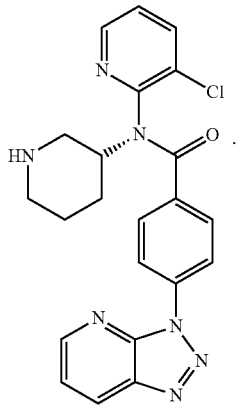

5. The method of claim 4, wherein the therapeutically effective amount of the PCSK9 inhibitor is administered subcutaneously.

6. The method of claim 4, wherein the therapeutically effective amount of the PCSK9 inhibitor is administered topically.

7. The method of claim 4, wherein the inflammatory immune disease is selected from the group consisting of psoriasis, psoriatic arthritis, eczema, atopic dermatitis, urticaria, glucocorticoid dependent dermatitis, and scleroderma.

8. The method of claim 7, wherein the inflammatory immune disease is psoriasis.

9. The method of claim 8, wherein the PCSK9 inhibitor is administered subcutaneously or topically.

10. The method of claim 9, wherein the PCSK9 inhibitor is administered topically as a cream or ointment containing the PCSK9 inhibitor in a concentration of 0.001-0.05%.

11. The method of claim 9, wherein the PCSK9 inhibitor is administered subcutaneously at a concentration of 8 mg/kg or in a dose of 5 mg.

12. The method of claim 1, wherein the PCSK9 inhibitor is administered subcutaneously, topically or systemically.

13. The method of claim 12, wherein the PCSK9 inhibitor is administered subcutaneously or topically.

14. The method of claim 13, wherein the PCSK9 inhibitor is administered (i) topically as a cream or ointment containing the PCSK9 inhibitor in a concentration of 0.001-0.05% or (ii) subcutaneously at a concentration of 8 mg/kg or in a dose of 5 mg.

15. The method of claim 1, wherein the inflammatory immune disease is selected from the group consisting of psoriasis, psoriatic arthritis, eczema, atopic dermatitis, urticaria, glucocorticoid dependent dermatitis, and scleroderma.

16. The method of claim 15, wherein the inflammatory immune disease is psoriasis.

17. The method of claim 16, wherein the PCSK9 inhibitor is administered subcutaneously or topically.

18. The method of claim 17, wherein the PCSK9 inhibitor is administered topically as a cream or ointment containing the PCSK9 inhibitor in a concentration of 0.001-0.05%.

19. The method of claim 17, wherein the PCSK9 inhibitor is administered subcutaneously at a concentration of 8 mg/kg or in a dose of 5 mg.

* * * * *

SEQUENCE LISTING

<160> NUMBER OF SEQ ID NOS: 57

<210> SEQ ID NO 1
<211> LENGTH: 127
<212> TYPE: PRT
<213> ORGANISM: Artificial Sequence
<220> FEATURE:
<223> OTHER INFORMATION: Alirocumab Variable zone in heavy chain

<400> SEQUENCE: 1

Glu Met Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser His
            20                  25                  30

Trp Met Lys Trp Val Arg Gln Ala Pro Gly Lys Gly Leu Glu Trp Val
        35                  40                  45

Ala Asn Ile Asn Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Phe
65                  70                  75                  80

Leu Gln Met Asn Ser Leu Arg Ala Glu Asp Thr Ala Val Tyr Tyr Cys
                85                  90                  95

Ala Arg Asp Ile Val Leu Met Val Tyr Asp Met Asp Tyr Tyr Tyr Tyr

```
                100             105             110
Gly Met Asp Val Trp Gly Gln Gly Thr Thr Val Thr Val Ser Ser
            115             120             125

<210> SEQ ID NO 2
<211> LENGTH: 112
<212> TYPE: PRT
<213> ORGANISM: Artificial Sequence
<220> FEATURE:
<223> OTHER INFORMATION: Alirocumab Variable zone in light chain

<400> SEQUENCE: 2

Asp Ile Val Met Thr Gln Ser Pro Leu Ser Leu Pro Val Thr Pro Gly
1               5                   10                  15

Glu Pro Ala Ser Ile Ser Cys Arg Ser Gln Ser Leu Leu His Ser
            20                  25                  30

Asn Gly Asn Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Thr
                85                  90                  95

Leu Gln Thr Pro Leu Thr Phe Gly Gly Gly Thr Lys Val Glu Ile Lys
            100             105             110

<210> SEQ ID NO 3
<211> LENGTH: 123
<212> TYPE: PRT
<213> ORGANISM: Artificial Sequence
<220> FEATURE:
<223> OTHER INFORMATION: Evolocumab Variable zone in heavy chain

<400> SEQUENCE: 3

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Phe Cys
                85                  90                  95

Ala Arg Asp Tyr Asp Phe Trp Ser Ala Tyr Tyr Asp Ala Phe Asp Val
            100             105             110

Trp Gly Gln Gly Thr Met Val Thr Val Ser Ser
            115             120

<210> SEQ ID NO 4
<211> LENGTH: 111
<212> TYPE: PRT
<213> ORGANISM: Artificial Sequence
<220> FEATURE:
<223> OTHER INFORMATION: Evolocumab Variable zone in light chain

<400> SEQUENCE: 4
```

```
Gln Ser Val Leu Thr Gln Pro Pro Ser Val Gly Ala Pro Gly Gln
1               5                   10                  15

Arg Val Thr Ile Ser Cys Thr Gly Ser Ser Asn Ile Gly Ala Gly
                20                  25                  30

Tyr Asp Val His Trp Tyr Gln Gln Leu Pro Gly Thr Ala Pro Lys Leu
            35                  40                  45

Leu Ile Ser Gly Asn Ser Asn Arg Pro Ser Gly Val Pro Asp Arg Phe
50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Ser Val Phe Gly Gly Gly Thr Lys Leu Thr Val Leu
            100                 105                 110

<210> SEQ ID NO 5
<211> LENGTH: 115
<212> TYPE: PRT
<213> ORGANISM: Artificial Sequence
<220> FEATURE:
<223> OTHER INFORMATION: Evolocumab Variable zone in heavy chain

<400> SEQUENCE: 5

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Leu Thr Ser Tyr
                20                  25                  30

Gly Ile Ser Trp Val Arg Gln Ala Pro Gly Gln Gly Leu Glu Trp Met
            35                  40                  45

Gly Trp Val Ser Phe Tyr Asn Gly Asn Thr Asn Tyr Ala Gln Lys Leu
50                  55                  60

Gln Gly Arg Gly Thr Met Thr Thr Asp Pro Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Tyr Gly Met Asp Val Trp Gly Gln Gly Thr Thr Val Thr
            100                 105                 110

Val Ser Ser
        115

<210> SEQ ID NO 6
<211> LENGTH: 109
<212> TYPE: PRT
<213> ORGANISM: Artificial Sequence
<220> FEATURE:
<223> OTHER INFORMATION: Evolocumab Variable zone in light chain

<400> SEQUENCE: 6

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
                20                  25                  30

Asn Ser Val Ser Trp Tyr Gln Gln His Pro Gly Lys Ala Pro Lys Leu
            35                  40                  45

Met Ile Tyr Glu Val Ser Asn Arg Pro Ser Gly Val Ser Asn Arg Phe
50                  55                  60

Ser Gly Ser Lys Ser Gly Asn Thr Ala Ser Leu Thr Ile Ser Gly Leu
```

```
                65                  70                  75                  80
Gln Ala Glu Asp Glu Ala Asp Tyr Tyr Cys Asn Ser Tyr Thr Ser Thr
                    85                  90                  95

Ser Met Val Phe Gly Gly Gly Thr Lys Leu Thr Val Leu
            100                 105
```

<210> SEQ ID NO 7
<211> LENGTH: 5
<212> TYPE: PRT
<213> ORGANISM: Artificial Sequence
<220> FEATURE:
<223> OTHER INFORMATION: Bococizumab Heavy chain: CDR1

<400> SEQUENCE: 7

```
Ser Tyr Tyr Met His
1               5
```

<210> SEQ ID NO 8
<211> LENGTH: 10
<212> TYPE: PRT
<213> ORGANISM: Artificial Sequence
<220> FEATURE:
<223> OTHER INFORMATION: Bococizumab Heavy chain: CDR1

<400> SEQUENCE: 8

```
Gly Tyr Thr Phe Thr Ser Tyr Tyr Met His
1               5                   10
```

<210> SEQ ID NO 9
<211> LENGTH: 7
<212> TYPE: PRT
<213> ORGANISM: Artificial Sequence
<220> FEATURE:
<223> OTHER INFORMATION: Bococizumab Heavy chain: CDR1

<400> SEQUENCE: 9

```
Gly Tyr Thr Phe Thr Ser Tyr
1               5
```

<210> SEQ ID NO 10
<211> LENGTH: 6
<212> TYPE: PRT
<213> ORGANISM: Artificial Sequence
<220> FEATURE:
<223> OTHER INFORMATION: Bococizumab Heavy chain: CDR2

<400> SEQUENCE: 10

```
Ser Pro Phe Gly Gly Arg
1               5
```

<210> SEQ ID NO 11
<211> LENGTH: 17
<212> TYPE: PRT
<213> ORGANISM: Artificial Sequence
<220> FEATURE:
<223> OTHER INFORMATION: Bococizumab Heavy chain: CDR2

<400> SEQUENCE: 11

```
Glu Ile Ser Pro Phe Gly Gly Arg Thr Asn Tyr Asn Glu Lys Phe Lys
1               5                   10                  15

Ser
```

<210> SEQ ID NO 12
<211> LENGTH: 9
<212> TYPE: PRT

<213> ORGANISM: Artificial Sequence
<220> FEATURE:
<223> OTHER INFORMATION: Bococizumab Heavy chain: CDR3

<400> SEQUENCE: 12

Glu Arg Pro Leu Tyr Ala Ser Asp Leu
1               5

<210> SEQ ID NO 13
<211> LENGTH: 11
<212> TYPE: PRT
<213> ORGANISM: Artificial Sequence
<220> FEATURE:
<223> OTHER INFORMATION: Bococizumab Light chain: CDR1

<400> SEQUENCE: 13

Arg Ala Ser Gln Gly Ile Ser Ser Ala Leu Ala
1               5                   10

<210> SEQ ID NO 14
<211> LENGTH: 7
<212> TYPE: PRT
<213> ORGANISM: Artificial Sequence
<220> FEATURE:
<223> OTHER INFORMATION: Bococizumab Light chain: CDR2

<400> SEQUENCE: 14

Ser Ala Ser Tyr Arg Tyr Thr
1               5

<210> SEQ ID NO 15
<211> LENGTH: 9
<212> TYPE: PRT
<213> ORGANISM: Artificial Sequence
<220> FEATURE:
<223> OTHER INFORMATION: Bococizumab Ligh t chain: CDR3

<400> SEQUENCE: 15

Gln Gln Arg Tyr Ser Leu Trp Arg Thr
1               5

<210> SEQ ID NO 16
<211> LENGTH: 152
<212> TYPE: PRT
<213> ORGANISM: Artificial Sequence
<220> FEATURE:
<223> OTHER INFORMATION: Synthesized

<400> SEQUENCE: 16

Ala Ser Asp Glu Glu Ile Gln Asp Val Ser Gly Thr Trp Tyr Leu Lys
1               5                   10                  15

Ala Met Thr Val Asp Arg Phe Lys Ile Ala Ser Trp Pro Arg Ser Val
                20                  25                  30

Thr Pro Met Thr Leu Thr Thr Leu Glu Gly Gly Asn Leu Glu Ala Lys
            35                  40                  45

Val Thr Met Asn Trp Trp Gly Arg Ser Gln Glu Val Lys Ala Val Leu
        50                  55                  60

Glu Arg Thr Asp Glu Pro Gly Lys Tyr Thr Ala Gln Gly Asp Arg His
65                  70                  75                  80

Val Ala Tyr Ile Ile Arg Ser Pro Val Lys Asp His Tyr Ile Phe Tyr
                85                  90                  95

Ser Glu Gly Asn Leu Gln Gly Glu Thr Val Pro Gly Val Trp Leu Val
            100                 105                 110

Gly Arg Asp Pro Lys Asn Asn Leu Glu Ala Leu Glu Phe Glu Lys
            115                 120                 125

Ala Ala Gly Ala Arg Gly Leu Ser Thr Glu Ser Ile Leu Ile Pro Arg
130                 135                 140

Gln Ser Glu Thr Ser Ser Pro Gly
145                 150

<210> SEQ ID NO 17
<211> LENGTH: 153
<212> TYPE: PRT
<213> ORGANISM: Artificial Sequence
<220> FEATURE:
<223> OTHER INFORMATION: Synthesized

<400> SEQUENCE: 17

Gly Ala Ser Asp Glu Glu Ile Gln Asp Val Ser Gly Thr Trp Tyr Leu
1               5                   10                  15

Lys Ala Met Thr Val Asp Arg Phe Lys Ile Ala Ser Trp Pro Arg Ser
            20                  25                  30

Val Thr Pro Met Thr Leu Thr Thr Leu Glu Gly Gly Asn Leu Glu Ala
        35                  40                  45

Lys Val Thr Met Asn Trp Trp Gly Arg Ser Gln Glu Val Lys Ala Val
50                  55                  60

Leu Glu Arg Thr Asp Glu Pro Gly Lys Tyr Thr Ala Gln Gly Asp Arg
65                  70                  75                  80

His Val Ala Tyr Ile Ile Arg Ser His Val Lys Asp His Tyr Ile Phe
                85                  90                  95

Tyr Ser Glu Gly Asn Leu Gln Gly Glu Thr Val Pro Gly Val Trp Leu
            100                 105                 110

Val Gly Arg Asp Pro Lys Asn Asn Leu Glu Ala Leu Glu Asp Phe Glu
        115                 120                 125

Lys Ala Ala Gly Ala Arg Gly Leu Ser Thr Glu Ser Ile Leu Ile Pro
130                 135                 140

Arg Gln Ser Glu Thr Ser Ser Pro Gly
145                 150

<210> SEQ ID NO 18
<211> LENGTH: 203
<212> TYPE: PRT
<213> ORGANISM: Artificial Sequence
<220> FEATURE:
<223> OTHER INFORMATION: Synthesized

<400> SEQUENCE: 18

Ala Ser Asp Glu Glu Ile Gln Asp Val Ser Gly Thr Trp Tyr Leu Lys
1               5                   10                  15

Ala Met Thr Val Asp Arg Phe Lys Ile Ala Ser Trp Pro Arg Ser Val
            20                  25                  30

Thr Pro Met Thr Leu Thr Thr Leu Glu Gly Gly Asn Leu Glu Ala Lys
        35                  40                  45

Val Thr Met Asn Trp Trp Gly Arg Ser Gln Gln Val Lys Ala Val Leu
50                  55                  60

Glu Arg Thr Asp Glu Pro Gly Lys Tyr Thr Ala Gln Gly Asp Arg His
65                  70                  75                  80

Val Ala Tyr Ile Ile Arg Ser Pro Val Lys Asp His Tyr Ile Phe Tyr
                85                  90                  95

Ser Glu Gly Asn Leu Gln Gly Glu Thr Val Pro Gly Val Trp Leu Val
            100                 105                 110

Gly Arg Asp Pro Lys Asn Asn Leu Glu Ala Leu Glu Asp Phe Glu Lys
            115                 120                 125

Ala Ala Gly Ala Arg Gly Leu Ser Thr Glu Ser Ile Leu Ile Pro Arg
    130                 135                 140

Gln Ser Glu Thr Ser Ser Pro Gly Gly Gly Ser Leu Ala Glu Ala
145                 150                 155                 160

Lys Glu Ala Ala Asn Ala Glu Leu Asp Ser Tyr Gly Val Ser Asp Phe
                165                 170                 175

Tyr Lys Arg Leu Ile Asp Lys Ala Lys Thr Val Glu Gly Val Glu Ala
            180                 185                 190

Leu Lys Asp Ala Ile Leu Ala Ala Leu Pro Gly
            195                 200

<210> SEQ ID NO 19
<211> LENGTH: 210
<212> TYPE: PRT
<213> ORGANISM: Artificial Sequence
<220> FEATURE:
<223> OTHER INFORMATION: Synthesized

<400> SEQUENCE: 19

Gly Ala Ser Asp Glu Glu Ile Gln Asp Val Ser Gly Thr Trp Tyr Leu
1               5                   10                  15

Lys Ala Met Thr Val Asp Arg Phe Lys Ile Ala Ser Trp Pro Arg Ser
            20                  25                  30

Val Thr Pro Met Thr Leu Thr Thr Leu Glu Gly Gly Asn Leu Glu Ala
        35                  40                  45

Lys Val Thr Met Asn Trp Trp Gly Arg Ser Gln Glu Val Lys Ala Val
    50                  55                  60

Leu Glu Arg Thr Asp Glu Pro Gly Lys Tyr Thr Ala Gln Gly Asp Arg
65                  70                  75                  80

His Val Ala Tyr Ile Ile Arg Ser His Val Lys Asp His Tyr Ile Phe
                85                  90                  95

Tyr Ser Glu Gly Asn Leu Gln Gly Glu Thr Val Pro Gly Val Trp Leu
            100                 105                 110

Val Gly Arg Asp Pro Lys Asn Asn Leu Glu Ala Leu Glu Asp Phe Glu
            115                 120                 125

Lys Ala Ala Gly Ala Arg Gly Leu Ser Thr Glu Ser Ile Leu Ile Pro
        130                 135                 140

Arg Gln Ser Glu Thr Ser Ser Pro Gly Lys Leu Gly Gly Gly Ser
145                 150                 155                 160

Leu Ala Glu Ala Lys Glu Ala Ala Asn Ala Glu Leu Asp Ser Tyr Gly
                165                 170                 175

Val Ser Asp Phe Tyr Lys Arg Leu Ile Asp Lys Ala Lys Thr Val Glu
            180                 185                 190

Gly Val Glu Ala Leu Lys Asp Ala Ile Leu Ala Ala Leu Pro Gly Lys
        195                 200                 205

Leu Asn
    210

<210> SEQ ID NO 20
<211> LENGTH: 357
<212> TYPE: PRT
<213> ORGANISM: Artificial Sequence
<220> FEATURE:
<223> OTHER INFORMATION: Synthesized

<400> SEQUENCE: 20

```
Met Gly Arg Gln Leu Ala Gly Cys Gly Asp Ala Gly Lys Lys Ala Ser
1               5                   10                  15

Phe Lys Met Ser Thr Val His Glu Ile Leu Cys Lys Leu Ser Leu Glu
            20                  25                  30

Gly Asp His Ser Thr Pro Pro Ser Ala Tyr Gly Ser Val Lys Ala Tyr
        35                  40                  45

Thr Asn Phe Asp Ala Glu Arg Asp Ala Leu Asn Ile Glu Thr Ala Ile
    50                  55                  60

Lys Thr Lys Gly Val Asp Glu Val Thr Ile Val Asn Ile Leu Thr Asn
65                  70                  75                  80

Arg Ser Asn Ala Gln Arg Gln Asp Ile Ala Phe Ala Tyr Gln Arg Arg
                85                  90                  95

Thr Lys Lys Glu Leu Ala Ser Ala Leu Lys Ser Ala Leu Ser Gly His
            100                 105                 110

Leu Glu Thr Val Ile Leu Gly Leu Leu Lys Thr Pro Ala Gln Tyr Asp
        115                 120                 125

Ala Ser Glu Leu Lys Ala Ser Met Lys Gly Leu Gly Thr Asp Glu Asp
    130                 135                 140

Ser Leu Ile Glu Ile Ile Cys Ser Arg Thr Asn Gln Glu Leu Gln Glu
145                 150                 155                 160

Ile Asn Arg Val Tyr Lys Glu Met Tyr Lys Thr Asp Leu Glu Lys Asp
                165                 170                 175

Ile Ile Ser Asp Thr Ser Gly Asp Phe Arg Lys Leu Met Val Ala Leu
            180                 185                 190

Ala Lys Gly Arg Arg Ala Glu Asp Gly Ser Val Ile Asp Tyr Glu Leu
        195                 200                 205

Ile Asp Gln Asp Ala Arg Asp Leu Tyr Asp Ala Gly Val Lys Arg Lys
    210                 215                 220

Gly Thr Asp Val Pro Lys Trp Ile Ser Ile Met Thr Glu Arg Ser Val
225                 230                 235                 240

Pro His Leu Gln Lys Val Phe Asp Arg Tyr Lys Ser Tyr Ser Pro Tyr
                245                 250                 255

Asp Met Leu Glu Ser Ile Arg Lys Glu Val Lys Gly Asp Leu Glu Asn
            260                 265                 270

Ala Phe Leu Asn Leu Val Gln Cys Ile Gln Asn Lys Pro Leu Tyr Phe
        275                 280                 285

Ala Asp Arg Leu Tyr Asp Ser Met Lys Gly Lys Gly Thr Arg Asp Lys
    290                 295                 300

Val Leu Ile Arg Ile Met Val Ser Arg Ser Glu Val Asp Met Leu Lys
305                 310                 315                 320

Ile Arg Ser Glu Phe Lys Arg Lys Tyr Gly Lys Ser Leu Tyr Tyr Tyr
                325                 330                 335

Ile Gln Gln Asp Thr Lys Gly Asp Tyr Gln Lys Ala Leu Leu Tyr Leu
            340                 345                 350

Cys Gly Gly Asp Asp
        355
```

<210> SEQ ID NO 21
<211> LENGTH: 339
<212> TYPE: PRT
<213> ORGANISM: Artificial Sequence
<220> FEATURE:
<223> OTHER INFORMATION: Synthesized

<400> SEQUENCE: 21

Met Ser Thr Val His Glu Ile Leu Cys Lys Leu Ser Leu Glu Gly Asp
1               5                   10                  15

His Ser Thr Pro Pro Ser Ala Tyr Gly Ser Val Lys Ala Tyr Thr Asn
            20                  25                  30

Phe Asp Ala Glu Arg Asp Ala Leu Asn Ile Glu Thr Ala Ile Lys Thr
        35                  40                  45

Lys Gly Val Asp Glu Val Thr Ile Val Asn Ile Leu Thr Asn Arg Ser
    50                  55                  60

Asn Ala Gln Arg Gln Asp Ile Ala Phe Ala Tyr Gln Arg Arg Thr Lys
65                  70                  75                  80

Lys Glu Leu Ala Ser Ala Leu Lys Ser Ala Leu Ser Gly His Leu Glu
                85                  90                  95

Thr Val Ile Leu Gly Leu Leu Lys Thr Pro Ala Gln Tyr Asp Ala Ser
            100                 105                 110

Glu Leu Lys Ala Ser Met Lys Gly Leu Gly Thr Asp Glu Asp Ser Leu
        115                 120                 125

Ile Glu Ile Ile Cys Ser Arg Thr Asn Gln Glu Leu Gln Glu Ile Asn
    130                 135                 140

Arg Val Tyr Lys Glu Met Tyr Lys Thr Asp Leu Glu Lys Asp Ile Ile
145                 150                 155                 160

Ser Asp Thr Ser Gly Asp Phe Arg Lys Leu Met Val Ala Leu Ala Lys
                165                 170                 175

Gly Arg Arg Ala Glu Asp Gly Ser Val Ile Asp Tyr Glu Leu Ile Asp
            180                 185                 190

Gln Asp Ala Arg Asp Leu Tyr Asp Ala Gly Val Lys Arg Lys Gly Thr
        195                 200                 205

Asp Val Pro Lys Trp Ile Ser Ile Met Thr Glu Arg Ser Val Pro His
    210                 215                 220

Leu Glu Lys Val Phe Asp Arg Tyr Lys Ser Tyr Ser Pro Tyr Asp Met
225                 230                 235                 240

Leu Glu Ser Ile Arg Lys Glu Val Lys Gly Asp Leu Glu Asn Ala Phe
                245                 250                 255

Leu Asn Leu Val Gln Cys Ile Gln Asn Lys Pro Leu Tyr Phe Ala Asp
            260                 265                 270

Arg Leu Tyr Asp Ser Met Lys Gly Lys Gly Thr Arg Asp Lys Val Leu
        275                 280                 285

Ile Arg Ile Met Val Ser Arg Ser Glu Val Asp Met Leu Lys Ile Arg
    290                 295                 300

Ser Glu Phe Lys Arg Lys Tyr Gly Lys Ser Leu Tyr Tyr Tyr Ile Gln
305                 310                 315                 320

Gln Asp Thr Lys Gly Asp Tyr Gln Lys Ala Leu Leu Tyr Leu Cys Gly
                325                 330                 335

Gly Asp Asp

<210> SEQ ID NO 22
<211> LENGTH: 956
<212> TYPE: PRT
<213> ORGANISM: Artificial Sequence
<220> FEATURE:
<223> OTHER INFORMATION: Synthesized

<400> SEQUENCE: 22

Met Glu Lys Met Leu Ala Gly Cys Phe Leu Leu Ile Leu Gly Gln Ile
1               5                   10                  15

```
Val Leu Leu Pro Ala Glu Ala Arg Glu Arg Ser Arg Gly Arg Ser Ile
            20                  25                  30

Ser Arg Gly Arg His Ala Arg Thr His Pro Gln Thr Ala Leu Leu Glu
        35                  40                  45

Ser Ser Cys Glu Asn Lys Arg Ala Asp Leu Val Phe Ile Ile Asp Ser
    50                  55                  60

Ser Arg Ser Val Asn Thr His Asp Tyr Ala Lys Val Lys Glu Phe Ile
65                  70                  75                  80

Val Asp Ile Leu Gln Phe Leu Asp Ile Gly Pro Asp Val Thr Arg Val
                85                  90                  95

Gly Leu Leu Gln Tyr Gly Ser Thr Val Lys Asn Glu Phe Ser Leu Lys
            100                 105                 110

Thr Phe Lys Arg Lys Ser Glu Val Glu Arg Ala Val Lys Arg Met Arg
        115                 120                 125

His Leu Ser Thr Gly Thr Met Thr Gly Leu Ala Ile Gln Tyr Ala Leu
130                 135                 140

Asn Ile Ala Phe Ser Glu Ala Glu Gly Ala Arg Pro Leu Arg Glu Asn
145                 150                 155                 160

Val Pro Arg Val Ile Met Ile Val Thr Asp Gly Arg Pro Gln Asp Ser
                165                 170                 175

Val Ala Glu Val Ala Ala Lys Ala Arg Asp Thr Gly Ile Leu Ile Phe
            180                 185                 190

Ala Ile Gly Val Gly Gln Val Asp Phe Asn Thr Leu Lys Ser Ile Gly
        195                 200                 205

Ser Glu Pro His Glu Asp His Val Phe Leu Val Ala Asn Phe Ser Gln
    210                 215                 220

Ile Glu Thr Leu Thr Ser Val Phe Gln Lys Lys Leu Cys Ile Asn Ile
225                 230                 235                 240

Met Cys Ser Thr Leu Glu His Asn Cys Ala His Phe Cys Ile Asn Ile
                245                 250                 255

Pro Gly Ser Tyr Val Cys Arg Cys Lys Gln Gly Tyr Ile Leu Asn Ser
            260                 265                 270

Asp Gln Thr Thr Cys Arg Ile Gln Asp Leu Cys Ala Met Glu Asp His
        275                 280                 285

Asn Cys Glu Gln Leu Cys Val Asn Val Pro Gly Ser Phe Val Cys Gln
    290                 295                 300

Cys Tyr Ser Gly Tyr Ala Leu Ala Glu Asp Gly Lys Arg Cys Val Ala
305                 310                 315                 320

Val Asp Tyr Cys Ala Ser Glu Asn His Gly Cys Glu His Glu Cys Val
                325                 330                 335

Asn Ala Asp Gly Ser Tyr Leu Cys Gln Cys His Glu Gly Phe Ala Leu
            340                 345                 350

Asn Pro Asp Lys Lys Thr Cys Thr Lys Ile Asp Tyr Cys Ala Ser Ser
        355                 360                 365

Asn His Gly Cys Gln His Glu Cys Val Asn Thr Asp Asp Ser Tyr Ser
    370                 375                 380

Cys His Cys Leu Lys Gly Phe Thr Leu Asn Pro Asp Lys Lys Thr Cys
385                 390                 395                 400

Arg Arg Ile Asn Tyr Cys Ala Leu Asn Lys Pro Gly Cys Glu His Glu
                405                 410                 415

Cys Val Asn Met Glu Glu Ser Tyr Tyr Cys Arg Cys His Arg Gly Tyr
            420                 425                 430
```

-continued

```
Thr Leu Asp Pro Asn Gly Lys Thr Cys Ser Arg Val Asp His Cys Ala
            435                 440                 445
Gln Gln Asp His Gly Cys Glu Gln Leu Cys Leu Asn Thr Glu Asp Ser
        450                 455                 460
Phe Val Cys Gln Cys Ser Glu Gly Phe Leu Ile Asn Glu Asp Leu Lys
465                 470                 475                 480
Tyr Cys Ser Arg Val Asp Tyr Cys Leu Leu Ser Asp His Gly Cys Glu
                485                 490                 495
Tyr Ser Cys Val Asn Met Asp Arg Ser Phe Ala Cys Gln Cys Pro Glu
            500                 505                 510
Gly His Val Leu Arg Ser Asp Gly Lys Thr Cys Ala Lys Leu Asp Ser
        515                 520                 525
Cys Ala Leu Gly Asp His Gly Cys Glu His Ser Cys Val Ser Ser Glu
530                 535                 540
Asp Ser Phe Val Cys Gln Cys Phe Glu Gly Tyr Ile Leu Arg Glu Asp
545                 550                 555                 560
Gly Lys Thr Cys Arg Arg Lys Asp Val Cys Gln Ala Ile Asp His Gly
                565                 570                 575
Cys Glu His Ile Cys Val Asn Ser Asp Asp Ser Tyr Thr Cys Glu Cys
            580                 585                 590
Leu Glu Gly Phe Arg Leu Ala Glu Asp Gly Lys Arg Cys Arg Arg Lys
        595                 600                 605
Asp Val Cys Lys Ser Thr His His Gly Cys Glu His Ile Cys Val Asn
610                 615                 620
Asn Gly Asn Ser Tyr Ile Cys Lys Cys Ser Glu Gly Phe Val Leu Ala
625                 630                 635                 640
Glu Asp Gly Arg Arg Cys Lys Lys Cys Thr Glu Gly Pro Ile Asp Leu
                645                 650                 655
Val Phe Val Ile Asp Gly Ser Lys Ser Leu Gly Glu Glu Asn Phe Glu
            660                 665                 670
Val Val Lys Gln Phe Val Thr Gly Ile Ile Asp Ser Leu Thr Ile Ser
        675                 680                 685
Pro Lys Ala Ala Arg Val Gly Leu Leu Gln Tyr Ser Thr Gln Val His
690                 695                 700
Thr Glu Phe Thr Leu Arg Asn Phe Asn Ser Ala Lys Asp Met Lys Lys
705                 710                 715                 720
Ala Val Ala His Met Lys Tyr Met Gly Lys Gly Ser Met Thr Gly Leu
                725                 730                 735
Ala Leu Lys His Met Phe Glu Arg Ser Phe Thr Gln Gly Glu Gly Ala
            740                 745                 750
Arg Pro Leu Ser Thr Arg Val Pro Arg Ala Ala Ile Val Phe Thr Asp
        755                 760                 765
Gly Arg Ala Gln Asp Asp Val Ser Glu Trp Ala Ser Lys Ala Lys Ala
770                 775                 780
Asn Gly Ile Thr Met Tyr Ala Val Gly Val Gly Lys Ala Ile Glu Glu
785                 790                 795                 800
Glu Leu Gln Glu Ile Ala Ser Glu Pro Thr Asn Lys His Leu Phe Tyr
                805                 810                 815
Ala Glu Asp Phe Ser Thr Met Asp Glu Ile Ser Glu Lys Leu Lys Lys
            820                 825                 830
Gly Ile Cys Glu Ala Leu Glu Asp Ser Asp Gly Arg Gln Asp Ser Pro
        835                 840                 845
Ala Gly Glu Leu Pro Lys Thr Val Gln Gln Pro Thr Glu Ser Glu Pro
```

```
                850                 855                 860
Val Thr Ile Asn Ile Gln Asp Leu Leu Ser Cys Ser Asn Phe Ala Val
865                 870                 875                 880

Gln His Arg Tyr Leu Phe Glu Glu Asp Asn Leu Leu Arg Ser Thr Gln
                885                 890                 895

Lys Leu Ser His Ser Thr Lys Pro Ser Gly Ser Pro Leu Glu Glu Lys
                900                 905                 910

His Asp Gln Cys Lys Cys Glu Asn Leu Ile Met Phe Gln Asn Leu Ala
                915                 920                 925

Asn Glu Glu Val Arg Lys Leu Thr Gln Arg Leu Glu Glu Met Thr Gln
                930                 935                 940

Arg Met Glu Ala Leu Glu Asn Arg Leu Arg Tyr Arg
945                 950                 955

<210> SEQ ID NO 23
<211> LENGTH: 937
<212> TYPE: PRT
<213> ORGANISM: Artificial Sequence
<220> FEATURE:
<223> OTHER INFORMATION: Synthesized

<400> SEQUENCE: 23

Met Glu Lys Met Leu Ala Gly Cys Phe Leu Leu Ile Leu Gly Gln Ile
1               5                   10                  15

Val Leu Leu Pro Ala Glu Ala Arg Glu Arg Ser Arg Gly Arg Ser Ile
                20                  25                  30

Ser Arg Gly Arg His Ala Arg Thr His Pro Gln Thr Ala Leu Leu Glu
                35                  40                  45

Ser Ser Cys Glu Asn Lys Arg Ala Asp Leu Val Phe Ile Ile Asp Ser
                50                  55                  60

Ser Arg Ser Val Asn Thr His Asp Tyr Ala Lys Val Lys Glu Phe Ile
65                  70                  75                  80

Val Asp Ile Leu Gln Phe Leu Asp Ile Gly Pro Asp Val Thr Arg Val
                85                  90                  95

Gly Leu Leu Gln Tyr Gly Ser Thr Val Lys Asn Glu Phe Ser Leu Lys
                100                 105                 110

Thr Phe Lys Arg Lys Ser Glu Val Glu Arg Ala Val Lys Arg Met Arg
                115                 120                 125

His Leu Ser Thr Gly Thr Met Thr Gly Leu Ala Ile Gln Tyr Ala Leu
                130                 135                 140

Asn Ile Ala Phe Ser Glu Ala Glu Gly Ala Arg Pro Leu Arg Glu Asn
145                 150                 155                 160

Val Pro Arg Val Ile Met Ile Val Thr Asp Gly Arg Pro Gln Asp Ser
                165                 170                 175

Val Ala Glu Val Ala Ala Lys Ala Arg Asp Thr Gly Ile Leu Ile Phe
                180                 185                 190

Ala Ile Gly Val Gly Gln Val Asp Phe Asn Thr Leu Lys Ser Ile Gly
                195                 200                 205

Ser Glu Pro His Glu Asp His Val Phe Leu Val Ala Asn Phe Ser Gln
                210                 215                 220

Ile Glu Thr Leu Thr Ser Val Phe Gln Lys Lys Leu Cys Thr Ala His
225                 230                 235                 240

Met Cys Ser Thr Leu Glu His Asn Cys Ala His Phe Cys Ile Asn Ile
                245                 250                 255

Pro Gly Ser Tyr Val Cys Arg Cys Lys Gln Gly Tyr Ile Leu Asn Ser
```

```
                260                 265                 270
Asp Gln Thr Thr Cys Arg Ile Gln Asp Leu Cys Ala Met Glu Asp His
            275                 280                 285

Asn Cys Glu Gln Leu Cys Val Asn Val Pro Gly Ser Phe Val Cys Gln
            290                 295                 300

Cys Tyr Ser Gly Tyr Ala Leu Ala Glu Asp Gly Lys Arg Cys Val Ala
305                 310                 315                 320

Val Asp Tyr Cys Ala Ser Glu Asn His Gly Cys Glu His Glu Cys Val
                325                 330                 335

Asn Ala Asp Gly Ser Tyr Leu Cys Gln Cys His Glu Gly Phe Ala Leu
            340                 345                 350

Asn Pro Asp Lys Lys Thr Cys Thr Lys Ile Asp Tyr Cys Ala Ser Ser
            355                 360                 365

Asn His Gly Cys Gln His Glu Cys Val Asn Thr Asp Asp Ser Tyr Ser
            370                 375                 380

Cys His Cys Leu Lys Gly Phe Thr Leu Asn Pro Asp Lys Lys Thr Cys
385                 390                 395                 400

Arg Arg Ile Asn Tyr Cys Ala Leu Asn Lys Pro Gly Cys Glu His Glu
                405                 410                 415

Cys Val Asn Met Glu Glu Ser Tyr Tyr Cys Arg Cys His Arg Gly Tyr
            420                 425                 430

Thr Leu Asp Pro Asn Gly Lys Thr Cys Ser Arg Val Asp His Cys Ala
            435                 440                 445

Glu Glu Asp His Gly Cys Glu Gln Leu Cys Leu Asn Thr Glu Asp Ser
            450                 455                 460

Phe Val Cys Gln Cys Ser Glu Gly Phe Leu Ile Asn Glu Asp Leu Lys
465                 470                 475                 480

Thr Cys Ser Arg Val Asp Tyr Cys Leu Leu Ser Asp His Gly Cys Glu
                485                 490                 495

Tyr Ser Cys Val Asn Met Asp Arg Ser Phe Ala Cys Gln Cys Pro Glu
            500                 505                 510

Gly His Val Leu Arg Ser Asp Gly Lys Thr Cys Ala Lys Leu Asp Ser
            515                 520                 525

Cys Ala Leu Gly Asp His Gly Cys Glu His Ser Cys Val Ser Ser Glu
            530                 535                 540

Asp Ser Phe Val Cys Gln Cys Phe Glu Gly Tyr Ile Leu Arg Glu Asp
545                 550                 555                 560

Gly Lys Thr Cys Arg Arg Lys Asp Val Cys Gln Ala Ile Asp His Gly
                565                 570                 575

Cys Glu His Ile Cys Val Asn Ser Asp Asp Ser Tyr Thr Cys Glu Cys
            580                 585                 590

Leu Glu Gly Phe Arg Leu Ala Glu Asp Gly Lys Arg Cys Arg Arg Lys
            595                 600                 605

Asp Val Cys Lys Ser Thr His His Gly Cys Glu His Ile Cys Val Asn
            610                 615                 620

Asn Gly Asn Ser Tyr Ile Cys Lys Cys Ser Glu Gly Phe Val Leu Ala
625                 630                 635                 640

Glu Asp Gly Arg Arg Cys Lys Lys Cys Thr Glu Gly Pro Ile Asp Leu
                645                 650                 655

Val Phe Val Ile Asp Gly Ser Lys Ser Leu Gly Glu Glu Asn Phe Glu
            660                 665                 670

Val Val Lys Gln Phe Val Thr Gly Ile Ile Asp Ser Leu Thr Ile Ser
            675                 680                 685
```

Pro Lys Ala Arg Val Gly Leu Leu Gln Tyr Ser Thr Gln Val His
    690                 695                 700

Thr Glu Phe Thr Leu Arg Asn Phe Asn Ser Ala Lys Asp Met Lys Lys
705                 710                 715                 720

Ala Val Ala His Met Lys Tyr Met Gly Lys Gly Ser Met Thr Gly Leu
                725                 730                 735

Ala Leu Lys His Met Phe Glu Arg Ser Phe Thr Gln Gly Glu Gly Ala
                740                 745                 750

Arg Pro Leu Ser Thr Arg Val Pro Arg Ala Ala Ile Val Phe Thr Asp
            755                 760                 765

Gly Arg Ala Gln Asp Asp Val Ser Glu Trp Ala Ser Lys Ala Lys Ala
770                 775                 780

Asn Gly Ile Thr Met Tyr Ala Val Gly Val Gly Lys Ala Ile Glu Glu
785                 790                 795                 800

Glu Leu Gln Glu Ile Ala Ser Glu Pro Thr Asn Lys His Leu Phe Tyr
                805                 810                 815

Ala Glu Asp Phe Ser Thr Met Asp Glu Ile Ser Glu Lys Leu Lys Lys
                820                 825                 830

Gly Ile Cys Glu Ala Leu Glu Asp Ser Asp Gly Arg Gln Asp Ser Pro
            835                 840                 845

Ala Gly Glu Leu Pro Lys Thr Val Gln Gln Pro Thr Val Gln His Arg
850                 855                 860

Tyr Leu Phe Glu Glu Asp Asn Leu Leu Arg Ser Thr Gln Lys Leu Ser
865                 870                 875                 880

His Ser Thr Lys Pro Ser Gly Ser Pro Leu Glu Glu Lys His Asp Gln
                885                 890                 895

Cys Lys Cys Glu Asn Leu Ile Met Phe Gln Asn Leu Ala Asn Glu Glu
            900                 905                 910

Val Arg Lys Leu Thr Gln Arg Leu Glu Glu Met Thr Gln Arg Met Glu
            915                 920                 925

Ala Leu Glu Asn Arg Leu Arg Tyr Arg
    930                 935

<210> SEQ ID NO 24
<211> LENGTH: 119
<212> TYPE: PRT
<213> ORGANISM: Artificial Sequence
<220> FEATURE:
<223> OTHER INFORMATION: Variable zone in heavy chain

<400> SEQUENCE: 24

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
                20                  25                  30

Trp Ile Ser Trp Val Arg Gln Met Pro Gly Lys Gly Leu Glu Trp Met
            35                  40                  45

Gly Ile Ile Tyr Pro Gly Asp Ser Tyr Thr Asn Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp Tyr Trp Tyr Lys Pro Leu Phe Asp Ile Trp Gly Gln Gly
                100                 105                 110

```
Thr Leu Val Thr Val Ser Ser
        115

<210> SEQ ID NO 25
<211> LENGTH: 114
<212> TYPE: PRT
<213> ORGANISM: Artificial Sequence
<220> FEATURE:
<223> OTHER INFORMATION: Variable zone in light chain

<400> SEQUENCE: 25

Asp Ile Val Met Thr Gln Ser Pro Asp Ser Leu Ala Val Ser Leu Gly
1               5                   10                  15

Glu Arg Ala Thr Ile Asn Cys Arg Ser Ser Gln Ser Val Leu Tyr Ser
            20                  25                  30

Ser Asn Asn Lys Asn Tyr Leu Ala Trp Tyr Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Ser Ser Phe Pro Ile Thr Phe Gly Gln Gly Thr Lys Val Glu Ile
            100                 105                 110

Lys Arg

<210> SEQ ID NO 26
<211> LENGTH: 120
<212> TYPE: PRT
<213> ORGANISM: Artificial Sequence
<220> FEATURE:
<223> OTHER INFORMATION: Variable zone in heavy chain

<400> SEQUENCE: 26

Glu Val Gln Leu Leu Glu Ser Gly Gly Gly Leu Val Gln Pro Gly Gly
1               5                   10                  15

Ser Leu Arg Leu Ser Cys Lys Ala Ser Gly Tyr Thr Phe Ser Ser Tyr
            20                  25                  30

Gly Met Tyr Trp Val Arg Gln Ala Pro Gly Lys Gly Leu Glu Trp Ile
        35                  40                  45

Gly Trp Ile Asp Pro Gly Ser Gly Gly Thr Lys Tyr Asn Glu Lys Phe
    50                  55                  60

Lys Gly Lys Ala Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Tyr Gly Tyr Tyr Phe Asp Tyr Trp Gly Gln Gly Thr
            100                 105                 110

Leu Val Thr Val Ser Ser Ala Ser
        115                 120

<210> SEQ ID NO 27
<211> LENGTH: 118
<212> TYPE: PRT
<213> ORGANISM: Artificial Sequence
<220> FEATURE:
<223> OTHER INFORMATION: Variable zone in heavy chain
```

```
<400> SEQUENCE: 27

Glu Val Gln Leu Leu Glu Ser Gly Gly Gly Leu Val Gln Pro Gly Gly
1               5                   10                  15

Ser Leu Arg Leu Ser Cys Lys Ala Ser Gly Tyr Thr Phe Ser Ser Tyr
            20                  25                  30

Gly Met Tyr Trp Val Arg Gln Ala Pro Gly Lys Gly Leu Glu Trp Ile
        35                  40                  45

Gly Trp Ile Asp Pro Gly Ser Gly Gly Thr Lys Tyr Asn Glu Lys Phe
    50                  55                  60

Lys Gly Lys Ala Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Tyr Gly Tyr Tyr Phe Asp Tyr Trp Gly Gln Gly Thr
            100                 105                 110

Leu Val Thr Val Ser Ser
            115

<210> SEQ ID NO 28
<211> LENGTH: 108
<212> TYPE: PRT
<213> ORGANISM: Artificial Sequence
<220> FEATURE:
<223> OTHER INFORMATION: Variable zone in light chain

<400> SEQUENCE: 28

Glu Ile Val Leu Thr Gln Ser Pro Ala Thr Leu Ser Leu Ser Pro Gly
1               5                   10                  15

Glu Arg Ala Thr Ile Thr Cys Arg Ala Ser Gln Tyr Val Gly Ser Tyr
            20                  25                  30

Leu Asn Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Val Trp Asp Ser Ser Pro Pro
                85                  90                  95

Val Val Phe Gly Gly Gly Thr Lys Val Glu Ile Lys
            100                 105

<210> SEQ ID NO 29
<211> LENGTH: 119
<212> TYPE: PRT
<213> ORGANISM: Artificial Sequence
<220> FEATURE:
<223> OTHER INFORMATION: Variable zone in heavy chain

<400> SEQUENCE: 29

Glu Val Gln Leu Leu Glu Ser Gly Gly Gly Leu Val Gln Pro Gly Gly
1               5                   10                  15

Ser Leu Arg Leu Ser Cys Lys Ala Ser Gly Phe Thr Phe Thr Ser Tyr
            20                  25                  30

Tyr Met His Trp Val Arg Gln Ala Pro Gly Lys Gly Leu Glu Trp Ile
        35                  40                  45

Gly Arg Ile Asn Pro Asp Ser Gly Ser Thr Lys Tyr Asn Glu Lys Phe
    50                  55                  60
```

```
Lys Gly Arg Ala Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Gly Arg Leu Ser Trp Asp Phe Asp Val Trp Gly Gln Gly
            100                 105                 110

Thr Leu Val Thr Val Ser Ser
        115
```

<210> SEQ ID NO 30
<211> LENGTH: 109
<212> TYPE: PRT
<213> ORGANISM: Artificial Sequence
<220> FEATURE:
<223> OTHER INFORMATION: Variable zone in light chain

<400> SEQUENCE: 30

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Asp Ile Ser Arg Tyr
                 20                  25                  30

Leu Ala Trp Tyr Gln Gln Lys Pro Gly Lys Ala Pro Lys Leu Leu Ile
             35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Ala Ala Tyr Asp Tyr Ser Leu Gly
                 85                  90                  95

Gly Tyr Val Phe Gly Asp Gly Thr Lys Val Glu Ile Lys
            100                 105
```

<210> SEQ ID NO 31
<211> LENGTH: 109
<212> TYPE: PRT
<213> ORGANISM: Artificial Sequence
<220> FEATURE:
<223> OTHER INFORMATION: Variable zone in light chain

<400> SEQUENCE: 31

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Asp Ile Ser Arg Tyr
                 20                  25                  30

Leu Ala Trp Tyr Gln Gln Lys Pro Gly Lys Ala Pro Lys Leu Leu Ile
             35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Ala Ala Tyr Asp Tyr Ser Leu Gly
                 85                  90                  95

Gly Tyr Val Phe Gly Gly Gly Thr Lys Val Glu Ile Lys
            100                 105
```

<210> SEQ ID NO 32
<211> LENGTH: 131
<212> TYPE: PRT
<213> ORGANISM: Artificial Sequence

```
<220> FEATURE:
<223> OTHER INFORMATION: Variable zone in heavy chain

<400> SEQUENCE: 32

Gln Val Gln Leu Val Gln Ser Gly Ala Glu Val Lys Pro Gly Ser
1               5                   10                  15

Ser Val Lys Val Ser Cys Lys Ala Ser Gly Gly Thr Phe Asn Ser His
            20                  25                  30

Ala Ile Ser Trp Val Arg Gln Ala Pro Gly Gln Gly Leu Glu Trp Met
        35                  40                  45

Gly Gly Ile Asn Pro Ile Leu Gly Ile Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg His Tyr Glu Ile Gln Ile Gly Arg Tyr Gly Met Asn Val Tyr
            100                 105                 110

Tyr Leu Met Tyr Arg Phe Ala Ser Trp Gly Gln Gly Thr Leu Val Thr
        115                 120                 125

Val Ser Ser
    130

<210> SEQ ID NO 33
<211> LENGTH: 107
<212> TYPE: PRT
<213> ORGANISM: Artificial Sequence
<220> FEATURE:
<223> OTHER INFORMATION: Variable zone in light chain

<400> SEQUENCE: 33

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Ser Ala
            20                  25                  30

Leu Asn Trp Tyr Gln Gln Lys Pro Gly Lys Ala Pro Lys Leu Leu Ile
        35                  40                  45

Tyr Asn Gly Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln Phe Asp Gly Asp Pro Thr
                85                  90                  95

Phe Gly Gln Gly Thr Lys Val Glu Ile Lys Arg
            100                 105

<210> SEQ ID NO 34
<211> LENGTH: 451
<212> TYPE: PRT
<213> ORGANISM: Artificial Sequence
<220> FEATURE:
<223> OTHER INFORMATION: LY3015014 Heavy chain

<400> SEQUENCE: 34

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Pro Phe Ser Lys Leu
            20                  25                  30
```

```
Gly Met Val Trp Val Arg Gln Ala Pro Gly Lys Gly Leu Glu Trp Val
        35                  40                  45

Ser Thr Ile Ser Ser Gly Gly Tyr Thr Tyr Tyr Pro Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Glu Gly Ile Ser Phe Gln Gly Gly Thr Tyr Thr Tyr Val Met
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Cys Ser Arg Ser Thr Ser
130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Lys Thr Tyr Thr Cys
        195                 200                 205

Asn Val Asp His Lys Pro Ser Asn Thr Lys Val Asp Lys Arg Val Glu
    210                 215                 220

Ser Lys Tyr Gly Pro Pro Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

Gln Glu Asp Pro Glu Val Gln Phe Asn Trp Tyr Val Asp Gly Val Glu
        275                 280                 285

Val His Asn Ala Lys Thr Lys Pro Arg Glu Glu Gln Phe Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Gln Glu Glu Met Thr Lys Asn Gln Val
        355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
                405                 410                 415

Val Asp Lys Ser Arg Trp Gln Glu Gly Asn Val Phe Ser Cys Ser Val
            420                 425                 430

Met His Glu Ala Leu His Asn His Tyr Thr Gln Lys Ser Leu Ser Leu
        435                 440                 445

Ser Leu Gly
```

```
<210> SEQ ID NO 35
<211> LENGTH: 219
<212> TYPE: PRT
<213> ORGANISM: Artificial Sequence
<220> FEATURE:
<223> OTHER INFORMATION: LY3015014 Light chain

<400> SEQUENCE: 35
```

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Arg
            20                  25                  30

Asn Gly Ile Thr Tyr Ser Tyr Trp Tyr Leu Gln Lys Pro Gly Gln Ser
        35                  40                  45

Pro Gln Leu Leu Ile Tyr Gln Leu Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Tyr Gln Asn
                85                  90                  95

Leu Glu Leu Pro Leu Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

```
<210> SEQ ID NO 36
<211> LENGTH: 118
<212> TYPE: PRT
<213> ORGANISM: Artificial Sequence
<220> FEATURE:
<223> OTHER INFORMATION: Variable zone in heavy chain

<400> SEQUENCE: 36
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Thr Met
            20                  25                  30

Tyr Met Ser Trp Val Arg Gln Ala Pro Gly Gln Gly Leu Glu Trp Met
        35                  40                  45

Gly Arg Ile Asp Pro Ala Asn Glu His Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

```
Met Glu Leu Ser Arg Leu Thr Ser Asp Asp Thr Ala Val Tyr Tyr Cys
                85                  90                  95

Ala Arg Ser Tyr Tyr Tyr Asn Met Asp Tyr Trp Gly Gln Gly Thr
            100                 105                 110

Leu Val Thr Val Ser Ser
        115
```

<210> SEQ ID NO 37
<211> LENGTH: 106
<212> TYPE: PRT
<213> ORGANISM: Artificial Sequence
<220> FEATURE:
<223> OTHER INFORMATION: Variable zone in light chain

<400> SEQUENCE: 37

```
Gln Ile Val Leu Thr Gln Ser Pro Ala Thr Leu Ser Val Ser Pro Gly
1               5                   10                  15

Glu Arg Ala Thr Leu Ser Cys Arg Ala Ser Gln Ser Val Ser Tyr Met
                20                  25                  30

His Trp Tyr Gln Gln Lys Pro Gly Gln Ala Pro Arg Leu Leu Ile Tyr
            35                  40                  45

Gly Val Phe Arg Arg Ala Thr Gly Ile Pro Asp Arg Phe Ser Gly Ser
        50                  55                  60

Gly Ser Gly Thr Asp Phe Thr Leu Thr Ile Gly Arg Leu Glu Pro Glu
65                  70                  75                  80

Asp Phe Ala Val Tyr Tyr Cys Leu Gln Trp Ser Ser Asp Pro Pro Thr
                85                  90                  95

Phe Gly Gln Gly Thr Lys Leu Glu Ile Lys
            100                 105
```

<210> SEQ ID NO 38
<211> LENGTH: 118
<212> TYPE: PRT
<213> ORGANISM: Artificial Sequence
<220> FEATURE:
<223> OTHER INFORMATION: Variable zone in heavy chain

<400> SEQUENCE: 38

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Thr Met
                20                  25                  30

Tyr Met Ser Trp Val Arg Gln Ala Pro Gly Gln Gly Leu Glu Trp Met
            35                  40                  45

Gly Arg Ile Asp Pro Ala Asn Glu His Thr Asn Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Arg Leu Thr Ser Asp Asp Thr Ala Val Tyr Tyr Cys
                85                  90                  95

Ala Arg Ser Tyr Tyr Tyr Asn Met Asp Tyr Trp Gly Gln Gly Thr
            100                 105                 110

Leu Val Thr Val Ser Ser
        115
```

<210> SEQ ID NO 39
<211> LENGTH: 106
<212> TYPE: PRT
<213> ORGANISM: Artificial Sequence

```
<220> FEATURE:
<223> OTHER INFORMATION: Variable zone in light chain

<400> SEQUENCE: 39

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Tyr Met
            20                  25                  30

His Trp Tyr Gln Gln Lys Pro Gly Gln Ala Pro Arg Leu Leu Ile Tyr
        35                  40                  45

Gly Val Phe Arg Arg Ala Thr Gly Ile Pro Asp Arg Phe Ser Gly Ser
    50                  55                  60

Gly Ser Gly Thr Asp Phe Thr Leu Thr Ile Gly Arg Leu Glu Pro Glu
65                  70                  75                  80

Asp Phe Ala Val Tyr Tyr Cys Leu Gln Trp Ser Asp Pro Pro Thr
                85                  90                  95

Phe Gly Gln Gly Thr Lys Leu Glu Ile Lys
            100                 105

<210> SEQ ID NO 40
<211> LENGTH: 118
<212> TYPE: PRT
<213> ORGANISM: Artificial Sequence
<220> FEATURE:
<223> OTHER INFORMATION: Variable zone in heavy chain

<400> SEQUENCE: 40

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Thr Met
            20                  25                  30

Tyr Met Ser Trp Val Arg Gln Ala Pro Gly Gln Gly Leu Glu Trp Met
        35                  40                  45

Gly Arg Ile Asp Pro Ala Asn Glu His Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Thr Ser Asp Asp Thr Ala Val Tyr Tyr Cys
                85                  90                  95

Ala Arg Ser Tyr Tyr Tyr Ala Met Asp Tyr Trp Gly Gln Gly Thr
            100                 105                 110

Leu Val Thr Val Ser Ser
        115

<210> SEQ ID NO 41
<211> LENGTH: 95
<212> TYPE: PRT
<213> ORGANISM: Artificial Sequence
<220> FEATURE:
<223> OTHER INFORMATION: Variable zone in light chain

<400> SEQUENCE: 41

Gln Ile Val Leu Thr Gln Ser Pro Ala Thr Leu Ser Val Ser Pro Gly
1               5                   10                  15

Glu Arg Ala Thr Leu Ser Cys Arg Ala Ser Gln Ser Val Ser Tyr Met
            20                  25                  30

His Trp Tyr Gln Gln Lys Pro Gly Gln Ala Pro Arg Leu Leu Ile Tyr
        35                  40                  45
```

```
Gly Val Phe Arg Arg Ala Thr Gly Ile Pro Asp Arg Phe Ser Gly Ser
        50                  55                  60

Gly Ser Gly Thr Asp Phe Thr Leu Thr Ile Gly Arg Leu Glu Pro Glu
 65                  70                  75                  80

Asp Phe Ala Val Tyr Tyr Cys Leu Gln Trp Ser Ser Asp Pro Pro
                     85                  90                  95

<210> SEQ ID NO 42
<211> LENGTH: 23
<212> TYPE: DNA
<213> ORGANISM: Artificial Sequence
<220> FEATURE:
<223> OTHER INFORMATION: Primer sequence 5'-3' Sense
<220> FEATURE:
<221> NAME/KEY: misc_feature
<222> LOCATION: (2)..(4)
<223> OTHER INFORMATION: 2'-OMe modification
<220> FEATURE:
<221> NAME/KEY: misc_feature
<222> LOCATION: (9)..(11)
<223> OTHER INFORMATION: 2'-OMe modification
<220> FEATURE:
<221> NAME/KEY: misc_feature
<222> LOCATION: (13)..(15)
<223> OTHER INFORMATION: 2'-OMe modification
<220> FEATURE:
<221> NAME/KEY: misc_feature
<222> LOCATION: (20)..(20)
<223> OTHER INFORMATION: 2'-OMe modification
<220> FEATURE:
<221> NAME/KEY: misc_feature
<222> LOCATION: (22)..(22)
<223> OTHER INFORMATION: 2'-OMe modification
<220> FEATURE:
<221> NAME/KEY: polyA_signal
<222> LOCATION: (22)..(22)

<400> SEQUENCE: 42
gccuggaguu uauucggaad tdt                                             23

<210> SEQ ID NO 43
<211> LENGTH: 23
<212> TYPE: DNA
<213> ORGANISM: Artificial Sequence
<220> FEATURE:
<223> OTHER INFORMATION: Primer sequence 5'-3' Sense
<220> FEATURE:
<221> NAME/KEY: misc_feature
<222> LOCATION: (4)..(4)
<223> OTHER INFORMATION: 2'-OMe modification
<220> FEATURE:
<221> NAME/KEY: misc_feature
<222> LOCATION: (6)..(6)
<223> OTHER INFORMATION: 2'-OMe modification
<220> FEATURE:
<221> NAME/KEY: misc_feature
<222> LOCATION: (8)..(13)
<223> OTHER INFORMATION: 2'-OMe modification
<220> FEATURE:
<221> NAME/KEY: misc_feature
<222> LOCATION: (17)..(17)
<223> OTHER INFORMATION: 2'-OMe modification
<220> FEATURE:
<221> NAME/KEY: misc_feature
<222> LOCATION: (19)..(20)
<223> OTHER INFORMATION: 2'-OMe modification
<220> FEATURE:
<221> NAME/KEY: misc_feature
<222> LOCATION: (22)..(22)
<223> OTHER INFORMATION: 2'-OMe modification

<400> SEQUENCE: 43
agguguaucu ccuagacacd tdt                                             23
```

```
<210> SEQ ID NO 44
<211> LENGTH: 23
<212> TYPE: DNA
<213> ORGANISM: Artificial Sequence
<220> FEATURE:
<223> OTHER INFORMATION: Primer sequence 5'-3' Sense
<220> FEATURE:
<221> NAME/KEY: misc_feature
<222> LOCATION: (1)..(3)
<223> OTHER INFORMATION: 2'-OMe modification
<220> FEATURE:
<221> NAME/KEY: misc_feature
<222> LOCATION: (5)..(5)
<223> OTHER INFORMATION: 2'-OMe modification
<220> FEATURE:
<221> NAME/KEY: misc_feature
<222> LOCATION: (7)..(8)
<223> OTHER INFORMATION: 2'-OMe modification
<220> FEATURE:
<221> NAME/KEY: misc_feature
<222> LOCATION: (12)..(12)
<223> OTHER INFORMATION: 2'-OMe modification
<220> FEATURE:
<221> NAME/KEY: misc_feature
<222> LOCATION: (14)..(17)
<223> OTHER INFORMATION: 2'-OMe modification
<220> FEATURE:
<221> NAME/KEY: misc_feature
<222> LOCATION: (20)..(20)
<223> OTHER INFORMATION: 2'-OMe modification
<220> FEATURE:
<221> NAME/KEY: misc_feature
<222> LOCATION: (22)..(22)
<223> OTHER INFORMATION: 2'-OMe modification

<400> SEQUENCE: 44
cuuacgcuga guacuucgad tdt                                            23

<210> SEQ ID NO 45
<211> LENGTH: 23
<212> TYPE: DNA
<213> ORGANISM: Artificial Sequence
<220> FEATURE:
<223> OTHER INFORMATION: Primer sequence 5'-3' Antisense
<220> FEATURE:
<221> NAME/KEY: misc_feature
<222> LOCATION: (5)..(5)
<223> OTHER INFORMATION: 2'-OMe modification
<220> FEATURE:
<221> NAME/KEY: misc_feature
<222> LOCATION: (8)..(8)
<223> OTHER INFORMATION: 2'-OMe modification
<220> FEATURE:
<221> NAME/KEY: misc_feature
<222> LOCATION: (15)..(15)
<223> OTHER INFORMATION: 2'-OMe modification
<220> FEATURE:
<221> NAME/KEY: misc_feature
<222> LOCATION: (20)..(20)
<223> OTHER INFORMATION: 2'-OMe modification
<220> FEATURE:
<221> NAME/KEY: misc_feature
<222> LOCATION: (22)..(22)
<223> OTHER INFORMATION: 2'-OMe modification

<400> SEQUENCE: 45
uuccgaauaa acuccaggcd tdt                                            23

<210> SEQ ID NO 46
<211> LENGTH: 23
<212> TYPE: DNA
<213> ORGANISM: Artificial Sequence
<220> FEATURE:
```

```
<223> OTHER INFORMATION: Primer sequence 5'-3' Antisense
<220> FEATURE:
<221> NAME/KEY: misc_feature
<222> LOCATION: (6)..(6)
<223> OTHER INFORMATION: 2'-OMe modification
<220> FEATURE:
<221> NAME/KEY: misc_feature
<222> LOCATION: (13)..(13)
<223> OTHER INFORMATION: 2'-OMe modification
<220> FEATURE:
<221> NAME/KEY: misc_feature
<222> LOCATION: (15)..(15)
<223> OTHER INFORMATION: 2'-OMe modification
<220> FEATURE:
<221> NAME/KEY: misc_feature
<222> LOCATION: (20)..(20)
<223> OTHER INFORMATION: 2'-OMe modification

<400> SEQUENCE: 46
gugucuagga gauacaccud tdt                                            23

<210> SEQ ID NO 47
<211> LENGTH: 23
<212> TYPE: DNA
<213> ORGANISM: Artificial Sequence
<220> FEATURE:
<223> OTHER INFORMATION: Primer sequence 5'-3' Antisense
<220> FEATURE:
<221> NAME/KEY: misc_feature
<222> LOCATION: (7)..(7)
<223> OTHER INFORMATION: 2'-OMe modification
<220> FEATURE:
<221> NAME/KEY: misc_feature
<222> LOCATION: (11)..(11)
<223> OTHER INFORMATION: 2'-OMe modification
<220> FEATURE:
<221> NAME/KEY: misc_feature
<222> LOCATION: (16)..(16)
<223> OTHER INFORMATION: 2'-OMe modification
<220> FEATURE:
<221> NAME/KEY: misc_feature
<222> LOCATION: (20)..(20)
<223> OTHER INFORMATION: 2'-OMe modification
<220> FEATURE:
<221> NAME/KEY: misc_feature
<222> LOCATION: (22)..(22)
<223> OTHER INFORMATION: 2'-OMe modification

<400> SEQUENCE: 47
ucgaaguacu cagcguaagd tdt                                            23

<210> SEQ ID NO 48
<211> LENGTH: 19
<212> TYPE: DNA
<213> ORGANISM: Artificial Sequence
<220> FEATURE:
<223> OTHER INFORMATION: Primer sequence (forward sequence)

<400> SEQUENCE: 48
ttgcagcagc tgggaactt                                                 19

<210> SEQ ID NO 49
<211> LENGTH: 23
<212> TYPE: DNA
<213> ORGANISM: Artificial Sequence
<220> FEATURE:
<223> OTHER INFORMATION: Primer sequence (forward sequence)

<400> SEQUENCE: 49
ctggtggaca catacaggaa gac                                            23
```

```
<210> SEQ ID NO 50
<211> LENGTH: 20
<212> TYPE: DNA
<213> ORGANISM: Artificial Sequence
<220> FEATURE:
<223> OTHER INFORMATION: Primer sequence (forward sequence)

<400> SEQUENCE: 50
ttttcagcaa ggaatgtgga                                               20

<210> SEQ ID NO 51
<211> LENGTH: 20
<212> TYPE: DNA
<213> ORGANISM: Artificial Sequence
<220> FEATURE:
<223> OTHER INFORMATION: Primer sequence (forward sequence)

<400> SEQUENCE: 51
tttcctgacc aaactcagca                                               20

<210> SEQ ID NO 52
<211> LENGTH: 22
<212> TYPE: DNA
<213> ORGANISM: Artificial Sequence
<220> FEATURE:
<223> OTHER INFORMATION: Primer sequence (forward sequence)

<400> SEQUENCE: 52
cacctcccta ctaggactca gc                                            22

<210> SEQ ID NO 53
<211> LENGTH: 21
<212> TYPE: DNA
<213> ORGANISM: Artificial Sequence
<220> FEATURE:
<223> OTHER INFORMATION: Primer sequence (reverse sequence)

<400> SEQUENCE: 53
ccgactgtga tgacctctgg a                                             21

<210> SEQ ID NO 54
<211> LENGTH: 24
<212> TYPE: DNA
<213> ORGANISM: Artificial Sequence
<220> FEATURE:
<223> OTHER INFORMATION: Primer sequence (reverse sequence)

<400> SEQUENCE: 54
ataggcactg tcttctttca cctc                                          24

<210> SEQ ID NO 55
<211> LENGTH: 19
<212> TYPE: DNA
<213> ORGANISM: Artificial Sequence
<220> FEATURE:
<223> OTHER INFORMATION: Primer sequence (reverse sequence)

<400> SEQUENCE: 55
ttcattgtgg agggcagac                                                19

<210> SEQ ID NO 56
<211> LENGTH: 20
<212> TYPE: DNA
<213> ORGANISM: Artificial Sequence
<220> FEATURE:
<223> OTHER INFORMATION: Primer sequence (reverse sequence)
```

```
<400> SEQUENCE: 56
ctggatgttc tggtcgtcac                                          20

<210> SEQ ID NO 57
<211> LENGTH: 18
<212> TYPE: DNA
<213> ORGANISM: Artificial Sequence
<220> FEATURE:
<223> OTHER INFORMATION: Primer sequence (reverse sequence)

<400> SEQUENCE: 57
tgggcatctg ttgggtct                                            18
```